(12) United States Patent
Ashdown et al.

(10) Patent No.: US 9,239,904 B2
(45) Date of Patent: *Jan. 19, 2016

(54) COMPUTER SYSTEMS FOR TREATING DISEASES

(71) Applicant: BIOTEMPUS LIMITED, Victoria (AU)

(72) Inventors: Martin Leonard Ashdown, Victoria (AU); Andrew Robinson, Victoria (AU)

(73) Assignee: BIOTEMPUS LIMITED (AU)

(*) Notice: Subject to any disclaimer, the term of this patent is extended or adjusted under 35 U.S.C. 154(b) by 0 days.

This patent is subject to a terminal disclaimer.

(21) Appl. No.: 13/848,128

(22) Filed: Mar. 21, 2013

(65) Prior Publication Data

US 2013/0218475 A1    Aug. 22, 2013

Related U.S. Application Data

(63) Continuation of application No. 13/322,357, filed as application No. PCT/AU2010/000649 on May 27, 2010, now Pat. No. 9,122,778.

(60) Provisional application No. 61/181,508, filed on May 27, 2009.

(51) Int. Cl.

| G01N 33/48 | (2006.01) |
|---|---|
| G06F 19/00 | (2011.01) |
| G01N 33/564 | (2006.01) |
| G01N 33/574 | (2006.01) |
| A61B 5/00 | (2006.01) |
| G06F 19/24 | (2011.01) |
| G06F 19/12 | (2011.01) |

(52) U.S. Cl.
CPC . *G06F 19/34* (2013.01); *A61B 5/41* (2013.01); *G01N 33/564* (2013.01); *G01N 33/57407* (2013.01); *G06F 19/24* (2013.01); *A61B 5/7267* (2013.01); *G01N 2800/042* (2013.01); *G01N 2800/102* (2013.01); *G01N 2800/104* (2013.01); *G01N 2800/24* (2013.01); *G01N 2800/28* (2013.01); *G01N 2800/2821* (2013.01); *G01N 2800/2828* (2013.01); *G01N 2800/52* (2013.01); *G01N 2800/60* (2013.01); *G06F 19/12* (2013.01)

(58) Field of Classification Search
CPC .................................................... G06F 19/34
USPC ............................................................ 702/19
See application file for complete search history.

(56) References Cited

U.S. PATENT DOCUMENTS

| 5,057,423 A | 10/1991 | Hiserodt et al. |
|---|---|---|
| 5,141,867 A | 8/1992 | Ivanoff et al. |
| 5,308,626 A | 5/1994 | Landucci et al. |
| 5,358,852 A | 10/1994 | Wu |
| 5,814,639 A | 9/1998 | Liotta et al. |
| 5,939,400 A | 8/1999 | Steinmann et al. |
| 6,090,392 A | 7/2000 | Berman |
| 6,107,020 A | 8/2000 | Skowron |
| 6,110,898 A | 8/2000 | Malone et al. |
| 2002/0094542 A1 | 7/2002 | Leskovar |
| 2003/0198970 A1 | 10/2003 | Roberts |
| 2003/0228320 A1 | 12/2003 | Ashdown |
| 2004/0180357 A1 | 9/2004 | Reich et al. |
| 2004/0192629 A1 | 9/2004 | Xu et al. |
| 2004/0203024 A1 | 10/2004 | Baker et al. |
| 2005/0002929 A1 | 1/2005 | Sanchez-Madrid et al. |
| 2005/0180971 A1 | 8/2005 | Ashdown |
| 2006/0134713 A1 | 6/2006 | Rylat et al. |
| 2007/0202119 A1 | 8/2007 | Ashdown |
| 2008/0248022 A1 | 10/2008 | Ashdown |
| 2009/0041760 A1 | 2/2009 | Ashdown |
| 2011/0053289 A1 | 3/2011 | Lowe et al. |
| 2012/0156225 A1 | 6/2012 | Ashdown |
| 2012/0220640 A1 | 8/2012 | Ashdown et al. |
| 2013/0151165 A1 | 6/2013 | Ashdown et al. |
| 2014/0051100 A1 | 2/2014 | Ashdown |
| 2014/0065644 A1 | 3/2014 | Ashdown |

FOREIGN PATENT DOCUMENTS

| DE | 4120296 | 3/1992 |
|---|---|---|
| EP | 0239400 | 9/1987 |
| EP | 0358154 | 3/1990 |
| EP | 0374207 | 6/1990 |
| EP | 0656778 | 6/1995 |
| EP | 0736533 | 10/1996 |
| EP | 0945727 | 9/1999 |
| WO | WO 89/09620 | 10/1989 |
| WO | WO 90/07119 | 6/1990 |
| WO | WO 91/09872 | 7/1991 |

(Continued)

OTHER PUBLICATIONS

Perera et al. "Inflammatory Changes, Recovery and Recurrence at COPD Exacerbation" (2007) European Respiratory Journal (2007) vol. 29, pp. 527-534.*

(Continued)

*Primary Examiner* — Jerry Lin

(74) *Attorney, Agent, or Firm* — Sheridan Ross P.C.

(57) ABSTRACT

The present invention relates to computer-implemented methods and system for analyzing a biomarker which cycles in a subject. In some other aspects, the present invention relates to analyzing a biomarker which at least initially increases or decreases in amount in a subject following a treatment for a disease. In further aspects, the present invention relates to computer-implemented methods and systems for determining a preferred time to administer a therapy to treat a disease in a subject. The present invention also relates to computer program product to implement the methods. Further, the present invention relates to methods of determining the timing of treating a disease in a subject in which the immune system is cycling.

9 Claims, 24 Drawing Sheets

(56) References Cited

FOREIGN PATENT DOCUMENTS

| WO | WO 92/22654 | 12/1992 |
|---|---|---|
| WO | WO 93/19183 | 9/1993 |
| WO | WO 94/07921 | 4/1994 |
| WO | WO 95/20660 | 8/1995 |
| WO | WO 96/30025 | 10/1996 |
| WO | WO 98/44001 | 10/1998 |
| WO | WO 01/08702 | 2/2001 |
| WO | WO 02/13828 | 2/2002 |
| WO | WO 02/45735 | 6/2002 |
| WO | WO 03/068257 | 8/2003 |
| WO | WO 03/070270 | 8/2003 |
| WO | WO 2005/034995 | 4/2005 |
| WO | WO 2005/040816 | 5/2005 |
| WO | WO 2005/070090 | 8/2005 |
| WO | WO 2005/072777 | 8/2005 |
| WO | WO 2006/026821 | 3/2006 |

OTHER PUBLICATIONS

U.S. Appl. No. 13/738,580, filed Jan. 10, 2013, Ashdown et al.
Ataxia telangiectasia, Wikipedia, found at http://en.wikipedia.org/wiki/Ataxia_telangiectasia, last modified Jun. 11, 2011, 8 pages.
Cockayne syndrome, Wikipedia, found at http://en.wikipedia.org/wiki/Cockayne_syndrome, last updated Jun. 11, 2011, 3 pages.
ABC Online, "AM—Cells Switched off for tumour treatment", Mar. 12, 2009, http://www.abc.net.au/am/content/2008/s2513799.htm, accessed Apr. 5, 2009.
Adachi, Susumu, et al., "A Pilot Study of Paclitaxel and Carboplatin for Recurrent Ovarian Cancer" Oncology Reports 8: 285-288, 2001.
Agelaki, S., et al., "Second-line treatment with vinorelbine and carboplatin in patients with advanced non-small cell lung cancer. A multicenter phase 11study." Lung Cancer. Dec. 2001; 34 Suppl 4:S77-80.
Ahlers, J. et al., "A Push-pull Approach to Maximize Vaccine Efficacy: Abrogating Suppression with an IL-13 Inhibitor While Augmenting Help with Granulocyte/Macrophage Colony-Stimulating Factor and CD40L", Proceedings of the National Academy of Sciences of the United States of America. Oct. 2002. vol. 99, No. 20.
Ahmad, s. A., et al., "Extraosseous osteosarcoma: response to treatment and long-term outcome" J Clin Oncol. Jan. 15, 2002;20(2):521-7.
Aitini, E., et al., Epirubiciin, cicplatin and continuous infusion 5-fluorouracil (ECF) in locally advanced or metastatic gastric cancer: a single institution experience Tumori. Jan.-Feb. 2001; 87(1):20-4.
Allan, et al., CD4+ T-regulatory cells: toward therapy for human diseases, Immunological Reviews, 2008, vol. 223, Iss. 1 pp. 391-421.
Amadori, D., et al., Ovarian cancer: natural history and metastatic pattern. Front Biosci. Jan. 1, 1997;2:g8-10.
Anderson, et al., "The Effects of Cyclophosphamide and Irradiation Singly and in Combination Upon Sal Growth in A/J Mice," American Journal of Pathology, May 1987, vol. 127, No. 2, pp. 373-379.
Annunziato, et al., "Phenotype, Localization, and Mechanism of Suppression of CD4+ CD25+ Human Thymocytes," The Journal of Experimental Medicine, vol. 196, No. 3, pp. 379-387, Aug. 5, 2002.
Ashamalla, H.. et al., Hyperfractionated radiotherapy and paclitaxel for locally advanced/unresectable pancreatic cancer. Int J Radiat Oncol Bioi Phys. Mar. 1, 2003; 55(3):679-87.
Atkins MB, et al .. "A phase II pilot trial of concurrent biochemotherapy with cisplatin, vinblastine, temozolomide, interleukin 2, and IFN-alpha 2B in patients with metastatic melanoma." Clin. Cancer Res. Oct. 2002;8(10):3075-81.
Awwad, et al., "Cyclophosphamide-induced Immunologically Mediated Regression of a Cyclophosphamide-resistant Murine Tumor: A Consequence of Elimination Precursor L3T4+ Suppressor T-Cells," Cancer Research, 1989, vol. 49, No. 7, pp. 1649-1654.
Aziz, Mehar, M.D., et al., "Evaluation of Cell-Mediated Immunity and Circulating Immune Complexes as Prognostic Indicators in Cancer Patients" Cancer Detection and Prevention, 22(2):87-99 (1998).
Babbe, et al., "Clonal Expansions of CD8+ T Cells Dominate the T Cell Infiltrate in Active Multiple Sclerosis Lesions as Shown by Micromanipulation and Single Cell Polymerase Chain Reaction," The Journal of Experimental Medicine, vol. 192, No. 3, pp. 393-404, Aug. 7, 2000.
Bach "Regulatory T Cells Under Scrutiny," Nature Reviews, Immunology, Mar. 2003, vol. 3, pp. 189-198.
Bafaloukos D., et al., "Docetaxel in combination with dacarbazine in patients with advanced melanoma." Oncology. 2002;63(4):333-7.
Bafaloukos D., et al., "Temozolomide in combination with docetaxel in patients with advanced melanoma: a phase II study of the Hellenic Cooperative Oncology Group." J Clin Oncol. Jan. 15, 2002;20(2):420-5.
Balint, et al., "Immune complexes with antiglobulin activity in sera of Moloney sarcoma-bearing rats," Clin. Exp. Immunol., 1982, vol. 48, pp. 70-78.
Bar Sela, G.. et al. Etoposide, doxorubicin and cisplatin alternating with 5-fluorouracil, doxorubicin and high-dose methotrexate in patients with advanced adenocarcinoma of the stomach or the gastroesophageal junction. J Chemother. Dec. 2002;14(61:623-6).
Barin. F. et al.; Virus Envelope Protein of HTLV-III Represents Major Target Antigen for Antibodies in AIDS 54 Patients; May 31,1985; pp. 1094-1096; V. 228; Science; Gale Group Information Integrity.
Barrett, et al., "Undulations in the Time-Response Curve for Tumor Immunity after Primary Immunization with Washed Erythrocytes," Journal of National Cancer Institute, vol. 18, No. 1, Jan. 1957, pp. 57-63.
Bataille. R.. et at,—Cytokines and lymphoplasmocytic proliferations: essential role or interleukin 6. xp. 002351766. Feb. 1, 1993. La Revue du practicien. vol. 43. No. 3. pp. 275-278.
Beck TM. et al. Treatment of metastatic colorectal carcinoma with 5-FU. mitomycin, vincristine and methotrexate. Cancer Treat Rep. Apr. 1984;68(4):647-50.
Bedikian AY. et al., "Phase II trial of docetaxel in patients with advanced cutaneous malignant melanoma previously untreated with chemotherapy" J Clin Oncol. Dec. 1995;13(12):2865-B.
Beerblock. K. et al., Bimonthly high dose leucovorin and 5-fluorouracil 48-hour continuous infusion in patients with advanced colorectal carcinoma. Groupe d'Etude et de Recherche sur les Cancers de l'Ovaire et Digestifs (GERCODI. Cancer. Mar. 15, 1997; 79(61: 1100-5.) (Abstract only).
Beilharz et al., "Timed ablation of regulatory CD4+ T cells can prevent murine AIDS progression" J Immunol 2004, 172:4917-4925.
Beilharz et al., "Prevention of Murine AIDS by timed immune regulator cell ablation", Journal of Interferon and Cytokine Research, vol. 22, No. suppl. 1, Oct. 2002, pp. S-171.
Belkaid et al., "Natural regulatory T cells in infectious disease" Nature Immunol 2005, 6(4):353-360.
Belkaid, et al., "Regulatory T Cells in the Control of Host-Microorganism Interactions," Annual Review of Immunology, 2009, vol. 27, 41 pages.
Belli, Filiberto, et al., Vaccination of Metastatic Melanoma Patients with Autologous Tumor-Derived Heat Shock Protein gp96-Peptide Complexes: Clinical and Immunologic Findings Journal of clinical Oncology, vol. 20, No. 20 Oct. 15, 2002: pp. 4169-4180.
Berd et al., "Treatment of Metastatic Melanoma with Autologous, Hapten-Modified Melanoma Vaccine: Regression of Pulmonary Metastases", Int. J. Cancer: 94, 531-539 (2001).
Berd, David, et at, Effect of Low Dose Cyclophosphamide on the Immune System of Cancer Patients: Depletion of CD4+. 2H4+ Suppressor-inducer T-cells• XP 000900007 Cancer Research 48. 1671-1675. Mar. 15, 1988.
Berd. D "Effect of Low Dose Cyclophosphamide on the Immune System of Cancer Patients: Reduction of T-Suppressor Function without Depletion of the CD8+ Subset." XP-002351767 Cancer Research. vol. 47, Issue 12, Jun. 15, 1987.
Beyer et al., "Regulatory T cells in cancer" Blood 2006, 108(3)804•811.
Blanke CD, et al, "Phase II study of trimetrexate, fluorouracil, and leucovorin for advanced colorectal cancer" J Clin Oncol, Mar. 1997; 15(3):915-20 retrieved from the Internet Dec. 19, 2006.
Bon G., et al., "Fluctuations in CA 125 and CA 15-3 Serum Concentrations During Spontaneous Ovulatory Cycles", Human Reoroduction, Feb. 1999, vol. 14, No. 2, pp. 566-570.

(56) References Cited

OTHER PUBLICATIONS

Borjabad A, Brooks AI, Volsky DJ. "Gene expression profiles of HIV-1-infected glia and brain: toward better understanding of the role of astrocytes in HIV-1-associated neurocognitive disorders." J Neuroimmune Pharmacol. Mar. 2010;5(1 ):44-62. Epub Aug. 21, 2009. Review.
Bottazzo, et al., "In Situ Characterization of Autoimmune Phenomena and Expression of HLA Molecules in the Pancreas in Diabetic Insulitis," The New England Journal of Medicine, 1985, vol. 313, pp. 353-360.
Brandi et al., "Effect of antiviral treatments on the bone marrow in murine AIDS" Blood Cells, Molecules and Diseases 1995, 21 (12)109-118.
Brennan et al., "Chimeric Plant Virus Particles Administered Nasally or Orally Induce Systemic and Mucosal Immune Responses in mice," Journal of Virology, Feb. 1999, vol. 73, No. 2, pp. 930-938.
Bretz, et al., "Inflammatory Cytokine Regulation of Fas-mediated Apoptosis in Thyroid Follicular Cells," The Journal of Biological Chemistry, vol. 274, No. 36, pp. 25433-25438, Sep. 3, 1999.
Brusko, et al., "Human regulatory T cells: role in autoimmune disease and therapeutic opportunities," Immunological Reviews, 2008, vol. 223, Iss. 1, pp. 371-390.
Bruzzone, et al., "Temporal Patterns of C-Reactive Proteins and Other Acute Phase Proteins After Kidney Transplantation," Transplantation Proceedings, vol. XIX, No. 5, pp. 3727-3730, Oct. 1987.
Buzaid A.C., et al., "Phase II study of neoadjuvant concurrent biochemotherapy in melanoma patients with local-regional metastases." Melanoma Res. 1998 De;8(6):549-56 abstract only.
Byrd, et al., "A Limited Memory Algorithm for Bound Constrained Optimization," SIAM Journal on Scientific Computing, 1995, vol. 16, No. 5, pp. 1190-1208.
Calvo, E., et al., Irinotecan, oxaliplatin, and 5-fluorouracil/leucovorin combination chemotherapy in advanced colorectal carcinoma: a phase II study. Clin Colorectal Cancer. Aug. 2002;2(2):104-10, abstract only.
Cao, et al., "Regulatory T Cell Expansion and Immune Activation during Untreated HIV Type 1 Infection Are Associated with Disease Progression" AIDS Research and Human Retroviruses, 2009, vol. 25, No. 2, pp. 183-191.
Carcelain G. et al. "Reconstitution of CD4+ T lymphocytes in HIV-infected individuals following antiretroviral therapy". Curr Opin Immunol. Aug. 2001; 13(4 ):483-8.
Cardoso et al., "Immunization with Plasmid DNA Encoding for the Measles Virus Hemagglutinin and Nucleoprotein Leads to Humoral and Cell-Mediated Immunity," Virology 225, 293-299 (1996), Article No. 0603.
Carini et al. (1994) AIDS Res. Hum. Retroviruses 10:121-130.
Carr, B.I., et al., "Phase II study of Spherex (degradable starch microspheres) injected into the hepatic artery in conjunction with doxorubicin and cisplatin in the treatment of advanced-stage hepatocellular carcinoma: interim analysis." Semin Oncol. Apr. 1997;24(2 Suppl 6):S6-97-S6-99, abstract only.
Cascinu, S., et al. "A phase II study of Tomudex alternated with methotrexate, 5-fluorouracil, leucovorin in first-line chemotherapy of metastatic colorectal cancer." Ann Oncol. 199 Aug; 10(8):985-7 (abstract only).
Cassinello, J. et al., "Phase II study of weekly irinotecan (CPT-II) as second-line treatment of patients with advanced colorectal cancer" Med Oncol. 2003; 20(1): 37-43.
Cassinello, J., et al., "Activity and safety of oxaliplatin with weekly 5-fluorouracil bolus and low-dose leucovorin as fist-line treatment for advanced colorectal cancer." Clin Colorectal Cancer. Aug. 2003; 3(2): 108-12 (abstract only).
Chahinian, A. P., et al., "Randomized phase II trial of cisplatin with mitomycin or doxorubicin for malignant mesothelioma by the Cancer and Leukemia Group B" J Clin Oncol, Aug. 1993; 11(8):1559-65.
Chan EY, et al. "Quantitative analysis of human immunodeficiency virus type 1-infected CD4+ cell proteome: dysregulated cell cycle progression and nuclear transport coincide with robust virus production" J Virol. Jul. 2007;81 (14):7571-83. Epub May 9, 2007.
Chapman. PB, et al., "Clinical results using biochemotherapy as a standard of care in advanced melanoma" Melanoma Res. Aug. 2002; 12(4):381-7.
Chattopadhyay, Sisir K. et al.; Structure of Endogenous Murine Leukemia Virus DNA in Mouse Genomes; Oct. 1980. pp. 5774-5778; V. 77. No. 10; Proc. Natl. Acad. Sci. USA; Biochemistry.
Child et al., "Serum beta 2 microglobulin and C-reactive protein in the monitoring of lymphomas findings in a multicenter study and experience in selected patients," Cancer, vol. 45, No. 2, pp. 318-326 (Jan. 1980).
Chino "Diagnosis of malignant melanoma in the nasal cavity with touch-fluorescence method and detection of 5-S-cysteinyldopa," Jibi Inkioka Tokeibu Geka, 1994, vol. 66, No. 4, pp. 313-318 (Abstract Only).
Cho EK, et al., "Epirubicin, cisplatin, and protracted venous infusion of 5-fluorouracil for advanced gastric carcinoma" J Korean Med Sci, Jun. 2002; 17(3):348-52.
Cho, et al., "Identification of Serum Amyloid a Protein as a Potentially Useful Biomarker to Monitor Relapse of Nasopharyngeal Cancer by Serum Proteomic Profiling," Clinical Cancer Research, vol. 10, pp. 43-52, Jan. 1, 2004.
Choi TK, et al., "Chemotherapy for advanced hepatocellular carcinoma. Adriamycin versus quadruple chemotherapy" Cancer, Feb. 1, 1984; 53(3): 401-5.
Colic. M. et al., "Thymic Response to Thermal Injury in Mice: I. Alterations of Thymocyte Subsets Studied by Flow Cytometry and Immunohistochemistry", Burns: Journal of the International Society for Burn Iniuries, Jun. 1989. vol. 15, No. 3, pp. 155-161.
Coll, J. et al.; Antibodies to Human Immunodeficiency Virus (HIV-1) in Autoimmune Diseases: Primary Sjogren's Syndrome. Systemic Lupus Erythematosus, Rheumatoid Arthritis and Autoimmune Thyroid Diseases; Dec. 21, 1995; DD. 451-457; V. 14. No. 4; Clinical Rheumatology.
Comella P., et al., Biweekly irinotecan or raltitrexed plus 5S-leucovorin and bolus 5-fluorouracil in advanced colorectal carcinoma: a Southern Italy Cooperative Oncology Group phase 11-111 randomized trial, Ann Oncol. Oct. 2000; 11(10):1323-33.
Conry et al., "Immune Response to a Carcinoembryonic Antigen Polynucleotide Vaccine," Cancer Research 54, 1164-1168, Mar. 1, 1994.
Constenia, M., et al., Docetaxel, 5-fluorouracil, and leucovorin as treatment for advanced gastric cancer: results of a phase II study, Gastric Cancer. 2002; 5(3):142-7.
Coulie et al., "A Monoclonal Cytolytic T-Lymphocyte Response Observed in a Melanoma Patient Vaccinated with Tumor-Specific Antigenic Peptide Encoded by Gene MAGE-3," PNAS, vol. 98, No. 18, 10290-10295, Aug. 28, 2001.
Covens, A., et al., "Phase 1l study of mitomycin C and 5 fluorouracil in platinum resistant ovarian cancer" Eur J Gynaecol Oncol., 1992; 13(2):125-30.
Coventry, et al., "CRP identifies homeostatic immune oscillations in cancer patients: a potential treatment targeting tool?" Journal of Translational Medicine, Nov. 30, 2009, 7:102.
Cox et al., "Bovine Herpesvirus 1: Immune Responses in Mice and Cattle Injected with Plasmid DNAn," Journal of Virology, vol. 67, No. 9, Sep. 1993, pp. 5664-5667.
Cunnigham RK et al. "Murine AIDS: a model for the human disease or a distinct entity?" Immunol Res. vol. 13(1994), pp. 21-28.
Daar E., et al., "Acute HIV Syndrome After Discontinuation of Antiretroviral Therapy in a Patient Treated Before Seroconversion", Annals of Internal Medicine, May 15, 1998, vol. 128. No. 10.
Database Biosis [online], Biosciences Information Service, Philadelphia, PA. 1994, Chino Kazuo, "Diagnosis of Malignant Melanoma in the Nasal Cavity with Touch Fluorescence Method and Detection of 5-S-Cysteinyldopa", database accession No. PREV1999497330363, abstract.
Database Medline [online], US National Library of Medicine, Bethesda, MD, Oct. 1985, Jibiki et al., "Tumor Markers in Testicular Tumors", database accession No. NLM3841165, abstract.
Davis et al., "DNA-Based Immunization Induces Continuous Secretion of Hepatitis B Surface Antigen and High Levels of Circulating Antibody," Human Molecular Genetics, 1993, vol. 2, No. 11, 1847-1851.

(56) References Cited

OTHER PUBLICATIONS

Davis et al., "Establishment of a Murine Model of Malignant Mesothelioma," Int. J. Cancer: 52,881-886 (1992).

Denham, et al., "The Occurrence of Two Types of Cytotoxic Lymphoid Cells in Mice Immunised with Allogeneic Tumour Cells," Transplantation, 1970, vol. 9, No. 4, pp. 366-382.

Dennehy. Penelope H; Active Immunization in the United States: Developments over the Past Decade. Clinical Microbiology Reviews; Oct. 2001; pp. 872-908; V. 14. No. 4; American Society for Microbiology.

Dias et al., "Animal models used for the evaluation of antiretroviral therapies" in Current HIV Research 2006, 4(4):431-446, Abstract only. On the world wide web at http://www.bentham.org/chivr/contabs/chiv4-4.htm.

Dieras V., et al., Multicentre phase II study of oxaliplatin as a single-agent in cisplatin/carboplatin +/- taxane pretreated ovarian cancer patients. Ann Oncol. Feb. 2002; 13(2):258-66.

DiPaola, R.S., et al., Gemcitabine combined with sequential paclitaxel and carboplatin in patients with urothelial cancers and other advanced malignancies. Med Sci Monit. Feb. 2003; 9(2):PI5-11.

Dittmer et al., "Functional impairment of CD8+ T cells by regulatory T cells during persistent retroviral infection" Immunity 2004, 20:293-303.

Eda et al., "Development of a New Microparticle-Enhanced Turbidimetric Assay for C-Reactive Protein With Superior Features in Analytical Sensitivity and Dynamic Rangen," Journal of Clinical Laboratory Analysis, 12:137-144 (1998).

Einzig, A. I., "A phase II study of taxol in patients with malignant melanoma" Invest New Drugs. Feb. 1991;9(1 )59-64.

Einzig, A. I., "Review of phase II trials of Taxol (paclitaxel) in patients with advanced ovarian cancer." Ann Oncol. 1994;5 Suppl 6:S29-32.

Einzig, AI., et al., "Phase II trial of docetaxel (Taxotere) in patients with metastatic melanoma previously untreated with cytotoxic chemotherapy" Med oncol. Jun. 1996;13(2): 111-7.

Eisenbraun et al., "Examination of Parameters Affecting the Elicitation of Humoral Immune Responses by Particle Bombardment-Mediated Genetic Immunization," DNA and Cell Biology, vol. 12, No. 9, 1993,pp. 791-797.

Elliott, et al., "Suppression of Fever and the Acute-Phase Response in a Patient with Juvenile Chronic Arthritis Treated with Monoclonal Antibody to Tumour Necrosis Factor-x (cA2)," British Journal of Rheumatology, vol. 36, No. 5, pp. 589-593, 1997.

Errante D. et al. "Hodgkin's disease in 35 patients with HIV infection: an experience with epirubicin, bleomycin, vinblastine and prednisone chemotherapy in combination with antiretroviral therapy and primary use of G-CSF". Ann Oncol. Feb. 1999; 10(2): 189-95.

Estes et al., "Simian Immunodeficiency Virus-Induced Lymphatic Tissue Fibrosis is Mediated by Transforming Growth Factor B1-Positive Regulatory T-Cells and Begins in Early Infection," Journal of Infectious Diseases, 2007:195, (Feb. 15) pp. 551-561.

Faivre, S., "Phase I-II and pharmacokinetic study of gemcitabine combined with oxaliplatin in patients with advanced non-small-cell lung cancer and ovarian carcinoma" Ann On col, Sep. 2002;13(9):1479-89.

Falcone, A., et al., "5-flluorouracil administered as a 48-hour chronomodulated infusion in combination with leucovorin and cisplatin: a randomized phase II study in metastatic colorectal cancer." Oncology. 2001 ;61 (1):28-35.

Fisson, et al., "Continuous Activation of Autoreactive CD4+ CD25+ Regulatory T Cells in the Steady State," The Journal of Experimental Medicine, vol. 198, No. 5, pp. 737-746, Sep. 1, 2003.

Forastiere, A.A., et al., "Cisplatin, vinblastine, and mitoguazone chemotherapy for epidermoid and adenocarcinoma of the esophagus." J. Clin Oncol. Aug. 1987;5(8): 1143-9.

Fountzilas, G., et al. "Radiation and concomitant weekly administration of paclitaxel in patients with glioblastoma multiforme. A phase II Study." J. Neurooncol. 1999;45(2):159-65.

Frasci, G., et al., "A phase I-II study on a gemcitabine-cyclophosphamide-fluorouracil/folinic acid triplet combination in anthracycline- and taxane-refractory breast cancer patients." Oncology. 2002;62(1 ):25-32.

Fraternale et al., "Repeated cycles of alternate administration of fludarabine and zidovudine plus didanosine inhibits murine AIDS and reduces proviral DNA content in lymph nodes to undetectable levels" Virolgy 2002, 302:354-362.

Freed, et al., "Early Detection of Renal Allograft Rejection by Serial Monitoring of Serum C-Reactive Protein," Transplantation, vol. 37, No. 2, pp. 215-218, Feb. 1984.

Freyer, G., et al ., "Phase II study of oral vinorelbine in first-line advanced breast cancer chemotherapy" J. Clin. Oncol. Jan. 1, 2003;21 (1):35-40. Epub Jan. 1, 2003.

Fu, et al., "CD4+ CD25+ CD62+ T-Regulatory Cell Subset Has Optimal Suppressive and Proliferative Potential," American Journal of Transplantation, vol. 4, No. 1, pp. 65-78, Jan. 2004.

Fujita et al., "The Value of Acute-Phase Protein Measurements After Curative Gastric Cancer Surgery", Arch. Surg. 1999, 134: 73-75.

Fumoleau, P., et al., "Phase II trial of weekly intravenous vinorelbine in first-line advanced breast cancer chemotherapy," J. Clin Oncol. Jul. 1993;11(7):1245-52.

Fynan et al., "DNA Vaccines: Protective Immunizations by Parenteral, Mucosal, and Gene-Gun Inoculations," Proc. Natl. Acad. Sci.,., USA, vol. 90, pp. 11478-11482, Dec. 1993.

Gajewski, et al., "Emerging Strategies in Regulatory T-cell Immunotherapies," Clinical Advances in Hematology & Oncology, 2009, vol. 7, Iss. 1, 8 pages.

Gamelin, E, et al., "Long-term weekly treatment of colorector metastic cancer with Fluorouracil and leucovorin: results of a multicentric prospective trial of fluorouracil dosage optimization by pharmacokinetic monitoring in 152 patients" J. Clin Oncol., Apr. 1998; 16(4): 1470-8, abstract only, retrieved from the Internet Dec. 19, 2006.

Gaur et al., "Role of a cytotoxic-T-lymphocyte epitope-defined, alternative gag open reading frame in the pathogenesis of a murine retrovirus-induced immunodeficiency syndrome" J Virol 2005, 79(7):4308-4315.

Gavin, Marc A. et al., Homeostasis and Anergy of CD4+CD25+ Suppressor T Cells In Vivo; Dec. 10, 2001; pp. 33-41; V. 3, No. 1; Howard Hughes Medical Institute, University of Washington; Nature Publishing Group http://immunol.nature.com.

Gebbia V., et al., Paclitaxel and epidoxorubicin or doxorubicin versus cyclophosphamide and epidoxorubicin as first-line chemotherapy for metastatic breast carcinoma: a randomised phase II study, Anticancer Res. Jan.-Feb. 2003; 23(1B): 765-71 retrieved from the Internet Dec. 19, 2006.

Gelinas, et al., "Immunotherapy for Alzheimer's disease," Proceedings of the National Academy of Sciences of the United States of America, vol. 101, No. 2, pp. 14657-14662, Oct. 5, 2004.

George et al., "Immunokinetics of Autoreactive CD4 T Cells in Blood: A Reporter for the "Hit-and-Run" Autoimmune Attack on Pancreas and Diabetes Progression", Journal of Autoimmunity vol. 23 (2004) pp. 151-160.

Ghyka G et al . An Experimental Model Comparing the Antineoplastic and the Immunosuppressive Effects of some Cytostatics• XP-02351730 Archives roumaines de pathologie experimentales et de microbiologie. Romania Jan.-Mar. 1989.

Gibbs, P., et al., "A phase II study of biochemotherapy for the treatment of metastatic malignant melanoma" Melanoma Res. Apr. 2000; 10(2):171-9 retrieved from the Internet Dec. 9, 2006.

Ginopoulos, P., et al., A phase II study with vinorelbine, gemcitabine and cisplatin in the treatment of patients with stage IIIb-IV non-small cell lung cancer (NSCLC). Lung Cancer, Jan. 1999; 23(1):31-7 retrieved ftom the Internet Dec. 19, 2006.

Glimelius, B., et al., "Irinotecan combined with bolus 5-fluorouracil and folinic acid Nordic schedule as first-line therapy in advanced colorectal cancer" Ann Oncol. Dec. 2002; 13(12):1868-73 retrieved from the Internet Dec. 9, 2006.

Gomez-Bernal, A, et al., "Biweekly docetaxel and vinorelbine in anthracycline-resistant metastatic breast cancer: a multicenter phase II study" Am J Clin Oncol., Apr. 2003; 26(2):127-31 retrieved from the Inernet Dec. 19, 2006.

(56) References Cited

OTHER PUBLICATIONS

Goorin AM, et al., Phase II/III trial of etoposide and high-dose ifosfamide in newly diagnosed metastatic osteosarcoma: a pediatric oncology group trial. J Clin Oncol. Jan. 15, 2002;20(2):426-33. retrieved from the Internet Dec. 19, 2006.
Gordon. A . et al., "Cisplatin Vinblastine and Bleomycin Combination Therapy in Resistant Gestational IB.F./ 4 Trophoblastic Disease," XP-002351699 Cancer. vol. 56. No. 7. 1986 pp. 1407-1410.
Goverman, Tolerance and autoimmunity in TCR transgenic mice specific for myelin basic protein: Immunological Reviews, vol. 169, No. 1, pp. 147-159, Jun. 1999.
Grem, J. L., et al. "Phase II study of fluorouracil, leucovorin, and interferon alfa-2a in metastatic colorectal carcinoma" J. Clin Oncol. Sep. 1993; 11(9): 1737-45.
Guastalla, J. P., et al. "Phase II trial for intraperitoneal cisplatin plus intravenous sodium thiosulphate in advanced ovarian carcinoma patients with minimal residual disease after cisplatin-based chemotherapy—a phase II study of the EORTC Gvnaecological Cancer Cooperative Group" Eur J Cancer. 1994;30AI1\:45-9.
Gundersen S, et al., "interferon in combination with vinblastine in advanced malignant melanoma. A phase I-II study." Cancer. Oct. 15, 1989;64(8):1617-9.
Hamajima et al. (1997) Clin. Immunol. Immunopathol. 83:179-184.
Hartley, Janet W. et al.; Retrovirus-Induced Murine Acquired Immunodeficiency Syndrome: Natural History of Infection and Differing Susceptibility of Inbred Mouse Strains; Mar. 1989; pp. 1223-1231; vol. 63, No. 3; Journal of Virology; American Society for Microbiology.
Henss, H., et al., "Phase-II study with the combination of cisplatin and doxorubicin in advanced malignant mesothelioma of the pleura." Onkologie. Jun. 1988;11(3):118-20.
Herniou et al., "Retroviral diversity and distribution in vertebrates" J Virol 1998, 72(7):5955-5966.
Hill, et al., "Total Body Irradiation and Acute Graft-Versus-Host Disease: The Role of Gastrointestinal Damage and Inflammatory Cytokines," Blood, vol. 90, No. 8, pp. 3204-3213, Oct. 15, 1997.
Hiroaki Mitsuya et al.; Targeted Therapy of Human Immunodeficiency Virus-Related Disease; Jul. 1991; 52 pp. 2369-2381; V. 5; The FASEB Journal.
Hiura, et al., "Both Regulatory T Cells and Antitumor Effector T Cells are primed in the same draining lymph nodes during tumor progression", Journal of Immunology, 2005, pp. 5058-5066.
Hofheinz R. D., et al., "High-dose 5-fluorouracil/folinic acid in combination with three-weekly mitomycin C in the treatment of advanced gastric cancer. A phase II study." Onkologie, Jun. 2002;25(3):255-60.
Holcombe et al., "The Immunosuppressive Agent 15-Deoxyspergualin Functions by Inhibiting Cell Cycle Progression and Cytokine Production Following Naïve T Cell Activation", Journal of Immunology, vol. 169, No. 9, pp. 4982-4989, 2002.
Hood et al., "Plant-Based Production of Xenogenic Proteins," Current Opinion in Biotechnology 1999, 10:382-386.
Horvath, Mogdolna. et al. "Investigation of circulating Immune Complexes in Patients with Breast Cancer." Oncology 39: 20-22 (1982).
Hryniewicz et al., "CTLA-4 blockage decreases TGF-B, IDO, and viral RNA expression in tissues of SIV mac251-infected macaques", Blood, vol. 108, No. 12, Dec. 1, 2006.
Huber et al., "Cycling of immune responses to a syngeneic murine mammary adenocarcinoma," Cancer Research, vol. 40 No. 10, pp. 3484-3490 (Oct. 1980).
Hudes, GR, et al., "Phase II trial of 96-hour paclitaxel plus oral estramustine phosphate in metastatic hormone-refractory prostate cancer." J. Clin. Oncol. Sep. 1997; 15(( ):3156-63.
Hughes P. et al., "Dual Labelling of Circulating CD8 Cells in Patients with Multiple Sclerosis", Journal of Neurology, Neurosurgery and Psychiatry, Jan. 1989. vol. 52, No. 1.
Hurteloup, P., et al. "Phase II clinical evaluation of doxifluridine." Cancer Treat. Rep. Jun. 1986; ZO(6):731-7.

Ibrahim, N. K., et al., "Phase II study of vinorelbine administered by 96-hour infusion in patients with advanced breast carcinoma." Cancer. Oct. 1, 1999;86(7):1251-7.
Imami et al. (1999) Clin. Exp. Immunol. 118: 78-86.
Imami et al., "Development of immunotherapeutic strategies for HIV-1", Expert Opinion, vol. 1, No. 5, Sep. 2001, pp. 803-816.
Iwashiro et al., "Immunosuppression by CD4+ regulatory T cells induced by chronic retroviral infection" PNAS 2001, 98( 16): 9226-9230.
Jarnicki et al., "Suppression of Antitumor Immunity by IL-10 and TGF-B-Producing T Cells Infiltrating the Growing Tumor: Influence of Tumor Environment on the Induction of CD4+ and CD8+ Regulatory T Cells" The Journal of Immunology, 2006, 177:896-904.
Jeen, YT, et al. "Phase II trial of epirubicin, cisplatin, oral uracil and tegafur, and leucovorin in patients with advanced gastric carcinoma." Cancer. Jun. 15, 2001;91 (12):2288-93.
Jeremic, B., et al., "Carboplatin and etoposide in advanced colorectal carcinoma. A phase" study. Cancer. May 1, 1993;71 (9):2706-8.
Jibiki et al. "Tumor markers in testicular tumors," Gan No Rinsho. Japan Journal of Cancer Clinics, Oct. 1985, vol. 31, No. 13, pp. 1709-1716 (Abstract Only).
Jin, Oon Chong, et al., "Adriamycin in the Treatment of Resectible and Irresectible Primary Hepatocellular Carcinoma" Annals Academy of Medicine, Apr. 1980, vol. 9, No. 2.
Jin-Hwang Liu, et al., "Tamoxifen and colchicine-modulated vinblastine followed by 5-fluorouracil in advanced renal cell carcinoma: a phase II study" Science Direct-Urology, vol. 57, Issue 4, Apr. 2001, pp. 650-654.
Johnson, D. H., et al. "Cisplatin, vinblastine, and bleomycin in the treatment of metastatic melanoma: a phase II study of the Southeastern Cancer Study Group." Cancer Treat Rep. Jul.-Aug. 1985;69(7-8):821-4.
Jonuleit, et al., "Identification and Functional Characterization of Human CD4+ CD25+ T Cells with Regulatory Properties Isolated from Peripheral Blood," The Journal of Experimental Medicine, vol. 193, No. 11, pp. 1285-1294, Jun. 4, 2001.
Kakolyris, S, et al., "First-line treatment of metastatic breast cancer with mitoxantrone, vinorelbine, and carboplatin." Am J. Clin Oncol. Dec. 1999;22(6):568-72.
Kakolyris, S., et al., "A dose-escalation study of oxaliplatin and vinorelbine in patients with advanced solid tumors." Onocology. 2002;63(3):213-8.
Kanai et al. (1996) J. Immunol. 157:3681-3687.
Kapustra et al., "A Plant-Derived Edible Vaccine Against Hepatitis B Virus," The FASEB Journal, vol. 13, Oct. 1999, pp. 1796-1799.
Keimowitz, "Dementia Improvement With Cytotoxic Chemotherapy: A Case of Alzheimer Disease and Multiple Myeloma," Archives of Neurology, vol. 54, No. 4, pp. 485-488, Apr. 1997.
Kelly, W.K, et al., "Paclitaxel, estramustine phosphate, and carboplatin in patients with advanced prostate cancer." J. Clin Oncol. Jan. 1, 2001;19(1):44-53.
Kikuyama, S., et al. "Phase II study of mitomycin C, cisplatin and 5-fluorouracil for advanced and recurrent gastric cancer." Anticancer Res. Nov.-Dec. 2002;22(6B):3633-6.
Kilby, J. Michael MD et al.; Recurrence of the Acute HIV Syndrome After Interruption of Antiretroviral Therapy in a Patient with Chronic HIV Infection: A Case Report; Sep. 19, 2000; pp. 435-438; V. 133(6); Annals of Internal Medicine; American College of Physicians.
Kim, et al., "Dynamics and Potential Impact of the Immune Response to Chronic Myelogenous Leukemia," PLoS Computational Biology, 2008, vol. 4, Iss. 6, 17 pages.
Kim, LW., et al. "Phase II study of capecitabine plus cisplatin as first-line chemotherapy in advanced gastric cancer" Ann On col. Dec. 2002:13(12):1893-8.
Kimura, Motohiko, et al., "Significance of Serum Amyloid A on the Prognosis in Patients with Renal Cell Carcinoma" Cancer 2001; 92:2072-5.
Kindler HL, et al., "Edatrexate (10-ethyl-deaza-aminopterin)(NSC #626715) with or without leucovorin rescue for malignant mesothelioma. Sequential phase II trials by the cancer and leukemia group B." Cancer. 199 Nov. 15;86(10):1985-91.
Kinter et al., "CD25+ CD4+ Regulatory T Cells from the Peripheral Blood of Asymptomatic HIV-infected individuals Regulate CD4+

(56) References Cited

OTHER PUBLICATIONS and CD8+ HIV-specific T Cell Immune Responses in vitro and are associate with favorable clinical markers of disease status", Journal of Experimental Medicine, vol. 200, No. 3, pp. 331-343, Aug. 2, 2004.
Kinter et al., "CD25+ Regulatory T Cells Isolated from IV-Infected Individuals Suppress the Cytolytic and Nonlytic Antibiral Activity of HIV-Specific CD8+ T Cells in Vitro," AIDS Research and Human Retroviruses, vol. 23, No. 3, pp. 438-450, 2007.
Kinter et al., "Suppression of HIV-specific T cell activity by lymph node CD25+ regulatory T cells from HIV-infected individuals", PNAS, vol. 104, No. 9, pp. 3390-3395, Feb. 27, 2007.
Kjorstad, K., et al., "A multicenter phase II study of carboplatin in advanced ovarian carcinoma: final report" Ann Oncol. Mar. 1992;3(3):217-22.
Knoechel et al., "Sequential development of interleukin 2-dependent effector and regulatory T cells in response to endogenous systemic antigen", JEM, vol. 202, Nov. 21, 2005, 12 pages.
Kohm, et al., "CD4+ CD25+ Regulatory T Cells Suppress Antigen-Specific Autoreactive Immune Responses and Central Nervous System Inflammation During Active Experimental Autoimmune Encephalomyelitis," The Journal of Immunology, vol. 169, No. 9, pp. 4712-4716, Nov. 1, 2002.
Kollmannsberger, C., et al. "A phase II study of paclitaxel, weekly, 24-hour continuous infusion 5-fluorouracil, folinic acid and cisplatin in patients with advanced gastric cancer." Br. J. Cancer. Aug. 2000;83(4):458-62.
Kornek, G. V., et al. Effective combination chemotherapy with paclitaxel and cisplatin with or without human granulocyte colony-stimulating factor and/or erythropoietin in patients with advanced gastric cancer. Br. J. Cancer. Jun. 17, 2002; 86(12):1858-63.
Kornek, G. V.,et al., "Effective treatment of advanced breast cancer with vinorelbine, 5-fluorouracil and 1-leucovorin plus human granulocyte colony-stimulating factor." Br. J. Cancer. Sep. 1998;78(5):673-8.
Kosmas, C., et al. Phase I-II study of docetaxel and ifosfamide combination in patients with anthracycline pretreated advanced breast cancer. Br J Cancer, Apr. 22, 2003;88(8):1168-74.
Kouroussis, C., et al. Oxaliplatin in combination with infusional 5-fluorouracil and leucovorin every 2 weeks as first-line treatment in patients with advanced colorectal cancer: a phase II study. Oncology. 2001;61(1):36-41.
Kruse et al., "Analysis of Interleukin 2 and Various Effector Cell Populations in Adoptive Immunotherapy of 9L Rat Gliosarcoma: Allogeneic Cytotoxic T Lymphocytes Prevent Tumor Taken," Proc. Natl. Acad. Sci, USA, vol. 87, pp. 9577-9581, Dec. 1990.
Kukreja, et al., "Autoimmunity and Diabetes," The Journal of Clinical Endocrinology & Metabolism, vol. 84, No. 12, pp. 4371-4378, Dec. 1999.
Lage et al. "New insights on how nucleotide excision repair could remove DNA adducts induced by chemotherapeutic agents and psoralens plus UV-A (PUVA) in *Escherichia coli* cells." Mutation Research/Reviews in Mutation Research, Nov. 2003, vol. 544, No. 2-3, pp. 143-157 (Abstract Only).
Leung, T. W., et al., "Complete pathological remission is possible with systemic combination chemotherapy for inoperable hepatocellular carcinoma" Clin Cancer Res. Jul. 1999; 5(7):1676-81.
Lewis "Oxidative stress: the role of cytochromes P450 in oxygen activation," Journal of Chemical Technology and Biotechnology, Oct. 2002, vol. 77, No. 10, pp. 1095-1100 (Abstract Only).
Li, J. D., et al. "[Phase II clinical study of topotecan hydrochloride in patients with recurrent advanced ovarian cancer]" Ai Zheng. Apr. 2002;21(4):416-20.
Liang et al., "Murine AIDS, a key to understanding retrovirus-induced immunodeficiency" ViralImmunol1996, 9 (4):225-239; Abstract only. PMID: 8978019; PubMed, Indexed for Medline.
Lifson. Jeffrey D. et al., Containment of Simian Immunodeficiency Virus Infection: Cellular Immune Responses and Protection from Rechallenge following Transient Postinoculation Antiretroviral Treatment; Mar. 2000; DP. 2584-2593; V. 74. No. 6; Journal of Virology: American Society of Microbiology.
Lim et al., "Cell surface markers of regulatory T cells are not associated with increased forkhead box p3 expression in blood CD4+ T cells from HIV-infected patients responding to antiretroviral therapy", Immunology and Cell Biology, 2006, 84, 530-536.
Lim et al., "Proportions of circulating T cells with a regulatory cells phenotype increase with HIV-associated immune activation and remain high on antiretroviral therapy," AIDS 2007, vol. 21, pp. 1525-1534.
Lissoni, A., et al. "Phase II study of paclitaxel as salvage treatment in advanced endometrial cancer" Ann Oncol., Oct. 1996;7(8):861-3.
Little et al., "Systemic chemotherapy for HIV-associated lymphoma in the era of highly active antiretroviral therapy," Current Opinion in Oncology, Vo 12 No. 5, pp. 438-444 (Sep. 2000).
Liuzzo, et al. The Prognostic Value of C-Reactive Protein and Serum Amyloid A Protein in Servere Unstable Angina, The New England Journal of Medicine, vol. 331(7) Aug. 18, 1994.417-424.
Logothetis. Christopher J .. et al., "Cyclic Chemotherapy with Cyclophosphamide. Doxorubicin, and Cisplatin Plus Vinblastine and Bleomycin in Advanced Germinal tumors" Aug. 1986 The American Journal of Medicine. vol. 81. p. 219-227 XP-002351698.
Lori et al., "Hydroxyurea and HIV: 5 years later—from antiviral to immune-modulating effects", AIDS (London, England) Aug. 20, 1999, vol. 13, No. 12, pp. 1433-1442.
Lori et al., "Targeting HIV Reservoirs and reconstituting the immune system", AIDS research and human Retroviruses, vol. 15, No. 18, 1999, pp. 1597-1617.
Lorusso, P., et al., Low-dose continuous infusion 5-fluorouracil and cisplatin: phase II evaluation in advanced colorectal carcinoma. Am J Clin Oncol. Dec. 1989;12(6):486-90.
Lotem, M., et al., "Interleukin-2 improves tumour response to DNP-modified autologous vaccine for the treatment of metastatic malignant melanoma" British Journal of Cancer (2004) 90, 773-780.
Louvet C., et al. "Phase II study of oxaliplatin, fluorouracil, and folinic acid in locally advanced or metastatic gastric cancer patients" J. Clin Oncol. Dec. 1, 2002;20(23):4543-8.
Lundholm, Peter, "Immune and Autoimmune Responses to HIV-1 in Mucosa and Other Tissues" The Swedish Institute for Infectious Disease Control, Oct. 29, 1999, kl 9.00.
Lutsiak, M. E. Christine, et al, Inhibition of CD4+25+ T Regulatory Cell Function Implicated in Enhanced Immune Response by Low Dose Cyclophosphamide, Blood 1st Ed paper, pre published online Dec. 19, 2004; DOI 10.1182/blood-2004-06-2410.
Mahmoud et al., "The Role of C-Reactive Protein as a Prognostic Indicator in Advanced Cancer," Current Oncology Reports 2002 4:250-255.
Manetta A., et al., "Cyclosporin enhancement of cisplatin chemotherapy in patients with refractory gynecologic cancer. A Gynecologic Oncology Group Study." Cancer. Jan. 1, 1994;73(1):196-9.
Marchand. Marie. at el., "Tumor Regressions Observed in Patients with Metastatic Melanoma Treated with an Antigenic Peptide Encoded by Gene Mage-3 and Presented by HLA•A" XP-002305439 International Journal of Cancer, New York, NY, vol. 80, No. 2, Jan. 19, 1999, pp. 219-230.
Mariotta, S., et al., "Combined treatment in advanced stages (IIIb-IV) of non-small cell lung cancer." Eur Rev Med Pharmacol Sci. Mar.-Jun. 2002;6(2-3):49-54.
Mason et al., "Expression of Norwalk Virus Capsid Protein in Transgenic Tobacco and Potato and its Oral Immunogenicity in Mice," Proc. Natl. Acad. Sci. USA, vol. 93, pp. 5335-5340, May 1996.
Mbidde, E.K., et al., "Phase II trial of carboplatin (JM8) in treatment of patients with malignant mesothelioma." Cancer Chemother Pharmacol. 1986; 18(3):284-5.
McClay, E. F., et al., "A Phase II trial of intraperitoneal high-dose carboplatin and etoposide with granulocyte macrophage-colony stimulating factor support in patients with ovarian carcinoma." Am J. Clin Oncol. Feb. 1995;18(1 ):23-6.
McGuirk, Peter et al.; Pathogen-Specific Regulatory T Cells Provoke a Shift in the Th1/Th2 Paradigm in Immunity to Infectious Diseases; Sep. 2002; pp. 450-455; V. 23 No. 9; Trends in Immunology; Elsevier Science Ltd.

(56) References Cited

OTHER PUBLICATIONS

McMillan et al. Disease of the Colon & Rectum 1997; 40: 1068-1071.
McMillan et al. The American Journal of Surgery 1995, 170:319-322.
Medline Abstract Accession No. PMID 10228499; Aversa, S.M., et al.; Tumori; Jan.-Feb. 1999,85(1),54-59.
Medline Abstract Accession No. PMID 10950369; Dezube, B.J.; Semin Oneal; Aug. 2000,27(4),424-430.
Medline Abstract Accession No. PMID 8959247; Zanussi, S., et al.; AIDS Res Hum Retroviruses; Dec. 10, 1996; 12(18), 1703-1707.
Medstrand et al., "Characterization of Novel Reverse transcriptase encoding human endogenous retroviral sequences similar to type A and type B retroviruses: Differential transcription in normal human tissues", Journal of Virology, Nov. 1993, vol. 67, No. 11, pp. 6778-6787.
Mehigan et al. Changes in T cell subsets, interleukin-6, and C-reactive protein after laparoscopic and open colorectal resection for malignancy, Surg. Endosc. 2001; 15:1289-1293.
Melchior. J. et al., "Malnutrition and Wasting, Immunodepression, and Chronic Inflammation as Independent Predictors of Survival in HIV-Infected Patients", Nutrition, Nov.-Dec. 1999, vol. 15, No. 11/12, pp. 865-869.
Melichar, et al., "The Peripheral Blood Leukocyte Phenotype in Patients with Breast Cancer: Effect of Doxorubicin/Paclitaxel Combination Chemotherapy," Immunopharmacology and Immunotoxicology, 2001, vol. 23, No. 2, pp. 163-173.
Meropol, N. J., et al. "Phase II study of oral eniluracil, 5-fluorouracil, and leucovorin in patients with advanced colorectal carcinoma." Cancer. Apr. 1, 2001;91(7):1256-63.
Michelotti, A., et al., "Paclitaxel in combination with venorelbine in pretreated advanced breast cancer patients." Semin Oncol. Oct. 1996;23(5 SupplII):38-40.
Miller et al., "Human immunodeficiency virus and AIDS: insights from animal lentiviruses" J Virol 2000, 74 D (16):7187-7195.
Ming, Meng et al., "Studies on Development of Treatment against Retroviruses," Journal of Hebei Occupational Institute of Medical Science, 1997, No. 1, pp. 22-25.
Miyazono et al. "Surgical Maneuvers Enhance Molecular Detection of Circulating Tumor Cells During Gastric Cancer Surgery", Annals of Surgery 2001, 233: 189-194.
Modelska et al., "Immunization Against Rabies With Plant-Derived Antigen," Proc. Natl. Acad. Sci. USA, vol. 95, pp. 2481-2485, Mar. 1998.
Monnet I., et al., "Intrapleural infusion of activated macrophages and gamma-interferon in malignant pleural mesothelioma: a phase II study." Chest. Jun. 2002;121('):1921-7.
Monsonego, et al., "Immunotherapeutic Approaches to Alzheimer's Disease," Science, vol. 302, pp. 834-838, Oct. 31, 2003.
Montgomery et al., "Heterologous and Homologous Protection Against Influenza A by DNA Vaccination: Optimization of DNA Vectors," DNA and Cell Biology, vol. 12, No. 9, 1993, pp. 777-783.
Moore, John P. et al.; MiniReview Genetic Subtypes. Humoral Immunity. and Human Immunodeficiency Virus Type 1 Vaccine Development; Jul. 2001; pp. 5721-5729; V. 75, No. 13; Journal of Virology; American Society for Microbiology.
Morabito A., et al., "The combination of gemcitabine and vinorelbine is an active regimen as second-line therapy in patients with metastatic breast cancer pretreated with taxanes and or anthracyclines: a phase I-II study." Breast Cancer Res Treat. Mar. 2003; 78(li:29-36.
Morgan, et al., "CD25+ Cell Depletion Hastens the Onset of Severe Disease in Collagen-Induced Arthritis," Arthritis & Rheumatism, vol. 48, No. 5, pp. 1452-1460, May 2000.
Morris, M., et al., "Phase II study of vinorelbine in advanced and recurrent squamous cell carcinoma of the cervix" J. Clin Oncol. Mar. 1998;16(3):1094-8.
Morse et al., "Retrovirus-induced immunodeficiency in the mouse: MAIDS as a model for AIDS", AIDS, 1992, vol. 6, pp. 607-621.
Mortensen, "C-Reactive Protein, Inflammation, and Innate Immunity", Immunologic Research, 2001, vol. 24, No. 2, pp. 163-176.

Murad, A.M., "Phase II trial of the use of gemcitabine and 5-fluorouracil in the treatment of advanced pancreatic and biliary tract cancer." Am J Clin Oncol. Apr. 2003;26(2):151-4.
Murad, A.M., et al., "Phase II trial of the combination of paclitaxel and 5-fluorouracil in the treatment of advanced gastric cancer: a novel, safe, and effective regimen." Am J Clin Oncol. Dec. 1999;22(6):580-6.
Murphy, et al., "New strategies for preventing graft-versus-host disease," Current Opinion in Immunology, vol. 11, No. 5, pp. 509-515, Oct. 1, 1999.
Musk et al., "Conventional Treatment and its Effect on Survival of Malignant Pleural Mesothelioma in Western Australia," Aust. N.Z. J. Med. (1982) 12, pp. 229-232.
Nasti et al. "A risk and benefit assessment of treatment for AIDS-related Kaposi's sarcoma" Drug Safety, May 1999; 20(5):403-425.
Nathan F. E., et al., "Paclitaxel and tamoxifen: An active regimen for patients with metastatic melanoma" Cancer Jan. 1, 2000;88(1):79-87.
Neri B., "Results of leucovorin and doxifluridine oral regimen in the treatment of metastatic colorectal cancer" Anticancer Drugs. Aug. 1998;9(7):599-602.
Neri, B., et al. "Raltitrexed plus oxaliplatin as first-line chemotherapy in metastatic colorectal carcinoma: a multicentric phase II trial." Anticancer Drugs. Aug. 2002;13(7):719-24.
Nilsson, Jakob, et al., "HIV-1-driven regulatory T-cell accumulation in lymphoid tissues is associated with disease progression in HIV/AIDS" Blood, Dec. 1, 2006, vol. 108, No. 12 p. 3808-3817.
North, et al., "Generation and Decay of the Immune Response to a Progressive Fibrosarcoma," J. Exp. Med., May 1984, vol. 159, pp. 1295-1311.
North, R.J. and Awward, A. (1990) Elimination of cycling CD4 suppressor T cells with an anti-mitotic drug releases non-cycling CD8 T cells to cause regression of an advanced lymphoma. Immunology 71:90-95.
North, Robert J., "The Murine Antitumor Immune Response and Its Therapeutic Manipulation," Advances in Immunology, 1984, vol. 35, pp. 89-155.
Nystrom, M.I. et al. "Low-dose continuous chemotherapy for metastatic melanoma: a phase II trial" Melanoma Res. Apr. 2003;13(2):197-9.
O'Brien et al. "Changes in Plasma HIV-1 RNA and CD4+ Lymphocyte Counts and the Risk of Progression to AIDS." The New England Journal of Medicine, Feb. 15, 1996, vol. 334, No. 7, pp. 426-431.
O'Hanlon, Deirdre M. et al., "The Acute Phase Response in breast Carcinoma" Anticancer Research 22:1289-1294 (2002).
O'Hara, Rosemary, et al., "Acute-phase serum amyloid A production by rheumatoid arthritis synovial tissue" Arthritis Res 2000,2:142-144.
Okuno, S.H., et al., "Phase II study of methotrexate, vinblastine, doxorubicin, and cisplatin in patients with squamous cell carcinoma of the upper respiratory or alimentary passages of the head and neck" Cancer Apr. 15, 2002;94(8):2224-31.
Onizuka et al. "Tumor Rejection by in Vivo Administration of Anti-CD25 (Interleukin-2 Receptor a) Monoclonal Antibody", Cancer Research 1999; 59:3128-3133.
Orenstein R "Looking beyond highly active antiretroviral therapy: drug-related hepatotoxicity in patients with human immunodeficiency virus infection" Pharmacotherapy vol. 22(2002) pp. 1468-1478.
Ortiz, Gabriel M. et al.; HIV-1-Specific Immune Responses in Subjects Who Temporarily Contain Virus Replication After Discontinuation of Highly Active Antiretroviral Therapy, Aug. 16, 1999; V. 0, No. 1999; J. Clin Invest.; American Society for Clinical Investigation.
Österlund et al. "Raltitrexed treatment promotes systemic inflammatory reaction in patients with colorectal carcinoma," British Journal of Cancer, Sep. 2002, vol. 87, No. 6, pp. 591-599.
Ozols, RF., et al., "Phase II trial of 5-FU administered Ip to patients with refractory ovarian cancer." Cancer Treat Rep. Oct. 1984;68(10):1229-32.
Paccagnella, A., et al. "Mitomycin C., vinblastine, and carboplatin regimen in patients with nonsmall cell lung cancer. A phase II trial." Cancer. Oct. 15, 1996; 78(8):1701-7.

(56) References Cited

OTHER PUBLICATIONS

Patt, Y. Z., et al. "Phase II trial of systemic continuous fluorouracil and subcutaneous recombinant interferon Alfa-2b for treatment of hepatocellular carcinoma" J. Clin Oncol. Feb. 1, 2003; 21 (3):421-7.
Payelle B.. et al., "Role of T Suppressor Cells in the Cycling of the Immune Response Against a Murine Fibrosarcoma", International Journal of Cancer. Jul. 15, 1984, vol. 34, No. 1, pp. 95-100.
Pectasides, D., et al. "First line combination chemotherapy with docetaxel and vinorelbine in advanced breast cancer. A phase II study." Anticancer Res. Sep.-Oct. 2001;21(5):3575-80.
Pepys, et al., "C-reactive protein: a critical update," The Journal of Clinical Investigation, vol. 111, No. 12, pp. 1805-1812, Jun. 2003.
Perng, R P., et al. "A phase II trial of vinorelbine and cisplatin in previously untreated inoperable non-small-cell lung cancer." Am J Clin Oncol. Feb. 2000;23(1):60-4.
Peterson, Karin E., et al., "Novel Role of CD8+ T Cells and Major Histocompatibility Complex Class I Genes in the Generation of Protective CD4+ Th1 Responses during Retrovirus Infection in Mice" Journal of Virology, Aug. 2002, vol. 76, No. 16, O. 7942-7948.
Petrelli, NJ, et al. "Combination chemotherapy of cisplatin and 5-fluorouracil for advanced colorectal adenocarcinoma" Cancer Chemother Pharmacol. 1989;23(1 ):57-60.
Picus J., et al., "Docetaxel (Taxotere) as monotherapy in the treatment of hormone-refractory prostate cancer: preliminary results" Semin Oncol. Oct. 1999;26(5 Suppl17):14-8.
Pinto C., et al., "Combination chemotherapy with mitoxantrone, methotrexate, and mitomycin (MMM regimen) in malignant pleural mesothelioma: a phase II study." Am J Clin Oncol. Apr. 2001; 24(2):143-7.
Plana, M. et al. (2000) Immunological benefits of antiretroviral therapy in very early stages of asymptomatic chronic HIV-1 infection. AIDS 14:1921-1933. See abstract, Introduction 1st paragraph, Materials and Methods and last paragraph of the Discussion.
Planner R. S., et al., "Paclitaxel (Taxol) as salvage therapy for relapsed ovarian cancer" Aust N. Z. J. Obstet Gynaecol. May 1996; 36(2):168-70.
Planting A.S., et al., "Phase II study of a short course of weekly high-dose cisplatin combined with long-term oral etoposide in pleural mesothelioma" Ann Oncol. Jul. 1995:6(6): 613-5.
Pohl, J., et al., "Systemic chemotherapy with epirubicin for treatment of advanced or multifocal hepatocellular carcinoma" Chemotherapy. Sep.-Oct. 2001; 47(5)359-65.
Porta C., et al., "5-Fluorouracil and d,l-leucovorin calcium are active to treat unresectable hepatocellular carcinoma patients: preliminary results of a phase II study." Oncology, Nov.-Dec. 1995;52(6):487-91.
Posner, M., et al., "A phase II trial of continuous infusion cisplatin and 5-fluorouracil with oral calcium leucovorin in colorectal carcinoma" Am J. Clin Oncol. Jun. 1992; 15(3):239-41.
Price et al., "Development and Validation of a Particle-Enhanced Turbidimetric Immunoassay for C-reactive Protein," Journal of Immunological Methods, 99 (1987) 205-211.
Pyrhonen SO, et al., "Phase II study of epirubicin sequential methotrexate and 5-fluorouracil for advanced colorectal cancer" Eur J Cancer 1992;28A(II):1828-32.
Quevedo, et al., "Possible therapeutic reversal of immune suppression in patients with metastatic melanoma by timed delivery of temozolomide chemotherapy: A pilot study," Journal of Clinical Oncology, 2009, vol. 27, No. 155 (May 20 supplement), e20013.
Racke et al., "Intravenous Antigen Administration as a Therapy for Autoimmune Demyelinating Disease", Annals of Neurology, vol. 39, No. 1, pp. 46-56, 1996.
Raghavan D, et al., "Phase II trial of carboplatin in the management of malignant mesothelioma" J Clin Oncol. Jan. 1990;8(1):151-4.
Rakowicz-Szulczynska, Eva M. et al.; Human Immunodeficiency Virus Type 1-Like DNA Sequences and Immunoreactive Viral Particles with Unique Association with Breast Cancer; Sep. 1998; pp. 645-653; V. 5, No. 5; Clinical and Diagnostic Laboratory Immunology; American Society for Microbiology.
Rakowicz-Szulczynska, Eva M.; Relevance of the Viral RAK Alpha Gene in Diagnosis of Malignant Versus Nonmalignant Tumors of the Ovary and Uterus; May 2000; pp. 360-365; V. 7, No. 3; Clinical and Diagnostic Laboratory Immunology; American Society for Microbiology.
Read et al., "CD4+ regulatory T cells" Curr Opin Immunol 2001, 13:644-649.
Read, Simon, et al., "Cytotoxic T Lymphocyte-associated Antigen 4 Plays an Essential role in the Function of CD25+CD4+ Regulatory Cells that control Intestinal Inflammation," J. Exp. Med. The Rockefeller University Press vol. 192, No. 2, Jul. 17, 2000 295-302.
Recchia F, et at "Gemcitabine, ifosfamide and vinorelbine in advanced non-small cell lung cancer: a phase II study" Anticancer Res. Mar.-Apr. 2002;22(2B):1321-8.
Reina JJ, et al., "A multicenter phase II study of irinotecan (CPT-11) alternated with 5-fluorouracil and leucovorin as first-line treatment of patients with metastatic colorectal cancer" cancer chemother Pharmacol. Oct. 2003;52141:339-45. Eoub Jul. 8, 2003.
Retsas S, et al, "Taxol and venorelbine: a new active combination for disseminated malignant melanoma" Anticancer Drugs, Feb. 1996; 7(2):161-5.
Rodriguez-Galindo C, et al., "Treatment of refractory osteosarcoma with fractionated cyclophosphamide and etoposide" J Pediatr Hematol Oncol. May 2002;24(4):250-5.
Romero A 0, "Double modulation of 5-fluorouracil by methotrexate and high-dose L-leucovorin in advanced colorectal cancer" Am J Clin Oncol. Feb. 1998;21(1):94-8.
Romero A, et al., Vinorelbine as first-line chemotherapy for metastatic breast carcinoma J Clin Oncol, Feb. 1994;12(2):336-41.
Rose PG, et at, "A phase II study of docetaxel in paclitaxel-resistant ovarian and peritoneal carcinoma: a Gynecologic Oncology Group study" Gynecol Oncql. Feb. 2003;88(2):130-5.
Rosenthal MA, et al., "Phase II study of combination taxol and estramustine phosphate in the treatment of recurrent glioblastoma multiforme" J Neurooncol. Mar. 2000;47(1):59-63.
Rossi et al., "Inhibition of murine AIDS by a heterodinucleotide of azidothymidine and 9-(R)-2-(phosphonomethoxypropyl)adenine" J Antimicrobial Chemo 2002,50:639.
Rouse et al., "Regulatory T Cells in virus infections" Immunol Rev 2006, 212:272-286.
Safran H, et al., "Gemcitabine, paclitaxel, and radiation for locally advanced pancreatic cancer: a Phase II trial." Int J Radiat Oncol Bioi Phys. Sep. 1, 2002;54(1):137-41.
Sahni et al., "HIV Vaccine Strategies—an Update," Armed Forces Medical College, vol. 60, No. 2, 2004, pp. 157-164.
Sakaguchi et al., "Regulatory T cells: key controllers of immunologic self-tolerance" Cell 2000, 101 :455-458.
Sakaguchi, Shimon, et al., "Immunologic tolerance maintained by CD25+ CD4+ regulatory T cells: their common role in controlling autoimmunity, tumor immunity, and transplantation tolerance" vol. 182, Aug. 2001, pp. 18-32.
Sakata Y, et al. "Late phase II study of novel oral fluoropyrimidine anticancer drug S-1 (1 M tegafur-0.4 M gimestat-1 M otastat potassium) in advanced gastric cancer patients." Eur J Cancer. Oct. 1998;34(11 :1715-20.
Salomon et al., "B7/CD28 Costimulation is Essential for the Homeostasis of the CD4+ CD25+ Immunoregulatory T Cells that Control Autoimmune Diabetes," Immunity, vol. 12,431-440, Apr. 2000.
Santamaria, "Effector lymphocytes in autoimmunity," Current Opinion in Immunology, vol. 13, No. 6, pp. 663-669, Dec. 1, 2001.
Savarese 0, et al., "A phase II study of docetaxel (Taxotere), estramustine, and low-dose hydrocortisone in men with hormone-refractory prostate cancer: preliminary results of cancer and leukemia group B Trial 9780" Semin Oncol. Oct. 1999;26(5 Suppl17):39-44.
Savarese OM, et al. Phase II study of docetaxel, estramustine, and low-dose hydrocortisone in men with hormone-refractory prostate cancer: a final report of CALGB 9780. Cancer and Leukemia Group B. J Clin Oncol. May 1, 2001;19(9):2509-16.
Sawamura, M., et al., "Cyclic Haemopoiesis at 7- or 8-day Intervals", British Journal of Haematology, 88:215-18 (1994).

(56) References Cited

OTHER PUBLICATIONS

Scheithauer, W., et al. "Intermittent weekly high-dose capecitabine in combination with oxaliplatin: a phase I/II study in first-line treatment of patients with advanced colorectal cancer" Ann Oncol. Oct. 2002;13(10):1583-9.

Schornagel JH, et al., "Phase II study of recombinant interferon alpha-2a and vinblastine in advanced renal cell carcinoma" J Urol. Aug. 1989;142(2 Pt 1):253-6.

Sedegah et al., "Protection Against Malaria by Immunization With Plasmid DNA Encoding Circumsporozoite Protein," Proc. Natl. Acad. Sci., vol. 91, pp. 9866-9870, Oct. 1994.

Sehouli, J., et al., "A phase II study of topotecan plus gemcitabine in the treatment of patients with relapsed ovarian cancer after failure of first-line chemotherapy" Ann Oncol. Nov. 2002;13(11):1749-55.

Senju, Osamu, "Latex Agglutination Photometric Assay (LA-System)" JJCLA vol. 8, No. 1, 1983, p. 161-165.

Shepherd FA et al. "Combination chemotherapy and a-interferon in the treatment of Kaposi's sarcoma associated with acquired immune deficiency syndrome" CMAJ 139 (1988):635-639.

Sherman WH, et al., "Combination gemcitabine and docetaxel therapy in advanced adenocarcinoma of the pancreas." Oncology. 2001;60(4):316-21.

Shih et al., "Detection of Multiple, Novel Reverse Transcriptase Coding Sequences in Human Nucleic Acids: Relation to Primate Retroviruses," Journal of Virology, Jan. 1989, vol. 63, No. 1, pp. 64-75.

Shimizu et al., "Stimulation of CD25+ CD4+ Regulatory T Cells Through GITR Breaks Immunological Self-Tolerance," Nature Immunology, vol. 3, No. 2, Feb. 2002, pp. 135-142, http://Immunol.nature.com.

Shimizu J, et al. "Induction of tumor immunity by removing CD25+CD4+ T cells: a common basis between tumor immunity and autoimmunity" J Immunol. Nov. 15, 1999; 163(10):5211-8.

Simpson, et al., "Cell-Mediated Response to Tumour Xenografts in Mice," International Journal of Cancer, Mar. 1972, vol. 9, No. 2, pp. 299-304.

Sinnige, H. A., et al. "Modification of 5-fluorouracil activity by high-dose methotrexate or leucovorin in advanced colorectal carcinoma" Eur J Cancer. 1990;26(5):625-8.

Small EJ, et al., "Docetaxel, estramustine, plus trastuzumab in patients with metastatic androgen-independent prostate cancer" Semin Oncol. Aug. 2001; 28(4 Suppl15):71-6.

Smith, et al., "Use of Two-Dimensional Gel Electrophoresis to Measure Changes in Synovial Fluid Proteins from Patients with Rheumatoid Arthritis Treated with Antibody to CD4," Clinical and Diagnostic Laboratory Immunology, vol. 8, No. 1, pp. 105-111, Jan. 2001.

Smithers, Mark, et al., "Clinical response after intradermal immature dendritic cell vaccination in metastatic melanoma is associated with immune response to particulate antigen" Cancer Immunol Immunother (2003) 52: 41-52.

Sobrero AF, et al., "Schedule-selective biochemical modulation of 5-fluorouracil: a phase II study in advanced colorectal cancer" Clin Cancer Res, Sep. 1995; 1(9):955-60.

Speiser, et al., "TNF Receptor p55 Controls Early Acute Graft-Versus-Host Disease," The Journal of Immunology, vol. 158, No. 11, pp. 5185-5190, Jun. 1, 1997.

Stathopoulos GP, et al., Phase II trial of biweekly administration of vinorelbine and gemcitabine in pretreated advanced breast cancer, J Clin Oncol. 2002.

Stott. J. et al.; Candidate Vaccines Protect Macaques Against Primate Immunodeficiency Viruses; 1998; pp. S-265-S-270; V. 14. Suppl. 3; AIDS Research and Human Retroviruses; Mary Ann Liebert. Inc.

Sugimachi, K., et al., A phase II trial of a new 5-fluorouracil derivative, BOF-A2 (Emitefur), for patients with advanced gastric cancer. Surg Today. 2000; 30(12):1067-72 (abstract only).

Suri-Payer et al., "Differential Cytokine Requirements for Regulation of Autoimmune Gastritis and Colitis by CD4+ CD25+ T Cells," Journal of Autoimmunity (2001) 16, 115-123.

Sun-Payer et al., "CD4+CD25+ T Cells Inhibit Both the Induction and Effector Function of Autoreactive T Cells and Represent a Unique Lineage of Immunoregulatory Cells," The Journal of Immunology, vol. 160, pp. 1212-1218, D Feb. 1998.

Susumu et al. "Involvement of lipid peroxidation in the alteration of protein kinase c signaling." Acta Histochemica et Cytochemica, 2003, vol. 36, No. 4, pp. 281-285 (Abstract Only).

Sutmuller et al., "Synergism of Cytotoxic T Lymphocyte-associated Antigen 4 Blockade and Depletion of CD25+ Regulatory T Cells in Antitumor Therapy Reveals Alternative Pathways for Suppression of Autoreactive Cytotoxic T Lymphocyte Responses," J. Exp. Med. vol. 194, No. 6. Sep. 17, 2001. 823-832, http://www.jem.org/cgUcontentlfulll194/6/823.

Sutton GP, et al., A phase II trial of ifosfamide and mesna in patients with advanced or recurrent mixed mesodermal tumors of the ovary previously treated with platinum-based chemotherapy: a Gynecologic Oncology Group study. Gynecol Oncol. Apr. 1994; 5311\:24-6.

Takahashi et al., "Immunologic Self-Tolerance Maintained by CD25+CD4+ Regulatory T Cells Constitutively Expressing Cytotoxic T Lymphocyte-Associated Antigen 4," J. Exp. Med . vol. 192. No. 2. Jul. 17, 2000.303-309. http://www.jem.org/cgilcurrentifull/192121303.

Takahashi, Takeshi; Immunologic Self-Tolerance Maintained by CD20 CD4' Naturally Anergic and Suppressive T Cells: Induction of Autoimmune Disease by Breaking Their Anergic/Suppressive State; Sep. 10, 1998; DO. 1969-1980; V. 10, No. 12; International Immunology; Japanese Society for Immunology.

Takeuchi S., et al. [A late phase II study of CPT-11 on uterine cervical cancer and ovarian cancer. Research Groups of CPT-11 in Gynecologic Cancers] Gan To Kagaku Ryoho. Aug. 1991;18(10):1681-9.

Tan et al., "Evaluation of natural products as inhibitors of human immunodeficiency virus type 1 (HIV-1) reverse transcriptase" Journal of Natural Products, vol. 54, No. 1, 1991, pp. 143-154.

Tawa. A. et al., "Rhabdomyosarcoma of the Urinary Bladder. Complete remission induced by Vinblastine. cis-platinum. and Bleomycin" XP.o02351700 Gan to Kagaku Ryoho Japan. Dec. 1982.

Thomas, G.W., et al., Vincristine with high-dose etoposide in advanced breast cancer: a phase II trial of the Piedmont Oncology Association. Cancer Chemother Pharmacol. 1994;35(2):165-8.

Toniatti, C., et al., Regulation of the Human C-Reactive Protein Gene A Major Marker of Inflammation and Cancer. XP-002351697. 1990. Molecular Biology and Medicine. vol. 7. No. 3. 1990. pp. 199-212.

Trefzer, Uwe, et al., "Vaccination with Hybrids of Tumor and Dendritic Cells Induces Tumor-Specific T-Cell and Clinical Responses in Melanoma Stage III and IV Patients" Int. J. Cancer: 110,730-740 (2004).

Trivedi C., et al., Weekly 1-hour infusion of paclitaxel. Clinical feasibility and efficacy in patients with hormone-refractory prostate carcinoma. Cancer, Jul. 15, 2000;89(2):431-6.

Trudeau et al. "Prediction of spontaneous autoimmune diabetes in NOD mice by quantification of autoreactive T cells in peripheral blood," The Journal of Clinical Investigation, Jan. 2003, vol. 111, No. 2, pp. 217-223.

Tsavaris N, et al., Combination chemotherapy with cisplatin and/or doxorubicin in malignant mesothelioma. A retrospective study [corrected from prospective]. Anticancer Res. Sep.-Oct. 1997;17(5B):3799-802.

Twelves, CJ, et al., A phase II, multicentre, UK study of vinorelbine in advanced breast cancer. Br J Cancer Nov. 1994;70(5):990-3.

Ulmer et al., "Heterologous Protection Against Influenza by Injection of DNA Encoding a Viral Protein", Science. Mar. 19, 1993, vol. 259. No. 5102. pp. 1745 (5 pages).

Vahlenkamp et al., "Feline Immunodeficiency Virus infection phenotypically and functionally activates immunosuppressive CD4+CD25+ T Regulatory Cells", Journal of Immunology, 2004, pp. 4752-4761.

Vahlenkamp et al., "The role of CD4+ CD25+ regulatory T cells in viral infections", Veterinary immunology and Immunopathology, vol. 108, pp. 219-225, 2005.

Valdivieso M., et al., Broad phase II study of vindesine. Cancer Treat Rep. Sep.-Oct. 1981;65(9-1 0):877-9.

Verma, et al., "Role of MHC class I expression and CD8+ T cells in the evolution of iodine-induced thyroiditis in NOD-H2h4 and NOD mice," European Journal of Immunology, vol. 30, pp. 1191-1202, 2000.

(56) References Cited

OTHER PUBLICATIONS

Vila, et al., "Regulatory T cells and autoimmunity," Current Opinion in Hematology, 2009, vol. 16, Iss. 4, pp. 274-279.
Von Herrath Matihias et al., "Antigen-induced Regulatory T Cells in Autoimmunity", iNature Reviews. Immunology, Mar. 2003, vol. 3, No. 3, pp. 223-232.
Wang et al., "Detection of Mammary Tumor Virus ENV Gene-like Sequences in Human Breast Cancer", Cancer Research 55, 5173-5179, Nov. 15, 1995.
Wang et al., "Gene Inoculation Generates Immune Responses Against Human Immunodeficiency Virus Type 1," Proc. Natl. Acad. Sci. USA. vol. 90. pp. 4156-4160. May 1993.
Weinstein, P. S. et al., "Acute-Phase Proteins or Tumour Markers: The Role of SAA, SAP, CRP and CEA as Indicators of Metastasis in a Broad Spectrum of Neoplastic Disease" Scand. J. Immunol. 19, 193-198, 1984.
Weiss. Laurence, et al., "Human immunodeficiency virus—driven expansion of CD4+ CD25+ regulatory T cells. which suppress HIV-specific CD4 T-cell responses in HIV-infected patients" Blood. Nov. 15, 2004. vol. 104. No. 10 pp. 3249-3256.
Wittig. Burghardt. et al., "Therapeutic Vaccination against Metastatic Carcinoma by Expression-Modulated and Immunomodified Autologous Tumor Cells: A First Clinical Phase I/II Trial" Human Gene Therapy 12:267-278 (Feb. 10, 2001).
Wong et al., "Identification of an MHC class I-restricted autoantigen in type 1 diabetes by screening an organ-specific cdna library," Nature Medicine, vol. 5, No. 9, pp. 1026-1031, Sep. 17, 2002.
Wu, et al., "Tumor necrosis factor-x regulation of CD4+ CD25+ T cell levels in NOD mice," Proceedings of the National Academy of Sciences, vol. 99, No. 19, pp. 12287-12292, Sep. 17, 2002.
Xiang et al., "Vaccination with a Plasmid Vector Carrying the Rabies Virus Glycoprotein Gene Induces Protective Immunity Against Rabies Virus," Virology 199,132-140 (1994).
Yamada, Y, et al., "Phase II trial of paclitaxel by three-hour infusion for advanced gastric cancer with short premedication for prophylaxis against paclitaxel-associated hypersensitivity reactions" Ann Oncol. Aug. 12, 2001(18):1133-7.
Yang et al., "Early Studies on DNA-Based Immunizations for Measles Virus," Vaccine. vol. 15. No. 8, pp. 888-892.1997.
Yogelzang NJ, et al., Dihydro-5-azacytidine in malignant mesothelioma. A phase II trial demonstrating activity accompanied by cardiac toxicity. Cancer and Leukemia Group B. Cancer. Jun. 1, 1997;79(11 ):2237-42.
Yoon, et al., "Cellular and Molecular Pathogenic Mechanisms of Insulin-Dependent Diabetes Mellitus," Health Aging for Functional Longevity: Molecular and Cellular Interactions in Senescence, Annals of the New York Academy of Sciences, vol. 928, pp. 200-211, Apr. 2001.
Zeng, et al. Improved long-term survival for unresectable hepatocellular carcinoma (HCC) with a combination of surgery and intrahepatic arterial infusion of 131I-anti-HCC mAb. Phase I/II clinical trials. J Cancer Res Clin Oncol. 1998;124(5):275-80.
Zhang et al., "Studies on the Progress in the Development of AIDS Vaccines," Immunological Journal, vol. 16, No. 4, Jul. 2000, S72-74 (Abstract).
Zou et al. (1999) J. Acquir. Immune Defic. Syndr. 22:31-38.
Patent Cooperation Treaty, PCT International Search Report, dated Nov. 14, 2005, 4 pages.
International Search Report for International (PCT) Application No. PCT/AU2004/001456, mailed Dec. 8, 2004.
International Preliminary Report on Patentability for International (PCT) Application No. PCT/AU2004/001456, completed Sep. 27, 2005.
Written Opinion for International (PCT) Patent Application No. PCT/AU2004/001456, mailed Dec. 8, 2004.
Supplementary European Search Report for EP 03 70 1355, complete Dec. 5, 2005.
Supplementary Partial European Search Report, European Patent Office, dated Aug. 11, 2008, 8 pages.
Supplementary Partial European Search Report, dated Aug. 8, 2008, 8 pages.
European Examination Report, dated Jul. 9, 2008, 10 pages.
European Supplementary Search Report, dated Aug. 6, 2008, 6 pages.
Chinese Office Action for Patent Application No. 01817380—English Translation referencing Ming, Meng et al., Journal of Hebei Occupational Institute of Medical Science, 1997, No. 1, pp. 22-25.
Official Action for Australia Patent Application No. 2004283322, dated Jan. 13, 2010, 3 pages.
Request to Amend a Complete Specification, dated Jun. 22, 2010, in Australian Application No. 2004283322, 30 pages.
Official Action for Australia Patent Application No. 2004283322, dated Jul. 1, 2010, 3 pages.
Request to Amend a Complete Specification, dated Aug. 27, 2010, in Australian Application No. 2004283322, 27 pages.
Official Action (with English translation) for China Patent Application No. 2004800389993, dated Apr. 24, 2009, 9 pages.
Official Action for European Patent Application No. 04761461.5, dated Dec. 17, 2008, 7 pages.
Official Action for European Patent Application No. 04761461.5, dated Aug. 7, 2009, 8 pages.
Official Action for European Patent Application No. 04761461.5, dated Feb. 24, 2010, 15 pages.
Official Action for European Patent Application No. 04761461.5, dated Jul. 2, 2010, 29 pages.
Response, dated May 12, 2009, in European Application No. 04761461, 17 pages.
Response, dated Dec. 17, 2009, in European Application No. 04761461, 17 pages.
Written submissions, dated Apr. 19, 2010, in European Application No. 04761461, 129 pages.
Official Action (with English translation) for Japanese Patent Application No. 2006-535913, dated Oct. 25, 2010, 10 pages.
Official Action for Mexico Patent Application No. PA/a/2006/004522 dated May 18, 2009, 4 pages.
Official Action for Mexico Patent Application No. PA/a/2006/004522 dated Nov. 9, 2009, 2 pages.
Official Action for Mexico Patent Application No. PA/a/2006/004522 dated Mar. 23, 2010, 3 pages.
Response, dated Oct. 2, 2009, in Mexican Application No. PAa2006004522, 14 pages.
Response, dated Jan. 25, 2010, in Mexican Application No. PAa2006004522, 14 pages.
Response, dated Jul. 28, 2010, in Mexican Application No. PAa2006004522, 5 pages.
Official Action for New Zealand Patent Application No. 546873, dated Dec. 4, 2007, 2 pages.
Official Action for New Zealand Patent Application No. 546873, dated Sep. 30, 2009, 2 pages.
Official Action for New Zealand Patent Application No. 546873, dated Jan. 19, 2010, 2 pages.
Official Action for New Zealand Patent Application No. 546873, dated Jul. 5, 2010, 2 pages.
Response, dated Jun. 3, 2009, in New Zealand Application No. 546873, 43 pages.
Response, dated Jan. 5, 2010, in New Zealand Application No. 546873, 6 pages.
Response, dated Jun. 21, 2010, in New Zealand Application No. 546873, 42 pages.
Response, dated Jul. 28, 2010, in New Zealand Application No. 546873, 43 pages.
Official Action for Australia Patent Application No. 2005282218, dated Nov. 9, 2010, 3 pages.
Official Action for European Patent Application No. 05777835.9, dated Dec. 4, 2008, 1 page.
Response to Dec. 4, 2008 Official Action for European Patent Application No. 05777835.9, dated Sep. 22, 2009, 30 pages.
Official Action for European Patent Application No. 05777835.9, dated Dec. 17, 2009, 12 pages.
Response to Dec. 17, 2009 Official Action for European Patent Application No. 05777835.9, dated Oct. 8, 2010, 11 pages.

(56) References Cited

OTHER PUBLICATIONS

English Translation of Official Action for Japan Patent Application No. 2007-530544, mailed Aug. 9, 2011, 4 pages.
Summons to Oral Proceedings for European Patent Application No. 05777835.9, dated Jul. 6, 2011, 14 pages.
Response to Jul. 6, 2011 Summons to Oral Proceedings for European Patent Application No. 05777835.9, dated Oct. 3, 2011, 7 pages.
European Search Report and Search Opinion for European Patent Application No. 10180749, completed Jul. 11, 2011, 14 pages.
Official Action with English translation for Japan Patent Application No. 2006-535913, mailed Sep. 29, 2011, 4 pages.
Notice of Appeal with English translation for Japan Patent Application No. 2006-535913, dated Dec. 9, 2011, 15 pages.
Official Action for Canada Patent Application No. 2,543,490, dated Dec. 15, 2011, 7 pages.
Response to Dec. 29, 2011 Official Action for Canada Patent Application No. 2,543,490, dated Jun. 15, 2012, 31 pages.
Official Action for Canada Patent Application No. 2,543,490, dated Aug. 15, 2012, 6 pages.
European Search Report and Search Opinion for European Patent Application No. 10779928, dated Oct. 29, 2012, 4 pages.
Di Nicolantonio et al., "Cancer cell adaptation to chemotherapy," BMC Cancer, 2005, vol. 5, 16 pages.
Gajewski et al., "Gene Signature in Melanoma Associated With Clinical Activity: A Potential Clue to Unlock Cancer Immunotherapy," The Cancer Journal, 2010, vol. 16, Iss. 4, pp. 399-403.
Gottesman, "Mechanisms of Cancer Drug Resistance," Annual Review of Medicine, 2002, vol. 53, pp. 615-627.
Hosotsubo et al., "Hyperbilirubinaemia After Major Thoracic Surgery: Comparison Between Open-Heart Surgery and Oesophagectomy," Critical Care, 2000, vol. 4, No. 3, pp. 180-187.
Maury, et al., "Comparative study of serum amyloid-related protein SAA, C-reactive protein, and B2-microglobulin as markers of renal allograft rejection," Clinical Nephrology, 1984, vol. 22, No. 6, pp. 284-292.
Broom et al., "Interleukin 2 therapy in cancer: identification of responders," British Journal of Cancer, 1992, vol. 66, Iss. 6, pp. 1185-1187.
Dezube et al., "The Effect of Tenidap on Cytokines, Acute-Phase Proteins, and Virus Load in Human Immunodeficiency Virus (HIV)-Infected Patients: Correlation between Plasma HIV-1 RNA and Proinflammatory Cytokine Levels," The Journal of Infectious Diseases, 1997, vol. 176, Iss. 3, pp. 807-810.
Kamińska et al., "CRP, TNFα, IL-1ra, IL-6, IL-8 and IL-10 in blood serum of colorectal cancer patients," Pathology Oncology Research, 2000, vol. 6, Iss. 1, pp. 38-41.
Mollet et al., "Dynamics of HIV-Specific CD8+ T Lymphocytes with Changes in Viral Load," The Journal of Immunology, 2000, vol. 165, No. 3, pp. 1692-1704.

\* cited by examiner

COMPUTER SYSTEMS FOR TREATING DISEASES

CROSS-REFERENCE TO RELATED APPLICATIONS

This application is a Continuation of U.S. patent application Ser. No. 13/322,357, filed May 11, 2012; which is a national stage application under 35 U.S.C. §371 of PCT Application No. PCT/AU2010/000649 having an international filing date of May 27, 2010, which designated the United States, which PCT application claimed the benefit of U.S. Patent Application No. 61/181,508, filed on May 27, 2009, the entire disclosure of each of which are hereby incorporated by reference.

FIELD OF THE INVENTION

The present invention relates to computer-implemented methods and system for analysing a biomarker which cycles in a subject. In some other aspects, the present invention relates to analysing a biomarker which at least initially increases or decreases in amount in a subject following a treatment for a disease. In further aspects, the present invention relates to computer-implemented methods and systems for determining a preferred time to administer a therapy to treat a disease in a subject. The present invention also relates to computer program product to implement the methods. Further, the present invention relates to methods of determining the timing of treating a disease in a subject in which the immune system is cycling.

BACKGROUND OF THE INVENTION

Regulatory T Cells

Studies have identified the existence of a naturally occurring population of regulatory/suppressor T cells, which, upon in vitro TCR-mediated stimulation, suppress the proliferation of effector T cells (von Herrath and Harrison, 2003; Allan et al., 2008; Brusko et al., 2008; Vila et al., 2009). These cells are central to the control of T cell homeostasis and in the modulation of immune responses to autoantigens, cancer cells, pathogens, and alloantigens.

In the periphery of young mice not prone to autoimmune diseases, regulatory T cells constitute a stable 10% of $CD4^+$ T cells. This proportion appears to be reduced in mice genetically prone to autoimmune disease such as diabetes (Salomon et al., 2000). Transfer of regulatory T cells has been shown to prevent a wide range of experimental autoimmune diseases, including diabetes, experimental autoimmune encephalomyelitis, and colitis (Salomon et al., 2000; Wu et al., 2002; Kohm et al., 2002; Read et al., 2000). Furthermore, depletion of regulatory T cells has been shown to exacerbate various experimental autoimmune diseases, including collagen induced arthritis. In humans, an analogous population of $CD4^+CD25^+$ regulatory T cells has been identified in the peripheral blood and the thymus (Jonuliet et al., 2001; Annunziato et al., 2002).

Autoimmune Diseases

Many autoimmune disorders arise when cells of specific tissues become the targets of T lymphocytes (for reviews see Santamaria, 2001; Vila et al., 2009). Much of what is currently known about effector pathways of autoimmunity has been learned from spontaneous and experimental models of autoimmune disease. Type 1 diabetes mellitus (T1D) in non-obese diabetic (NOD) mice is a prototypic model of spontaneous, organ-specific autoimmunity. NOD mice spontaneously develop a form of autoimmune diabetes, closely resembling human T1D, that results from destruction of the pancreatic β-cells by T lymphocytes.

Studies of CD8+ T-cell-deficient NOD mice indicate that the initial β-cell insult in T1D is effected by cytotoxic CD8+ T cells. Several transgenic models of T1D have shown that CD8+ T cells can readily kill β-cells expressing transgenic neo-antigens; however, little is known about the antigenic specificity or specificities of the CD8+ T cells that kill β-cells in NOD mice. Wong et al. (1999) have reported that there is a CD8+ T-cell subpopulation that recognizes an insulin-derived peptide in the islets of young NOD mice. Furthermore, immunopathological studies of pancreata from human diabetic individuals and pancreas isograft recipients have suggested that destruction of β-cells in human T1D may also be effected, at least in part, by CD8+ effector T cells (Bottazzo et al., 1985).

Experimental autoimmune encephalomyelitis (EAE) is a prototypic experimental autoimmune disease that models human multiple sclerosis and that develops in susceptible rodent strains after immunization with myelin basic protein, proteolipid antigen or myelin oligodendrocyte protein (MOG). Evidence suggests that CD8+ T cells have a role in disease progression and severity (reviewed by Goverman, 1999). Myelin basic protein is processed in vivo by the MHC class I pathway, and a MOG-derived peptide activates encephalitogenic CD8+ T cells in vivo. There is also evidence for clonal expansions of CD8+ T cells in active multiple-sclerosis lesions (Babbe et al., 2000).

Graft-Versus-Host Disease

Graft-versus-host disease is a multistep process. It has been shown that effector T cells play the pivotal role in the induction of the disease. During the 'induction phase' the effector T cells see alloantigen disparities and then become activated and clonally expand (the 'expansion stage'). These T cells then release cytokines and possibly chemokines (for example macrophage inflammatory protein 1α), resulting in the recruitment of other cell types (macrophages, granulocytes, natural killer cells, etc.) in the 'recruitment phase'. Finally, the T cells and the other cell types mediate the pathology associated with graft-versus-host disease (the 'effector phase') (for a review see Murphy and Blazar, 1999).

There has been emphasis on delineating the effector mechanisms of graft-versus-host disease. T cells and other cells primarily mediate their effector functions through either FasL, perforin-granzyme-B or TNF. The use of knockout mice has demonstrated a pivotal role for each of these pathways in the effector stage of graft-versus-host disease. FasL and perforin-granzyme-B appear critical for solid organ pathology whereas TNF appears to mediate the wasting/weight loss associated with graft-versus-host disease. TNF also appears to be induced, along with other cytokines, after conditioning (Hill et al., 1997)—demonstrating that cytokines elicited by either the donor or the recipient affect graft-versus-host disease. TNF-receptor knockout mice and the use of anti-TNF antibodies have been shown to be protective in graft-versus-host disease models (Speiser et al., 1997).

Cancer

In the past, attempts have been made to trigger the immune system to mount an efficient response against malignant cells. Despite significant and promising progress, such a response has yet to be fully attained and many immune based therapies have proved disappointing.

Numerous studies using in vitro cellular assays demonstrate that cytotoxic lymphocytes have the ability to kill tumour cells. The cancer patient also has increased concentration of circulating immune complexes, indicating the immune system is active, particularly against certain tumour antigens. The level of these immune complexes can increase with disease progression (Horvath et al., 1982; Aziz et al., 1998).

Regulatory T cells have been implicated in a subject's immune response to cancer (North and Awwad, 1990; Gajewski et al., 2009). As most cancer antigens are actually produced by the patient they are considered as "self" by the immune system. Upon the presence, and/or increased quantity, of tumour antigen the host's immune system mounts a response characterized by the production of effector T cells which target cells producing the tumour antigen. However, in many instances these effector T cells are recognized by the immune system as targeting the host's own cells, and hence a population of regulator T cells are produced to down-regulate the effector T cell population. Thus, the production of these regulator T cells limits the ability of the immune system to effectively remove cancer cells.

Degenerative Diseases

Whilst degenerative diseases such as Alzheimer's disease are not classically considered to be mediated by inflammation or the immune system, in some instances the immune system may play an important role in the degenerative process. In addition, it has become clear that the immune system itself may have beneficial effects in nervous system diseases considered degenerative. Immunotherapeutic approaches designed to induce a humoral immune response have recently been developed for the treatment of Alzheimer's disease. In animal models, it has also been shown that immunotherapy designed to induce a cellular immune response may be of benefit in central nervous system injury, although T cells may have either a beneficial or detrimental effect depending on the type of T cell response induced (Monsonego and Weiner, 2003).

Infections

More recently, regulator T cells have been shown to be involved in a subject's immune response to a viral infection. WO 02/13828 describes the production of regulator T cells during retroviral infection, and methods of treating such infections by down-regulating the regulator T cell population whilst maintaining the effector T cell population. Since WO 02/13828 was filed there have been a large number of studies which have identified a role for regulatory T cells in the progression of chronic retroviral infections. This includes studies on Friend retrovirus infection (Iwashiro et al., 2001); Feline immunodeficiency virus (Vahlenkamp et al., 2004); Simian immunodeficiency virus (Hryniewicz et al., 2006; Estes et al., 2007) and many studies on HIV (Weiss et al., 2004; Kinter et al., 2004; Lim et al., 2006; Nilsson et al., 2006; Kinter et al., 2007a; Kinter et al., 2007b; Lim et al., 2007; Cao et al., 2009). The role of regulatory T cells in the progression of chronic retroviral infections has also been the subject of many recent reviews including those by Vahlenkamp et al. (2005), Belkaid and Rouse (2005), Rouse et al. (2006) and Dittmer (2004).

Treatment of Diseases Involving Effector and Regulator T Cells

Taking advantage of regulatory T cells has been complicated by an inability to expand and characterize this minor T cell subset, a population of cells reduced even further in autoimmune-prone animals and patients. For instance, studies have suggested that it may be impossible to reverse ongoing autoimmune diabetes due to the autoreactive T cells becoming resistant to suppression during the active phase of the disease. Prior efforts to expand regulatory T cells ex vivo have not achieved clinically sufficient expansion, nor demonstrable in vivo efficacy. The low number of CD4+CD25+ regulatory T cells, their anergic phenotype and diverse antigen specificity present major challenges to harnessing this potent tolerogenic population to treat autoimmune diseases and transplant rejection.

WO 03/070270 describes the use of acute phase inflammatory markers in regimes for the effective treatment of HIV. These methods rely on at least partially "resetting" the immune system by a treatment such as HAART followed by the analysis of acute phase inflammatory proteins as markers for effector and regulator T cell expansion. The emergence of acute phase inflammatory proteins appears to be linked to effector T cell expansion, which occurs before regulator T cell expansion, and thus the patient can be treated with a suitable agent which allows the effector T cell population to be maintained whilst destroying, preventing the production of, or reducing the activity of, regulator T cells. In essence, upon withdrawal of HAART treatment it was considered that the patient's immune system would treat the re-emerging HIV particles as a new infection, and hence a new population of effector T cells would be produced.

Similar to WO 03/070270, WO 03/068257 relates to at least partially resetting the immune system, however, in this instance in the context of the treatment of cancer. Again, the treatment is focussed on the initial re-emergence of effector T cells following a reduction in tumour load through techniques such as surgery or the administration of anti-proliferative drugs.

Following from the advances described in WO 02/13828, WO 03/070270 and WO 03/068257, it was later surprisingly found that the immune system is cycling in many chronic disease states such as cancer, retroviral infections (both in WO 05/040816) and autoimmune diseases (WO 06/026821). Thus, it is not essential that the disease state be "reset" to be able to target the regulator T cells to effectively treat the diseases involving regulator T cells such as cancer. Despite the ground breaking advances described in WO 05/040816 and WO 06/026821, variations between individuals, variations in sample testing, and the complexity of the disease states make it difficult to manage the data to allow the routine targeting of the desired cell type on the first attempt. Thus, there is a need for mechanisms to increase the likelihood of effectively treating a disease in which the immune system is cycling in the initial attempt(s).

SUMMARY OF THE INVENTION

According to a first aspect, the present invention provides a computer-implemented method for analysing a biomarker which cycles in a subject with a disease, the method comprising estimating a periodicity of the cycling of the biomarker based on measurements of the biomarker.

The method may further comprise determining from the estimated periodicity of the cycling a preferred time in the future to administer a therapy to treat the disease in the subject. The measurements of the biomarker may be received via a communications network, or retrieved from a remote or local storage.

Estimating the periodicity may comprise obtaining a best-fit curve to the measurements in accordance with a model of the cycling of the biomarker. The model of the periodicity of the cycling biomarker may in some embodiments be of the form:

$$\log(\text{marker}_i) = \cos(2\pi \times ((\text{time}_i - \text{offset})/(\text{period})) \times \text{amplitude} + \text{mean} + \epsilon_i$$

where $\text{marker}_i$ is a measurement taken at $\text{time}_i$, and parameters offset, period, amplitude, mean and model error or residual $\epsilon_i$ are unknown. Preferably, the model errors are normally distributed with zero mean and constant but unknown variance, or from one of the family of t distributions with degrees of freedom as determined by the model fitting mechanism.

For example, where the measurements are CRP measurements obtained with a time specificity of one day, the model may be of the form:

$$\log(CRP_i) = \cos\left(2\pi \times \left(\frac{day_i - \text{offset}}{\text{period}}\right)\right) \times \text{amplitude} + \text{mean} + \epsilon_i$$

where $CRP_i$ is a CRP measurement taken at $day_i$, and parameters offset, period, amplitude, mean and model error or residual $\epsilon_i$ are unknown.

The method may further comprise projecting the obtained best-fit curve into the future to determine the preferred time in the future to administer the therapy. The best-fit curve may be a fit to a harmonic model of the cycling of the biomarker. In this case, obtaining the best-fit curve further comprises fitting the harmonic model to the measurements multiple times using different initial conditions for each fit. For example where the harmonic model includes the period as a parameter, the initial value of the period may be altered for each fit so as to generate different best-fit results. In one embodiment, different initial estimates of cycle period, such as but not limited to, about 3 days, about 5 days, about 7 days or about 9 days. Where the curves so generated differ, reduced confidence in the best fit results can be inferred. This may include at least two, and preferably three curves under different regression models for the single set of data. In such embodiments a similarity or disparity of the best fit result of each regression model is preferably used to generate a confidence measure to indicate a confidence in the model having the highest log-likelihood Thus, in another embodiment, the method further comprises generating a confidence measure by comparing a similarity in a fit result produced by each fitting. Furthermore, in recognition of the difficulty of extracting a periodic characteristic from a small number of measurements, such as seven daily noisy measurements, such embodiments of the present invention provide not only a method of analysing such data in a manner to give an estimated best fit periodic curve, but also provide an indication of the confidence in the estimate.

Obtaining a best-fit curve may further comprise imposing a box constraint on at least some of parameters of the model to guide optimisation to biologically realistic regions. In some embodiments, an optimisation algorithm is repeatedly applied using altered levels of degrees of freedom, to allow for differing tolerance to data outliers. A fitted model with the highest log-likelihood may then be chosen for each initial condition for comparison to a fitted model obtained using an alternative nominated initial condition. In this case, close agreement between the chosen fitted models may be taken to improve a confidence in the estimate of the underlying cycle.

A variance-stabilizing transformation of the measurements may be determined prior to estimating the periodicity based on the transformed measurements. In taking a variance-stabilizing transformation of the measurements, the noisy nature of the biomarker measurements and the non-constant amplitude in the cycling biomarkers are considered.

Any suitable variance-stabilizing transformation of measurements may be used, such as logarithm of the measurements. The transformation taken may be the identity, the square root, the natural logarithm, the logarithm to base 10, any other transformation from the ladder of powers, or the like. The transformation will preferably be the natural logarithm and the exposition that follows will assume that this has been performed. Noting that at least some biomarkers, for example c-reactive protein (CRP) levels, are measured as a concentration, negative measurements are not possible so that the variance-stabilizing transformation can always be taken in such embodiments.

Determining the preferred time to administer the therapy may further comprise comparing the measurements of the subject with a database of measurements of the biomarker obtained from other subjects who had the disease and have been treated with a therapy. The therapy used to treat the "other subjects" may be the same or different to that which is planned to be administered to the subject, preferably the same. Furthermore, not all the "other subjects" may have been treated with the same therapy, for example, the exact same antiproliferative drug.

The measurements may also be for two or more different biomarkers which are cycling in the subject, in which case the method comprises determining the preferred timing of administration by reference to two or more sets of measurements. This may provide improved accuracy of estimation of immune system cycling as compared to embodiments which rely on measurements of a single biomarker. Alternatively or additionally, two or more different types of measurements are taken for the same biomarker. For example, daily or sub-daily measurements of an acute phase marker can be taken from a finger prick sample using a hand-held point of care monitoring device coupled with and calibrated by less frequent but more precise measurements obtained by detailed sample examination such as is provided by a professional laboratory.

The model may have a heavy tail to allow for noisy nature of the measurements, such as by applying non-linear regression using maximum likelihood and assuming a heavier-tailed error distribution. In this embodiment, T regression replaces the assumption of the normal distribution for the errors with the t distribution with statistically-determined degrees of freedom. The degrees of freedom correlate to the weight of the tail (more degrees gives lighter tail); heavier tails provide greater robustness to outlier values.

In another embodiment, the use of an error distribution is selected to provide robustness against extreme values, for example, the normal, the family of t distributions, the Cauchy, the gamma, the Weibull, and the Johnson S families, preferably the t family.

In cases where a periodic characteristic of the measurements cannot be determined or can only be estimated with low confidence, the method and algorithm preferably further provides for a recommendation that further samples be analysed. Preferably also provided is a recommendation for the preferred timing of measurements to help ensure the further monitoring provides sufficient data to characterize the cycling, such as the times that the several models that have been produced are at their furthest points from one another. Alternatively, an output indication is sent to a skilled operator to visually analyse the data and determine whether a preferred timing can be estimated through human intervention or whether the recommendation that further samples be analysed is sent to the end user.

In some embodiments, the method is carried out on-site at a testing facility at which the measurements are obtained from a diseased subject. In other embodiments, the method is carried out using a hand-held, generally point-of-care device, which is able to measure the biomarker, for example, a device which can measure acute phase inflammatory marker levels from a drop of blood obtained from a finger-prick. In alternative embodiments, the method is conducted at a central location remote from a testing facility.

Embodiments of the invention preferably further recognise that the obtained biomarker measurements are likely to constitute a sparse sample set, due to the difficulty in obtaining such measurements less than about daily from the diseased subject. In a further embodiment, the actual time the therapy was administered, further measurements of the biomarker following administration and/or the outcome of therapy are analysed to allow further refinement of the determination of the preferred time to administer a specific therapy, to a subject whose immune system is cycling in a particular way and/or to take into account any other factors relevant to the determination of the preferred time for a given set of circumstances.

According to another aspect, the present invention provides a computer-implemented method for analysing a biomarker which cycles in a subject with a disease, the method comprising:

i) sending measurements of the biomarker to a computing device, wherein the computing device is operable to estimate a periodicity of the cycling of the biomarker based on the measurements; and ii) receiving the estimated periodicity of the cycling from the computing device.

According to a further aspect, the present invention provides a computer system for analysing a biomarker which cycles in a subject with a disease, the system comprising a computing device operable to estimate a periodicity of the cycling of the biomarker in the subject based on measurements of the biomarker.

The computing device may also be operable to determine from the estimated periodicity of the cycling a preferred time to administer a therapy to treat a disease in the subject.

The measurements may be received via a communications network from a plurality of distributed testing locations, the measurements relating to the cycling of a biomarker of each of a plurality of diseased subjects.

According to a further aspect, the present invention provides a computer program product comprising computer program code means to cause a computer to implement a method for determining a preferred timing of administration of a therapy in accordance with a method of the invention.

According to another aspect, the present invention provides an apparatus comprising a data processing means which is arranged to determine a preferred timing of administration of a therapy in accordance with a method of the invention.

Instead of relying on the analysis of the cycling of the immune system to treat the disease, the immune system can at least be partially "reset" and the emerging T cell population of interest (effector or regulator depending on the disease) can be targeted at the appropriate time. Thus, in yet another aspect, the present invention provides a computer-implemented method for analysing a biomarker which at least initially increases or decreases in amount in a subject following a treatment for a disease, the method comprising estimating the timing and/or rate of the at least initial increase or decrease in amount of the biomarker based on measurements of the biomarker, the measurements having been at least obtained after the treatment.

The method may further comprise determining from the estimated timing and/or rate of increase or decrease a preferred time in the future to administer the therapy. The measurements of the biomarker may be received via a communications network, or retrieved from a remote or local storage.

Before and after said treatment the amount of the biomarker may be cycling in the subject, in which case the increase or decrease reflects the beginning of the first cycle following said treatment. Thus, the levels of the biomarker is typically cycling in the subject with the disease and the treatment disrupts and resets the cycling. Furthermore, this means that this aspect, and related aspects, are practiced immediately after the treatment, such as within about 28 days, or within about 21 days, or within about 14 days.

Examples of biomarkers which increase after the treatment are, but not limited to, effector T cells, regulator T cells (after the effector T cells) and positive acute phase inflammatory markers. Examples of biomarkers which decrease after treatment are, but not limited to, cancer antigen markers in subjects with cancer, and viral load in subjects with a viral infection such as HIV.

The "treatment" and the "therapy" in this, and related aspects, can be the same or different. Thus, this, and related aspects, can be considered as providing a first therapy to at least partially reset the immune system and a second therapy to effectively treat the disease by targeting the T cell population of interest.

Estimating the timing and/or rate may comprise obtaining a best-fit curve to the measurements in accordance with a model of the cycling of the biomarker to estimate the timing and rate of the at least initial increase or decrease in amount of the biomarker. Obtaining the best-fit curve may further comprise imposing a box constraint on at least some parameters of the model to guide optimisation to biologically realistic regions. The method may further comprise projecting the obtained best-fit curve into the future to estimate the preferred time to administer the therapy.

The method may further comprise determining a variance-stabilizing transformation of the measurements prior to estimating the timing and rate. The variance-stabilizing transformation of measurements may be logarithm of the measurements. Other suitable transformations include In a further aspect, the present invention relates to a computer-implemented method for analysing a biomarker which at least initially increases or decreases in amount in a subject following a treatment for a disease, the method comprising:

i) sending measurements of the biomarker in the subject to a computing device, wherein the measurements are at least obtained after said treatment, and wherein the computing device is operable to estimate the timing and/or rate of the at least initial increase or decrease in amount of the biomarker based on the measurements; and ii) receiving the estimated timing and/or rate of the at least initial increase or decrease in amount of the biomarker.

In a further aspect, the present invention relates to a computer program product comprising computer program code means to cause a computer to implement a method for analysing a biomarker which at least initially increases or decreases in amount in a subject following a treatment for a disease.

In a further aspect, the present invention relates to a computer system for analysing a biomarker which at least initially increases or decreases in amount in a subject following a treatment for a disease, the system comprising a computing device operable to estimate the timing and/or rate of the at least initial increase or decrease in amount of the biomarker based on measurements of the biomarker, the measurements being at least obtained after the treatment.

In a further aspect, the present invention relates to a computer-implemented method for determining a preferred time to administer a therapy to treat a disease in a subject, the method comprising:

i) based on measurements of a biomarker which cycles in the subject, estimating a periodicity of the cycling of the biomarker; and ii) determining from the estimated periodicity of the cycling a preferred time in the future to administer the therapy to treat the disease in the subject.

In a further aspect, the present invention relates to a computer-implemented method for determining a preferred time to administer a therapy to treat a disease in a subject, the method comprising:

i) based on measurements of a biomarker which at least initially increases or decreases in amount in the subject following a treatment for the disease, estimating a timing and/or rate of the at least initial increase or decrease, wherein the measurements are at least obtained after the treatment; and ii) determining from the estimated timing and/or rate of increase or decrease a preferred time in the future to administer the therapy.

In a further aspect, the present invention relates to a computer system for determining a preferred time to administer a therapy to treat a disease in a subject, the system comprising a computing device operable to:

i) based on measurements of a biomarker which cycles in the subject, estimate a periodicity of the cycling of the biomarker; and ii) determine from the estimated periodicity of the cycling a preferred time in the future to administer the therapy to treat the disease in the subject.

In a further aspect, the present invention relates to a computer system for determining a preferred time to administer a therapy to treat a disease in a subject, the system comprising a computing device operable to:

i) based on measurements of a biomarker which at least initially increases or decreases in amount in the subject following a treatment for the disease, estimate a timing and/or rate of the at least initial increase or decrease, wherein the measurements are at least obtained after the treatment; and ii) determine from the estimated timing and/or rate of increase or decrease a preferred time in the future to administer the therapy.

In a further aspect, the present invention relates to a computer program product comprising computer program code means to cause a computer implement a method for determining a preferred time to administer a therapy to treat a disease in a subject.

With regard to cycling levels of an acute phase inflammatory marker, the present inventors have identified a particularly preferred timing of administration of the therapy to treat the disease. Thus, in a further aspect the present invention provides a method of treating a disease in a subject in which the immune system is cycling, the method comprising;

i) monitoring the subject to determine the periodicity of the cycling of an acute phase inflammatory marker in the subject, and ii) administering the therapy whilst the level of the acute phase inflammatory marker is increasing, between half way between a minimum in the cycle and a maximum in the cycle, but before the levels of the acute phase inflammatory marker have peaked, wherein the disease is characterized by the production of regulator T cells.

An example of this preferred timing of administration is shown schematically in FIG. 19.

Preferably, the disease characterized by the production of regulator T cells is selected from, but not limited to, cancer, an infection and a degenerative disease.

The infection can be caused by any type of infectious agent such as, but not limited to, a virus, bacteria, protozoa, nematode, prion, or fungus. Preferably, the infectious agent causes chronic persistent infection characterized by the patient's immune system not being able to eliminate the infectious agent. Examples of infectious agents which cause chronic persistent infection are viruses such as HIV, the Hepatitis B virus and the Hepatitis C virus.

In another aspect the present invention provides a method of treating a disease in a subject in which the immune system is cycling, the method comprising;

i) monitoring the subject to determine the periodicity of the cycling of an acute phase inflammatory marker in the subject, and ii) administering the therapy between just before and just after the acute phase inflammatory marker has reached its lowest point in the cycle, wherein the disease is characterized by the production of effector T cells.

Preferably, the disease characterized by the production of effector T cells is selected from, but not limited to, an autoimmune disease or transplant rejection.

In a preferred embodiment of the two above aspects, it is preferred that a second biomarker which is out of phase with the cycling of the acute phase inflammatory marker is also monitored and used to more accurately determine when to administer the therapy. Examples of biomarkers which cycle out of phase with acute phase inflammatory markers include, but are not limited to, TGFβ and IL-10.

With regard to the two above aspects, preferably the acute phase inflammatory marker is a positive acute phase inflammatory marker. Examples of positive acute phase inflammatory markers include, but are not limited to, c-reactive protein (CRP), serum amyloid A (SAA), serum amyloid P component, complement proteins such as C2, C3, C4, C5, C9, B, C1 inhibitor and C4 binding protein, fibrinogen, von Willebrand factor, α1-antitrypsin, α1-antichymotrypsin, α2-antiplasmin, heparin cofactor II, plasminogen activator inhibitor I, haptoglobin, haemopexin, ceruloplasmin, manganese superoxide dismutase, α1-acid glycoprotein, haeme oxygenase, mannose-binding protein, leukocyte protein I, lipoprotein (a), lipopolysaccharide-binding protein, and interleukins such as IL-1, IL-2, IL-6, IL-10 and receptors thereof. Preferably, the positive acute phase inflammatory marker is CRP or SAA, more preferably CRP.

Due to the complexities described below, the present inventors have devised a treatment regime which optimizes the possibility of effectively treating the disease. This procedure relies on slightly overestimating the optimal time of administration of the therapy, and then backing into the cycle with recurrent treatments over a number of cycles. Accordingly, in a further aspect the present invention provides a method of treating a disease in a subject in which the immune system is cycling, the method comprising i) monitoring the subject to determine the periodicity of the cycling of a biomarker which cycles in the disease, ii) predicting the optimal time in the cycle to administer a therapy to treat the disease, iii) administering a first therapy at a time selected after the predicted optimal time, iv) administering a second therapy in the next cycle following step iii) at a time selected earlier in the cycle than the first therapy, and optionally v) administering a third therapy in the next cycle following step iv) at a time selected earlier in the cycle than the second therapy.

In one embodiment, the first therapy is administered between about 12 hours to about 48 hours after the predicted optimal time. In another embodiment, the second therapy is administered between about 12 hours and about 24 hours earlier in the cycle than the first therapy. In a further embodiment, the third therapy is administered between about 12 hours and about 24 hours earlier in the cycle than the second therapy. The treatment can be continued with further therapies administered in subsequent cycle between about 12 hours and about 24 hours earlier than the previous cycle. However, it is likely that two, and at most three, administrations of the therapy will be sufficient to treat the disease.

The first, second, third, etc therapies can be the same or different therapies, but preferably the same.

Also provided is the use of a therapy for the manufacture of a medicament for treating a disease in a subject in which the immune system is cycling, wherein the subject is monitored to determine the periodicity of cycling of an acute phase inflammatory marker in the subject, and the therapy is to be administered whilst the level of the acute phase inflammatory marker is increasing, between half way between a minimum in the cycle and a maximum in the cycle, but before the levels of the acute phase inflammatory marker have peaked, wherein the disease is characterized by the production of regulator T cells.

Also provided is the use of a therapy for the manufacture of a medicament for treating a disease in a subject in which the immune system is cycling, wherein the subject is monitored to determine the periodicity of cycling of an acute phase inflammatory marker in the subject, and the therapy is to be administered between just before and just after the acute phase inflammatory marker has reached its lowest point in the cycle, wherein the disease is characterized by the production of effector T cells.

Also provided is the use of a therapy for the manufacture of a medicament for treating a disease in a subject in which the immune system is cycling, wherein the subject is monitored to determine the periodicity of the cycling of a biomarker which cycles in the disease, and the therapy is to be sequentially administered i) at a time selected after a predicted optimal time to administer the therapy followed by ii) at a time selected earlier in the cycle than i) and optionally followed by iii) at a time selected earlier in the cycle than ii).

Unless specified otherwise, the biomarker to be analysed is any cell or molecule, the levels of which are cycling in the diseased subject. Examples of such biomarkers include, but are not limited to, regulator T cells, effector T cells, molecules associated with the disease, and/or immune system markers.

Preferably, the immune system marker reflects the number and/or activity of regulator T cells, and/or the number and/or activity of effector T cells. In a preferred embodiment, the immune system marker (biomarker) is an acute phase inflammatory protein.

In an embodiment, the regulator T cells are CD4+CD8− T cells.

In another embodiment, the effector T cells are CD8+ CD4− T cells.

In a further embodiment, the molecule associated with the disease is an antigen, or nucleic acid encoding therefore, produced by a cancer cell or an infectious agent.

It will be appreciated by the skilled person that diseases such as cancer, autoimmunity and AIDS have a complex effect on the patient. Furthermore, natural variations between individuals linked to factors such as their genotype, nutrition, fitness, previous and current disease status, all influence how a given individual responds to a disease state. Thus, whilst in most cases the cycle will be somewhere between 3 and 15 days (often depending on the biomarker being analysed), in some individuals this may be slightly shorter or longer. In addition, like the menstrual cycle, the length of the cycle may vary slightly within an individual due to natural variation and/or environmental factors. Thus, individual variation may at least be encountered with regard to, for example, i) the length (periodicity) of the cycle, ii) the absolute numbers of effector or regulator T cells during the cycle, or iii) the levels of acute phase inflammatory markers during the cycle. Such variation may be exaggerated in patients with advanced disease, where the patient's immune system has been challenged for a considerable length of time.

As result, it will most likely be desirable to monitor the subject for a sufficient length of time to ensure that the dynamics of biomarker cycling within a particular subject is understood. Preferably, the subject is monitored/measured for a period of at least 7 days, more preferably at least 14 days, more preferably at least 21 days, more preferably at least 28 days, more preferably at least 35 days, more preferably at least 42 days, and even more preferably at least 49 days.

Furthermore, it is preferred that the subject is monitored as frequently as possible to ensure biomarker cycling within a given subject is suitably characterized. Naturally this will ensure that the therapy is administered at the appropriate time and that any small variation in the biomarker is not misinterpreted. Preferably, the subject is monitored at least every 3 days, more preferably at least every 2 days, and most preferably at least every day. Monitoring may occur more frequently, for instance every 12 hours, when the cycling is reaching a stage where it is likely that the timing would be appropriate to administer the therapy. Thus, it is preferred that serial measurements with a defined frequency have been taken, however, the invention nonetheless allows the use of infrequent measurements as long as there is enough representative data to make a prediction as to when to administer the therapy.

A further complicating factor will be if the subject has recently acquired a disease or trauma unrelated to that being treated. For example, a subject being treated for a HIV infection may also contract the common flu virus. The presence of the flu virus will result in, for example, an increase in acute phase inflammatory markers independent of the cycling of these markers which is occurring due to the HIV infection. Accordingly, it is desirable to monitor the subject for any factors which may result in elevated levels of, for example, acute phase inflammatory markers to ensure that the factor being monitored truly reflects biomarker cycling resulting from the disease being treated.

As outlined above, in an embodiment numerous biomarkers are monitored at the same time. This is because, due to the factors describe above, it is unlikely that each biomarker will have a perfect cycle profile within a given period, particularly over a number of cycles, to routinely provide a clear indication of the appropriate time to administer the therapy. Whilst the analysis of numerous factors of a long period may be costly, and may be of at least some inconvenience to the subject, diseases such as cancer and AIDS are life threatening. Hence it is worthwhile understanding as much as possible regarding biomarker cycling in a given subject before the subject is treated.

When the disease is characterized by the production of regulator T cells it is particularly preferred the therapy inhibits the production of, limits the function of, and/or destroys, regulator T cells. More preferably, the therapy is selected from the group consisting of anti-cancer drugs such as anti-proliferative drugs, a vaccine, radiation, dsRNA and antibodies which inhibit the production and/or activity of regulator T cells. Preferably, the anti-proliferative drug is selected from the group consisting of, but not limited to, taxol, vincristine, vinblastine, temozolomide and anhydro vinblastine.

Examples of preferred antibodies for treating a disease characterized by the production of regulator T cells include, but are not limited to, anti-CD4+, anti-CTLA-4 (cytotoxic lymphocyte-associated antigen-4), anti-GITR (glucocorticoid-induced tumour necrosis factor receptor), anti-CD28 and anti-CD25.

When the disease is characterized by the production of effector T cells it is particularly preferred the therapy inhibits the production of, limits the function of, and/or destroys, effector T cells. More preferably, the therapy is selected from the group consisting of anti-cancer drugs such as anti-proliferative drugs, a vaccine, radiation, dsRNA and antibodies which inhibit the production and/or activity of effector T cells. An example of an antibody for treating a disease characterized by the production of effector T cells is an anti-CD8+ antibody.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting examples and with reference to the accompanying figures.

DETAILED DESCRIPTION OF THE INVENTION

General Techniques and Definitions

Figure 1:
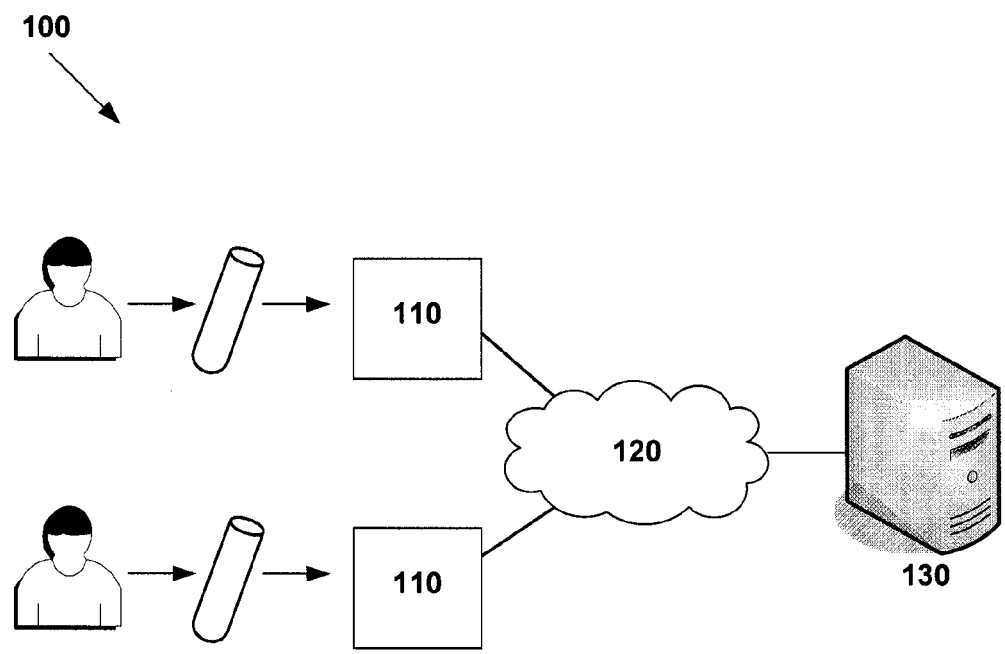
FIG. 1: Illustrates a distributed system for obtaining cyclic biomarker measurements, centrally processing such measurements, and determining a suitable future time for administration of a therapy.

Unless specifically defined otherwise, all technical and scientific terms used herein shall be taken to have the same meaning as commonly understood by one of ordinary skill in the art (e.g., in cell culture, molecular genetics, cancer therapy, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein the terms "treating", "treat" or "treatment" include administering a therapeutically effective amount of a therapy sufficient to reduce or eliminate at least one symptom of the disease. In an embodiment, these terms are used to indicate that the methods of the invention increase the length of progression free survival of the subject from the disease when compared to an untreated patient, and/or the methods of the invention increase the average length of progression free survival of a group of subjects from the disease when compared to the average from a group which have been randomly treated with the therapy.

As used herein, "cycling" or "cycle" or variations thereof refers to a repetitive (persistent) oscillation of a biomarker (cell number, activity of, marker of disease, immune system marker etc.), wherein the biomarker changes periodically from a maximum to a minimum for a given length of time which is typically about 3 days to about 15 days, more typically about 7 days to about 14 days, depending on the biomarker. Furthermore, as used herein the term "the periodicity of the cycling" or variations thereof refers to the length of time of one wave of the cycle from a given point to when the levels of the biomarker return to the corresponding point in the next wave.

As used herein, the term "determining a preferred timing of administration of a therapy" or variations thereof refers to the analysis of biomarker (immune system) cycling, or the timing and/or rate of the at least initial increase or decrease in amount of the biomarker following "resetting" the immune system, to predict when the therapy should be administered to increase the chances the disease will be effectively treated.

As used herein, the term "predicting the optimal time in the cycle" refers to the best estimation of when the therapy should be administered to target the clonal expansion of the relevant cells based on the monitoring data.

The term "immune system marker" generally refers to any molecule or factor which provides an indication of the state and/or activity of the immune system. These markers may be directly linked to the activity and/or production of regulator and/or effector T cells, and/or may provide a more general indication of the overall response of the immune system to an antigen. Examples of a suitable immune system marker include acute phase inflammatory markers such as c-reactive protein and serum amyloid A. Another example of an immune system marker are indicators of cellular destruction such as, but not limited to, cholesterol and β-2-microglobulin in serum. Cholesterol and β-2-microglobulin are integral components of cellular membranes. In particular, β-2-microglobulin is the accessory molecule to the Major Histocompatabilty Class I or MHC-I receptor. Consequently, with the cycling of the anti-disease immune response together with target cell destruction, the serum levels in diseased patients of these two molecules is often elevated. Thus, oscillations in indicators of cellular destruction, such as cholesterol and β-2-microglobulin, may also prove useful in determining the beginning or end of the immune response cycle. Another example of an immune system marker is body temperature, however, in this instance the patient is monitored directly without the need to obtain a sample.

As used herein, "out of phase" refers to two different biomarkers peaking at different, for example opposite, times during immune system cycling. More specifically, when one biomarker has peaked in the cycle, the other biomarker is about at its lowest point, and vice versa.

"Effector T cells" include, but are not necessarily limited to, the T cell population known as CD8+ cells.

"Regulator T cells" include, but are not necessarily limited to, a subpopulation of CD4+ T cells. Such cells may also be referred to in the art as "suppressor cells" or "regulatory T cells". Regulator T cells may either act directly on effector T cells or may assert their affects upon effector T cells through other mechanisms.

CD4+ cells express the marker known in the art as CD4. Typically, the term "CD4+ T cells" as used herein does not refer to cells which also express CD8. However, this term can include T cells which also express other antigenic markers such as CD25.

As used herein, the term "inhibits the production of limits the function of, and/or destroys" when referring to the exposure of the "effector T cells" to the therapy means that the number, and/or activity, of effector T cells is down-regulated by the therapy. Most preferably, the number, and/or activity, of effector T cells is completely eradicated by the therapy.

As used herein, the term "inhibits the production of, limits the function of, and/or destroys" when referring to the exposure of the "regulator T cells" to the therapy means that the number, and/or activity, of regulator T cells is down-regulated by the therapy. Most preferably, the number, and/or activity, of regulator T cells is completely eradicated by the therapy.

As used herein the term "disease characterized by the production of regulator T cells" refers to any condition wherein the number or activity of regulator T cells plays a role in prolonging the disease state. Examples of such disease include, but are not limited to, cancer, degenerative diseases and infection especially chronic persistent infections.

As is known in the art, a cancer is generally considered as uncontrolled cell growth. The methods of the present invention can be used to treat any cancer including, but not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma.

As used herein, the term "chronic persistent infection" refers to the presence of an infectious agent in the subject which is not readily controlled by the subject's immune system or available therapies. Examples include, but are not limited to, infections with *Mycobacterium tuberculosis* (which causes tuberculosis), the Hepatitis B virus, the Hepatitis C virus or retroviruses such as HIV. To be classified as a "chronic persistent infection" it is preferred that the subject has at least had the infection for 3 months, more preferably at least 6 months.

As used herein, a "degenerative disease" is a condition that results in the loss of cells. Preferably, the degenerative disease is a neurodegenerative disease which is marked by the loss of nerve cells. Examples of neurodegenerative diseases relevant to the present invention include, not are not limited to, Alexander disease, Alzheimer disease, Amyotrophic lateral sclerosis (Lou Gehrigs' disease), Ataxia Telangiectasia, Canavan disease, Cockayne syndrome, Corticobasal Degeneration, Huntington disease, Kennedy's disease, Krabbe disease, Lewy body dementia, Machado-Joseph disease, Parkinson disease, Pelizaeus-Merzbacher Disease, Pick's disease, Primary lateral sclerosis, Refsum's disease, Sandhoff disease, Schilder's disease, Steele-Richardson-Olszewski disease, Tabes dorsalis, and prion related diseases such as Creutzfeldt-Jakob disease, Alper's disease, Kuru, Gersymann-Straussler-Scheinker syndrome, Fatal familial insomnia, scrapie, transmissible milk encephalopathy, chronic wasting disease, and bovine spongiform encephalopathy. In another embodiment, the degenerative disease is an "amyloid related disease", examples of which include, but are not limited to, Alzheimer disease, Type II diabetes and cerebral amyloid angiopathy.

As used herein the term "disease characterized by the production of effector T cells" refers to any condition wherein the number or activity of effector T cells plays a role in prolonging the disease state. These disease are either i) typically characterized by an immune response against self antigens known generally in the art as autoimmune diseases, or ii) involve a subjects immune response during organ/tissue/cell transplantation from a suitable donor. Examples of such disease include, but are not limited to, autoimmune diseases and transplant rejections including both graft-versus-host disease and host-versus-graft disease.

As used herein, the term "autoimmune disease" refers to any disease in which the body produces an immunogenic (ie, immune system) response to some constituent of its own tissue. In other words the immune system loses its ability to recognize some tissue or system within the body as "self" and targets and attacks it as if it were foreign. Autoimmune diseases can be classified into those in which predominantly one organ is affected (eg, hemolytic anemia and anti-immune thyroiditis), and those in which the autoimmune disease process is diffused through many tissues (eg, systemic lupus erythematosus). Examples of autoimmune diseases include, but are not limited to, rheumatoid arthritis, multiple sclerosis, lupus erythematosis, myasthenia gravis, scleroderma, Crohn's disease, ulcerative colitis, Hashimoto's disease, Graves' disease, Sjogren's syndrome, polyendocrine failure, vitiligo, peripheral neuropathy, autoimmune polyglandular syndrome type I, acute glomerulonephritis, Addison's disease, adult-onset idiopathic hypoparathyroidism (AOIH), alopecia totalis, amyotrophic lateral sclerosis, ankylosing spondylitis, autoimmune aplastic anemia, autoimmune hemolytic anemia, Behcet's disease, Celiac disease, chronic active hepatitis, CREST syndrome, dermatomyositis, dilated cardiomyopathy, eosinophilia-myalgia syndrome, epidermolisis bullosa acquisita (EBA), giant cell arteritis, Goodpasture's syndrome, Guillain-Barr syndrome, hemochromatosis, Henoch-Schonlein purpura, idiopathic IgA nephropathy, insulin-dependent diabetes mellitus (IDDM), juvenile rheumatoid arthritis, Lambert-Eaton syndrome, linear IgA dermatosis, myocarditis, narcolepsy, necrotizing vasculitis, neonatal lupus syndrome (NLE), nephrotic syndrome, pemphigoid, pemphigus, polymyositis, primary sclerosing cholangitis, psoriasis, rapidly-progressive glomerulonephritis (RPGN), Reiter's syndrome, stiff-man syndrome, inflammatory bowel disease, osteoarthritis and thyroiditis.

The term "transplant" and variations thereof refers to the insertion of a graft into a host, whether the transplantation is allogeneic (where the donor and recipient are of different genetic origins but of the same species), or xenogeneic (where the donor and recipient are from different species). Thus, in a typical scenario, the host is human and the graft is an isograft, derived from a human of the same or different genetic origins. In another scenario, the graft is derived from a species different from that into which it is transplanted, such as a baboon heart transplanted into a human recipient host, and including animals from phylogenically widely separated species, for example, a pig heart valve, or animal beta islet cells or neuronal cells transplanted into a human host. Cells, tissues and/or organs may be transplanted, examples include, but are not limited to, isolated cells such as islet cells; tissue such as the amniotic membrane of a newborn, bone marrow, hematopoietic precursor cells, and ocular tissue, such as corneal tissue; and organs such as skin, heart, liver, spleen, pancreas, thyroid lobe, lung, kidney, tubular organs (e.g., intestine, blood vessels, or esophagus), etc. The tubular organs can be used to replace damaged portions of esophagus, blood vessels, or bile duct. The skin grafts can be used not only for burns, but also as a dressing to damaged intestine or to close certain defects such as diaphragmatic hernia. The graft is derived from any mammalian source, including human, whether from cadavers or living donors. Preferably the graft is bone marrow or an organ such as heart.

As used herein, the term "graft-versus-host disease" refers to is an immune attack on the recipient by cells from a donor. Whilst the transplanted cells can be of any cell type, typically the only transplanted tissues that house enough immune cells to cause graft versus host disease are the blood and the bone marrow.

As used herein, the term "host-versus-graft disease" refers to the lymphocyte-mediated reactions of a host against allogeneic or xenogeneic cells acquired as a graft or otherwise, which lead to damage or/and destruction of the grafted cells. This is the common basis of graft rejection.

As used herein, "transplant rejection" or variations thereof refers to the host's immune system mounting an immune response to the graft, ultimately resulting in the graft being rejected by the host. There are generally two types of "transplant rejection", namely graft-versus-host disease and host-versus-graft disease.

As used herein, the term "a molecule associated with the disease" refers to any molecule which is linked to the disease state. In a preferred embodiment, the marker is a protein, or a nucleic acid encoding therefor such as a gene or an mRNA. Such protein and nucleic acid markers are well known in the art. For example, levels of amyloid-β peptide can be a marker of Alzheimer's disease, and prion proteins in their β-confirmation can be a marker of prion related diseases. Examples of suitable tumour antigen markers include, but are not limited to, for AFP (marker for hepatocellular carcinoma and germ-cell tumours), CA 15-3 (marker for numerous cancers including breast cancer), CA 19-9 (marker for numerous cancers including pancreatic cancer and biliary tract tumours), CA 125 (marker for various cancers including ovarian cancer), calcitonin (marker for various tumours including thyroid medullary carcinoma), catecholamines and metabolites (phaeochromoctoma), CEA (marker for various cancers including colorectal cancers and other gastrointestinal cancers), hCG/beta hCG (marker for various cancers including germ-cell tumours and choriocarcinomas), 5HIAA in urine (carcinoid syndrome), PSA (prostate cancer), sertonin (carcinoid syndrome) and thyroglobulin (thyroid carcinoma). Suitable markers for, if not all, infectious diseases are also well known, for example the gag or env proteins of HIV.

As used herein, the term "monitoring" or variations thereof refers to the analysis of the levels of a biomarker over a sufficient period of time to suitably characterize the periodicity of the cycling of the biomarker, or the timing and/or rate of the at least initial increase or decrease in amount of the biomarker following "resetting" the immune system. Examples of suitable time periods and frequency of analysis are described herein. Generally, the monitoring/analysis will be performed on samples obtained from the subject. However, in some instances the monitoring/analysis will be performed directly on the subject, such as the determination of body temperature.

The "sample" refers to a material suspected of containing the biomarker such as regulator T cells, effectors cells, immune system markers and/or a molecule associated with the disease. The sample can be used as obtained directly from the source or following at least one step of (partial) purification. The sample can be prepared in any convenient medium which does not interfere with the method of the invention. Typically, the sample is an aqueous solution or biological fluid as described in more detail below. The sample can be derived from any source, such as a physiological fluid, including blood, serum, plasma, saliva, sputum, ocular lens fluid, buccal swab, sweat, faeces, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Preferably, the sample is blood or a fraction thereof. Pretreatment may involve, for example, preparing plasma from blood, diluting viscous fluids, and the like. Methods of treatment can involve filtration, distillation, separation, concentration, inactivation of interfering components, and the addition of reagents. The selection and pretreatment of biological samples prior to testing is well known in the art and need not be described further. In some embodiments, due to current technology a drop of blood from a finger prick will be a sufficient sample, for example for testing acute phase inflammatory marker levels.

The term "subject" as used herein is intended to mean any animal, in particular mammals, such as humans, horses, cows, cats and dogs, and may, where appropriate, be used interchangeably with the term "patient". Preferably, the subject is a human.

The term "antibody" as used in this invention includes intact molecules as well as molecules comprising or consisting of fragments thereof, such as Fab, F(ab')2, and Fv which are capable of binding an epitopic determinant. These antibody fragments retain some ability to selectively bind to the target molecule such as CD8 or CD4, examples of which include, but are not limited to, the following:

(1) Fab, the fragment which contains a monovalent antigen-binding fragment of an antibody molecule can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab)$_2$ is a dimer of two Fab' fragments held together by two disulfide bonds;

(4) Fv, defined as a genetically engineered fragment containing the variable region of the light chain and the variable region of the heavy chain expressed as two chains;

(5) Single chain antibody ("SCA"), defined as a genetically engineered molecule containing the variable region of the light chain, the variable region of the heavy chain, linked by a suitable polypeptide linker as a genetically fused single chain molecule; such single chain antibodies may be in the form of multimers such as diabodies, triabodies, and tetrabodies etc which may or may not be polyspecific (see, for example, WO 94/07921 and WO 98/44001) and (6) Single domain antibody, typically a variable heavy domain devoid of a light chain.

Computer Modelling of Biomarkers

FIG. 1 illustrates a distributed system 100 for obtaining cycling biomarker measurements, centrally processing such measurements, and determining a suitable future time for administration of a therapy. A measurement device 110 measures biomarker levels of a plurality of diseased subjects in multiple locations. Obtained measurements are communicated via a wide area communications network such as the Internet 120 to a central computing device 130. For each individual, the computing device 130 estimates from the measurements a future time at which a therapy should be administered to, for example, increase the chance of progression free survival. The central computing device 130 may be a server and the measurement device 110 may be a desktop computer, a laptop computer wireless device such as a smartphone, or a dedicated computing device.

Figure 2:
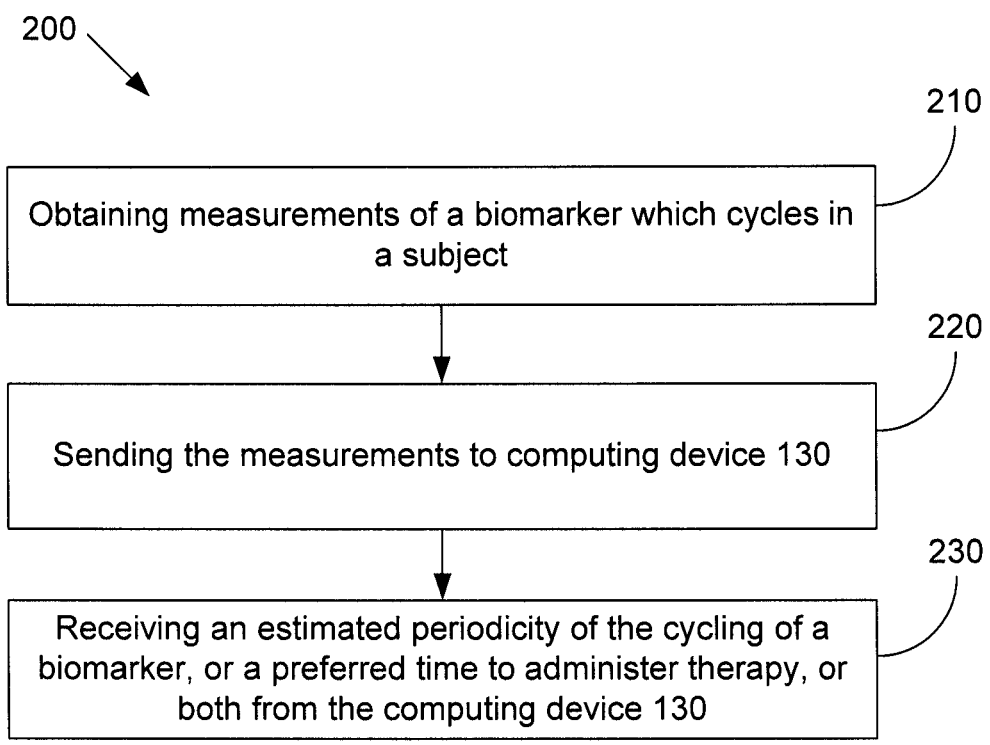
FIG. 2: A flowchart of steps performable by a measurement device at a testing location in communication with a central computing device via a wide area communications network in a first application.

In a first application, the measurement device 110 is operable to obtain measurements of a biomarker which cycles in time in a subject; see step 210 in FIG. 2. The measurements are then sent to the central computing device 130 via the Internet 120; see step 220. Alternatively or additionally, the measurements may be sent to a remote data store for retrieval by the central computing device.

Figure 3:
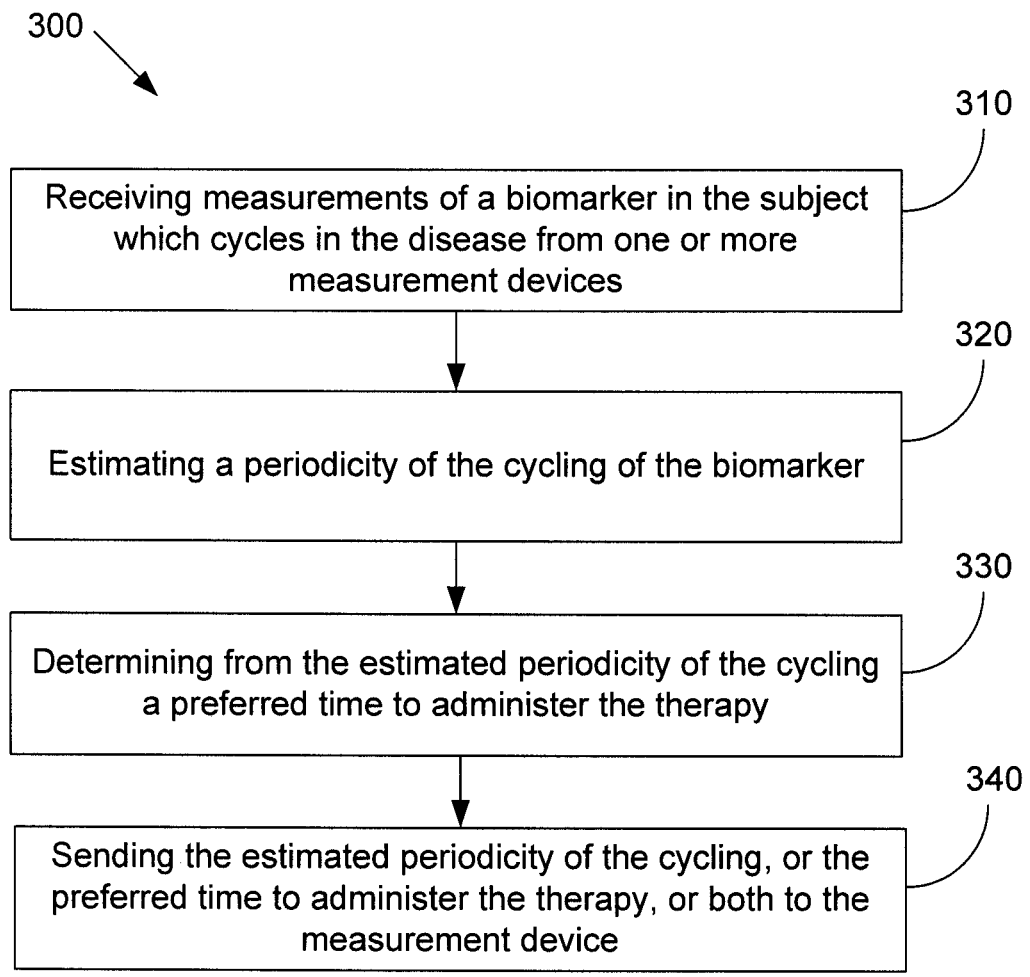
FIG. 3: A flowchart of steps performable by a central computing device in communication with plural measurement devices via a wide area communications network in a first application.

At the central computing device 130, the measurements are received or retrieved from the data store, and analysed to estimate a periodicity of the cycling of the biomarker; see steps 310 and 320 in FIG. 3. From the estimated periodicity of the cycling of the biomarker, the central computing device 130 then determines a preferred time to administer the therapy and sends the estimated periodicity and/or the preferred time to the measurement device 110 via the Internet 120; see steps 330 and 340 in FIG. 3.

At the measurement device 110, the estimated periodicity and/or the preferred time of administration is determined; see step 230 in FIG. 2. Alternatively or additionally, the estimated periodicity, or the preferred time, or both, is sent to another computing device that is independent of the measurement device 110.

Figure 4:
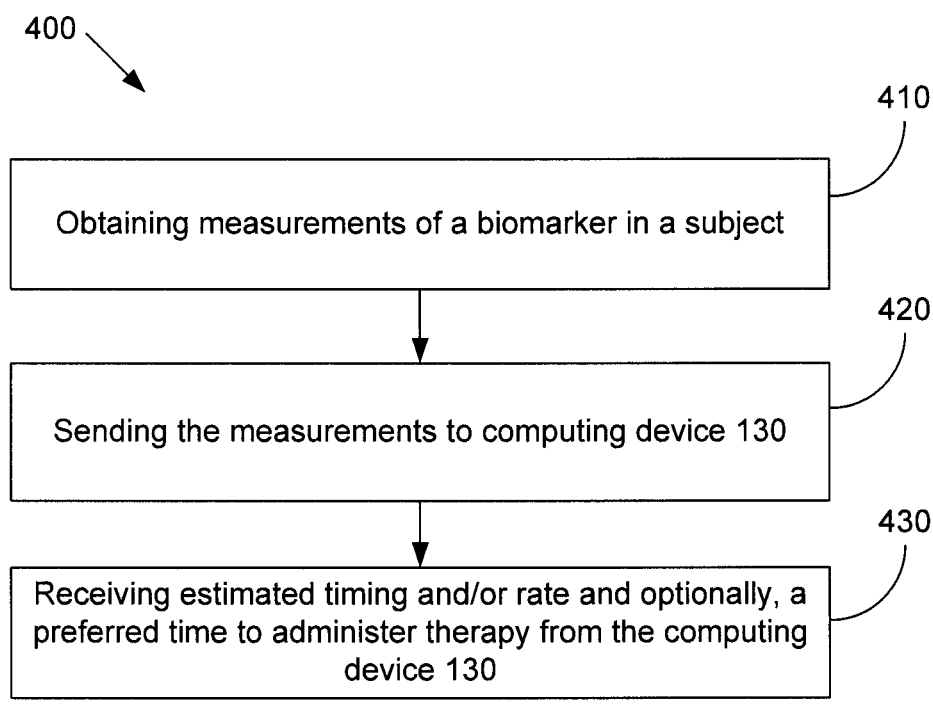
FIG. 4: A flowchart of steps performable by a measurement device at a testing location in communication with a central computing device via a wide area communications network in a second application.
Figure 5:
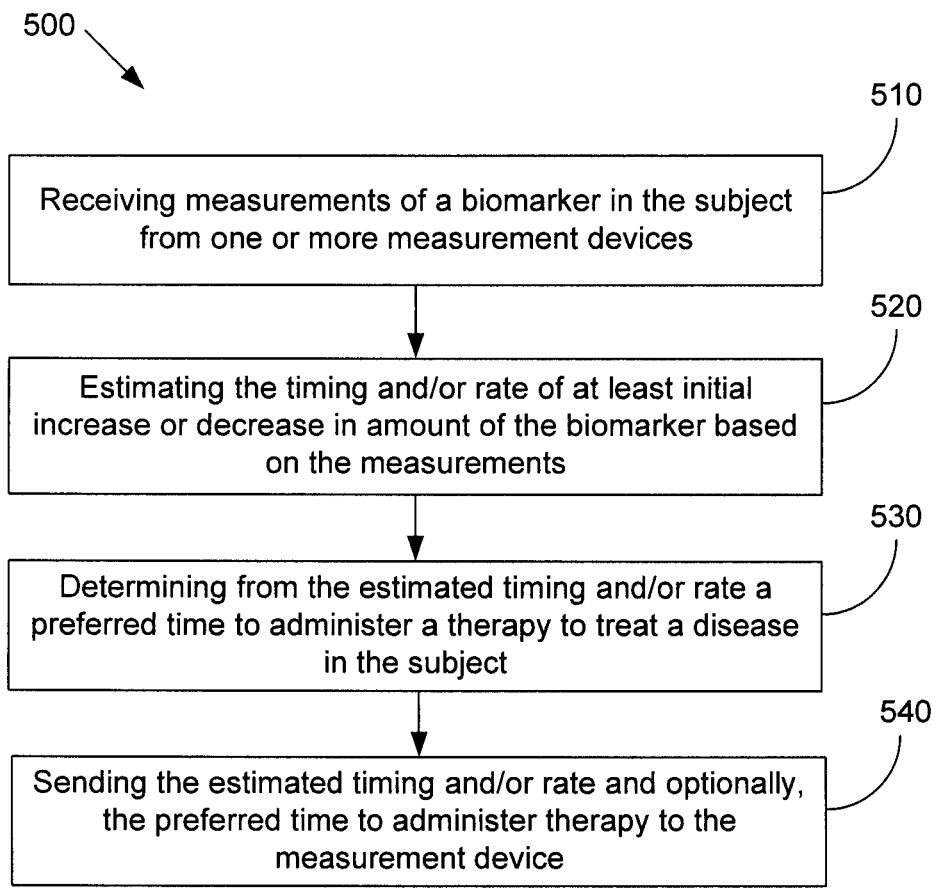
FIG. 5: A flowchart of steps performable by a central computing device in communication with plural measurement devices via a wide area communications network in a second application.

Instead of relying on the analysis of the cycling of the immune system to treat the disease, the immune system can at least be partially "reset" and the emerging T cell population of interest (effector or regulator depending on the disease) can be targeted at the appropriate time in a second application. Referring now to FIG. 4 and FIG. 5, the measurement device 110 is operable to obtain measurements of a biomarker in a subject where the biomarker at least initially increases or decreases in amount following being treated for the disease; see step 410 in FIG. 4. In this case, the measurements were at least obtained after said treatment. The measurements are then sent to the central computing device 130 via the Internet 120; see step 420. Alternatively or additionally, the measurements may be sent to a remote data store for retrieval by the central computing device.

At the central computing device 130, the measurements are received or retrieved from the data store; see step 510 in FIG. 5. The central computing device 130 then analyses the measurements to estimate the timing and/or rate of the at least initial increase or decrease in amount of the biomarker; see step 520 in FIG. 5. From the estimated timing and rate, the central computing device 130 then determines a preferred time in the future to administer the therapy; see step 530. The computing device 130 then sends the estimated timing and/or rate to the measurement device 110 via the Internet 120; see step 540. Alternatively or additionally, the preferred time is sent to the measurement device.

At the measurement device 110, the estimated timing and/or rate, and/or the preferred time of administration is determined; see step 430 in FIG. 4. Alternatively or additionally, the estimated timing and/or rate and preferred time is be sent to another computing device that is independent of the measurement device 110.

Some portions of this detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

As such, it will be understood that such acts and operations, which are at times referred to as being computer-executed, include the manipulation by the processing unit of the computer of electrical signals representing data in a structured form. This manipulation transforms the data or maintains it at locations in the memory system of the computer, which reconfigures or otherwise alters the operation of the computer in a manner well understood by those skilled in the art. The data structures where data is maintained are physical locations of the memory that have particular properties defined by the format of the data. However, while the invention is described in the foregoing context, it is not meant to be limiting as those of skill in the art will appreciate that various of the acts and operations described may also be implemented in hardware.

It should be borne in mind, however, that all of these and similar terms are to be associated with the appropriate physical quantities and are merely convenient labels applied to these quantities. Unless specifically stated otherwise as apparent from the description, it is appreciated that throughout the description, discussions utilizing terms such as "processing" or "computing" or "calculating" or "determining" or "displaying" or "obtaining" or "projecting" or "analysing" or "imposing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Figure 6:
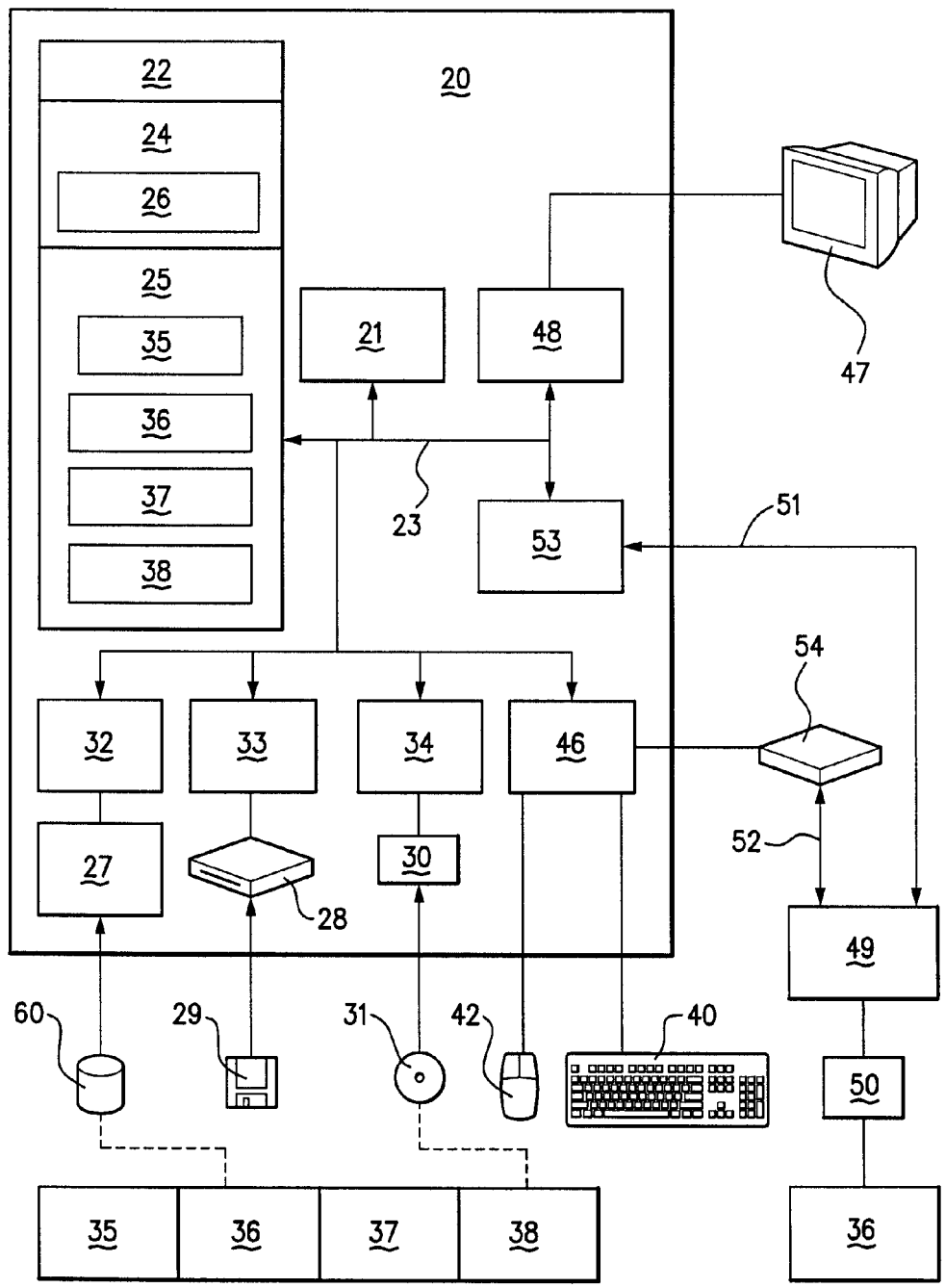
FIG. 6: Illustrates a general-purpose computing device that may be used in an exemplary system for implementing the invention.

The invention is illustrated as being implemented in a suitable computing environment (FIG. 6). Although not required, the invention will be described in the general context of computer-executable instructions, such as program modules, being executed by a personal computer. Generally, program modules include routines, programs, objects, components, data structures, etc. that perform particular tasks or implement particular abstract data types. Moreover, those skilled in the art will appreciate that the invention may be practiced with other computer system configurations, including hand-held devices, multi-processor systems, microprocessor-based or programmable consumer electronics, network PCs, minicomputers, mainframe computers, and the like. The invention may be practiced in distributed computing environments where tasks are performed by remote processing devices that are linked through a communications network. In a distributed computing environment, program modules may be located in both local and remote memory storage devices.

In FIG. 6, a general purpose computing device is shown in the form of a conventional personal computer 20, including a processing unit 21, a system memory 22, and a system bus 23 that couples various system components including the system memory to the processing unit 21. The system bus 23 may be any of several types of bus structures including a memory bus or memory controller, a peripheral bus, and a local bus using any of a variety of bus architectures. The system memory includes read only memory (ROM) 24 and random access memory (RAM) 25. A basic input/output system (BIOS) 26, containing the basic routines that help to transfer information between elements within the personal computer 20, such as during start-up, is stored in ROM 24. The personal computer 20 further includes a hard disk drive 27 for reading from and writing to a hard disk 60, a magnetic disk drive 28 for reading from or writing to a removable magnetic disk 29, and an optical disk drive 30 for reading from or writing to a removable optical disk 31 such as a CD ROM or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer readable instructions, data structures, program modules and other data for the personal computer 20. Although the exemplary environment shown employs a hard disk 60, a removable magnetic disk 29, and a removable optical disk 31, it will be appreciated by those skilled in the art that other types of computer readable media which can store data that is accessible by a computer, such as magnetic cassettes, flash memory cards, digital video disks, Bernoulli cartridges, random access memories, read only memories, storage area networks, and the like may also be used in the exemplary operating environment.

A number of program modules may be stored on the hard disk 60, magnetic disk 29, optical disk 31, ROM 24 or RAM 25, including an operating system 35, one or more applications programs 36, other program modules 37, and program data 38. A user may enter commands and information into the personal computer 20 through input devices such as a keyboard 40 and a pointing device 42. Other input devices (not shown) may include a microphone, joystick, game pad, satellite dish, scanner, or the like. These and other input devices are often connected to the processing unit 21 through a serial port interface 46 that is coupled to the system bus, but may be connected by other interfaces, such as a parallel port, game port or a universal serial bus (USB) or a network interface card. A monitor 47 or other type of display device is also connected to the system bus 23 via an interface, such as a video adapter 48. In addition to the monitor, personal computers typically include other peripheral output devices, not shown, such as speakers and printers.

The personal computer 20 may operate in a networked environment using logical connections to one or more remote computers, such as a remote computer 49. The remote computer 49 may be another personal computer, a server, a router, a network PC, a peer device or other common network node, and typically includes many or all of the elements described above relative to the personal computer 20, although only a memory storage device 50 has been illustrated. The logical connections depicted include a local area network (LAN) 51 and a wide area network (WAN) 52. Such networking environments are commonplace in offices, enterprise-wide computer networks, intranets and, inter alia, the Internet.

When used in a LAN networking environment, the personal computer 20 is connected to the local network 51 through a network interface or adapter 53. When used in a WAN networking environment, the personal computer 20 typically includes a modem 54 or other means for establishing communications over the WAN 52. The modem 54, which may be internal or external, is connected to the system bus 23 via the serial port interface 46. In a networked environment, program modules depicted relative to the personal computer 20, or portions thereof, may be stored in the remote memory storage device. It will be appreciated that the network connections shown are exemplary and other means of establishing a communications link between the computers may be used.

Therapy

The present invention relates broadly to the use of three different types of therapies. There are:

1) therapies which are specific for effector T cells (such as CD8+ specific antibodies) that can be used to treat a disease characterized by the production of effector T cells, 2) therapies which are specific for regulator T cells (such as CD4+ specific antibodies) that can be used to treat a disease characterized by the production of regulator T cells, and 3) non-selective therapies which influence effector T cells and regulator T cells, however, the timing of administration of the therapy dictates the cell type being targeted.

The current analysis indicates that there is about a 12 hour time period to administer the therapy in each cycle, and/or soon after "re-setting" the immune system. In a preferred embodiment, the therapy is oral, has high bioavailability, has low toxicity to the patient and/or has a half life of 6 to 15 hours. Examples of such therapies include alkalating agents, vinca alkaloids and taxanes.

Therapies for Treating a Disease Characterized by the Production of Regulator T Cells The therapy can be any agent, factor or treatment which selectively or non-selectively results in the destruction, limits the function of, or the inhibition of the production, of regulator T cells. For example, a CD4+ specific antibody could be used to specifically target CD4+ T cells. However, in some instances a non-selective therapy could be used, such as an anti-proliferative drug, an anti-metabolic drug or radiation, each of which target dividing cells. In particular, as with other cell types, regulator T cells are particularly vulnerable to destruction by anti-mitotic (anti-proliferative) drugs or spindle poisons (e.g. vinblastine or paclitaxel) when dividing and specifically in mitosis.

Preferably, the therapy is administered, or the estimation of the preferred time to administer, is such that the activity of the effector T cells is not significantly reduced. More specifically, the timing is such that the therapy exerts a proportionally greater effect against the regulator T cells than the effector T cells. It is clearly preferred that the agent is administered at a time when the ratio of effect against the regulator T cells to the effect against effector T cells is greatest. In a preferred embodiment, the therapy for treating a disease characterized by the production of regulator T cells is administered just before or just after regulator T cells begin clonally expanding.

The term "anti-proliferative drug" and "anti-metabolic drug" is a term well understood in the art and refers to any compound that destroys dividing cells or inhibits them from undergoing further proliferation. Anti-proliferative drugs include, but are not limited to, mechlorethamine, temozolomide, cyclophosphamide, ifosfamide, melphalan, chlorambucil, hexamethyl-melamine, thiotepa, busulfan, carmustine, lomustine, semustine, streptozocin, dacarbazine, methotrexate, fluorouracil, floxuridine, cytarabine, mercaptopurine, thioguanine, pentostatin, vinblastine, anhydro vinblastine, vincristine, etoposide, teniposide, dactinomycin, daunorubicin, doxorubicin, bleomycin, plicamycin, mitomycin, L-asparaginase, cisplatin, mitoxantrone, hydroxyurea, procarbazine, mitotane, aminoglutethimide, prednisone, hydroxyprogesterone caproate, medroprogesterone acetate, megestrol acetate, diethylstilbestrol, ethinyl estradiol, tamoxifen, testosterone propionate, radioactive isotopes, ricin A chain, taxol, diphtheria toxin, colchicine and pseudomonas exotoxin A.

Recent studies have suggested that CD4+CD25+ T cells play an important role in regulating immune cells directed against self antigens (Salomon et al, 2000; Suri-Payer and Cantor, 2001). Furthermore, targeting CD4+CD25+ T cells has been shown to enhance the ability of an animal to control tumour growth (Onizuka et al., 1999; Shimizu et al., 1999; Sutmuller et al., 2001). Accordingly, CD4+CD25+ T cells could be acting as regulator T cells as used herein. The activity of CD4+CD25+ T cells can be downregulated by anti-GITR, anti-CD28 and/or anti-CTLA-4 (Read et al., 2000;

Takahashi et al., 2000; Shimizu et al., 2002). Thus, these antibodies may be useful as agents for use in the methods of the present invention.

The therapy is usually administered in the dosage forms that are readily available to the skilled clinician, and are generally administered in their normally prescribed amounts (as for example, the amounts described in the Physician's Desk Reference, 55th Edition, 2001, or the amounts described in the manufacture's literature for the use of the therapy).

In one embodiment, the therapy is administered as a single bolus injection. In another embodiment, the therapy is administered by infusion. The period of infusion can be, for example, at least 3 hours, at least 12 hours or at least 24 hours.

It has also determined that treatment for a disease characterized by the production of regulator T cells can be enhanced (or the chances of successful treatment can be increased) when the vaccine is administered at the appropriate time. In these instances, the vaccine boosts the innate immune response against the disease. This will most likely be a result of increased numbers and/or activity of effector T cells. Although theoretically regulator T cells will still ultimately be produced, the boosting of the immune system allows the subject to suitably control the disease before the emergence of the regulator T cells. This scenario would explain why previous studies have shown that anti-HIV and anti-tumour vaccines are only successful in a small number of subjects. More specifically, there is only a small chance the vaccine will be administered at the same time the innate immune response to the disease is occurring. Other times of administration in the prior art occur when there are high numbers and/or activity of regulators cells, or at times which uncouple the natural cycling of the immune system.

Such a vaccine will comprise at least one antigen, or a polynucleotide encoding said antigen. The vaccine can be provided as any form known in the art such as, but not limited to, a DNA vaccine, ingestion of a transgenic organism expressing the antigen, or composition comprising the antigen.

As used herein, an "antigen" is any polypeptide sequence that contains an epitope which is capable of producing an immune response against the disease.

Antigens which are capable of raising an immune response against a cancer cell are well known in the art. Certain tumour antigens can be recognized and targeted by the immune system. This property may be due to overexpression by the tumour tissue. Some of these antigens can be detected in normal tissue. The tumour antigens targeted by T cells are generally proteins that are processed intracellularly and presented as short peptide fragments bound in the groove of the tumour MHC class I molecule to be recognized by $CD8^+$ cytotoxic T lymphocytes. The mere presence of a tumour antigen is not always sufficient to trigger an immune response. Co-stimulatory molecules such as B7.1 are sometimes required. Once antigen-specific T cells are stimulated, they are capable of recognizing and destroying the tumour. The conditions needed for the activation of antigen-specific T cells are stringent, but are open to genetic manipulation of target tumour cells and T cells.

Antigens which can be used to treat infections, such as HIV, are also well known in the art.

The antigen can be provided in any manner known in the art which leads to an immune response. An antigen can be, for example, native, recombinant or synthetic. Native antigens can be prepared, for example, by providing cell lysates of a tumour cell.

Vaccines may be prepared from one or more antigens. The preparation of vaccines which contain an antigen is known to one skilled in the art. Typically, such vaccines are prepared as injectables, or orals, either as liquid solutions or suspensions; solid forms suitable for solution in, or suspension in, liquid prior to injection or oral consumption may also be prepared. The preparation may also be emulsified, or the protein encapsulated in liposomes. The antigen is often mixed with carriers/excipients which are pharmaceutically acceptable and compatible with the active ingredient. Suitable carriers/excipients are, for example, water, saline, dextrose, glycerol, ethanol, or the like and combinations thereof.

In addition, if desired, the vaccine may contain minor amounts of auxiliary substances such as wetting or emulsifying agents, pH buffering agents, and/or adjuvants which enhance the effectiveness of the vaccine.

Typically, vaccines comprise an adjuvant. As used herein, the term "adjuvant" means a substance that non-specifically enhances the immune response to an antigen. Examples of adjuvants which may be effective include but are not limited to: N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. Further examples of adjuvants include aluminum hydroxide, aluminum phosphate, aluminum potassium sulfate (alum), bacterial endotoxin, lipid X, *Corynebacterium parvum* (*Propionobacterium acnes*), *Bordetella pertussis*, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.).

The proportion of antigen and adjuvant can be varied over a broad range so long as both are present in effective amounts. For example, aluminium hydroxide can be present in an amount of about 0.5% of the vaccine mixture ($Al_2O_3$ basis). Conveniently, the vaccines are formulated to contain a final concentration of antigenic polypeptide in the range of from 0.2 to 200 µg/ml, preferably 5 to 50 µg/ml, most preferably 15 µg/ml.

After formulation, the vaccine may be incorporated into a sterile container which is then sealed and stored at a low temperature, for example 4° C., or it may be freeze-dried. Lyophilisation permits long-term storage in a stabilised form.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. as a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

DNA vaccination involves the direct in vivo introduction of DNA encoding an antigen into tissues of a subject for expression of the antigen by the cells of the subject's tissue. Such vaccines are termed herein "DNA vaccines" or "nucleic acid-based vaccines". DNA vaccines are described in U.S. Pat. No. 5,939,400, U.S. Pat. No. 6,110,898, WO 95/20660 and WO 93/19183.

To date, most DNA vaccines in mammalian systems have relied upon viral promoters derived from cytomegalovirus (CMV). These have had good efficiency in both muscle and skin inoculation in a number of mammalian species. A factor known to affect the immune response elicited by DNA immunization is the method of DNA delivery, for example, parenteral routes can yield low rates of gene transfer and produce considerable variability of gene expression. High-velocity inoculation of plasmids, using a gene-gun, enhanced the immune responses of mice, presumably because of a greater efficiency of DNA transfection and more effective antigen presentation by dendritic cells. Vectors containing the nucleic acid-based vaccine of the invention may also be introduced into the desired host by other methods known in the art, e.g., transfection, electroporation, microinjection, transduction, cell fusion, DEAE dextran, calcium phosphate precipitation, lipofection (lysosome fusion), or a DNA vector transporter.

Transgenic plants producing a antigenic polypeptide can be constructed using procedures well known in the art. A number of plant-derived edible vaccines are currently being developed for both animal and human pathogens. Immune responses have also resulted from oral immunization with transgenic plants producing virus-like particles (VLPs), or chimeric plant viruses displaying antigenic epitopes. It has been suggested that the particulate form of these VLPs or chimeric viruses may result in greater stability of the antigen in the stomach, effectively increasing the amount of antigen available for uptake in the gut.

Another example of an therapy which can be administered in a method of the invention is dsRNA. dsRNA is used in RNA interference (RNAi) which is a phenomenon where upon introduction into a cell, mRNA homologous to the dsRNA is specifically degraded so that synthesis of gene products is suppressed. Examples of such an agent causing RNAi include, but are not limited to, a sequence having at least about 70% homology to the nucleic acid sequence of a target gene or a sequence hybridizable under stringent conditions, RNA containing a double-stranded portion having a length of at least 10 nucleotides or variants thereof. Examples of target genes include, but are not limited to, a gene required for replication or survival of a regulator T cell.

dsRNA having a length of about 20 bases (e.g., representatively about 21 to 23 bases) or less than about 20 bases, which is called siRNA in the art, can be used. Expression of siRNA in cells can suppress expression of a gene targeted by the siRNA. In another embodiment, an agent capable of causing RNAi may have a short hairpin structure having a sticky portion at the 3' terminus (shRNA; short hairpin RNA). As used herein, the term "shRNA" refers to a molecule of about 20 or more base pairs in which a single-stranded RNA partially contains a palindromic base sequence and forms a double-strand structure therein (i.e., a hairpin structure). shRNA can be artificially chemically synthesized. Alternatively, shRNA can be produced by linking sense and antisense strands of a DNA sequence in reverse directions and synthesizing RNA in vitro with T7 RNA polymerase using the DNA as a template. The length of the double-stranded portion is not particularly limited, but is preferably about 10 or more nucleotides, and more preferably about 20 or more nucleotides. The 3' protruding end may be preferably DNA, more preferably DNA of at least 2 nucleotides in length, and even more preferably DNA of 2-4 nucleotides in length.

An agent capable of causing RNAi useful for the invention may be artificially synthesized (chemically or biochemically) or naturally occurring. There is substantially no difference therebetween in terms of the effect of the present invention. A chemically synthesized agent is preferably purified by liquid chromatography or the like.

An agent capable of causing RNAi used in the present invention can also be produced in vitro. In this synthesis system, T7 RNA polymerase and T7 promoter can be used to synthesize antisense and sense RNAs from template DNA. These RNAs are annealed and thereafter are introduced into a cell.

dsRNA can be delivered to the subject using any means known in the art. Examples of methods of delivering dsRNA to a patient are described in, for example, US 20040180357, US 20040203024 and US 20040192629.

Therapies for Treating a Disease Characterized by the Production of Effector T Cells The therapy can be any agent, factor or treatment which selectively or non-selectively results in the destruction, limits the function of, or the inhibition of the production, of effector T cells. For example, a CD8+ specific antibody could be used to specifically target CD8+ T cells. However, in some instances a non-selective therapy could be used, such as an anti-proliferative drug, an anti-metabolic drug or radiation, each of which target dividing cells. In particular, as with other cell types, effector T cells are particularly vulnerable to destruction by anti-mitotic (anti-proliferative) drugs or spindle poisons (e.g. vinblastine or paclitaxel) when dividing and specifically in mitosis.

Each of the above mentioned types of therapies are also useful for treating diseases characterized by the production of effector T cells. With regard to dsRNA, the dsRNA molecule can be specific for mRNAs expressed only in effector T cells. Furthermore, antibodies useful for treating these diseases bind molecules present in effector T cells such as CD8.

Preferably, for these diseases the therapy is administered, or the estimation of the preferred time to administer, is such that the activity of the regulator T cells is not significantly reduced. More specifically, the timing is such that the therapy exerts a proportionally greater effect against the effector T cells than the regulator T cells. It is clearly preferred that the agent is administered at a time when the ratio of effect against the effector T cells to the effect against regulator T cells is greatest. In a preferred embodiment, the therapy for treating a disease characterized by the production of effector T cells is administered just before or just after effector T cells begin clonally expanding.

Acute Phase Inflammatory Markers

Some acute phase inflammatory markers initially increase during an immune response (referred to hereinafter as positive acute phase inflammatory markers) whilst others initially decrease during an immune response (referred to hereinafter as negative acute phase inflammatory markers). Acute phase inflammatory markers are also referred to in the art as acute phase reactants or acute phase proteins. The skilled addressee will be aware of the many assays which can be used to monitor acute phase inflammatory markers.

Examples of positive acute phase inflammatory markers include, but are not limited to, c-reactive protein, serum amyloid A, serum amyloid P component, complement proteins such as C2, C3, C4, C5, C9, B, C1 inhibitor and C4 binding protein, fibrinogen, von Willebrand factor, α1-antitrypsin, α1-antichymotrypsin, α2-antiplasmin, heparin cofactor II, plasminogen activator inhibitor I, haptoglobin, haemopexin, ceruloplasmin, manganese superoxide dismutase, α1-acid glycoprotein, haeme oxygenase, mannose-binding protein, leukocyte protein I, lipoprotein (a), lipopolysaccharide-binding protein, and interleukins such as IL-1, IL-2, IL-6, IL-10 and receptors thereof.

Example of negative acute phase inflammatory markers include, but are not limited to, albumin, pre-albumin, transferin, apoAI, apoAII, α2 HS glycoprotein, inter-α-trypsin inhibitor, histidine-rich glycoprotein.

Serum amyloid A (SAA) was discovered as a plasma component that shares antigenicity with amyloid AA, the chief fibrillar component in reactive AA amyloid deposits. SAA has been shown to be an acute phase reactant whose level in blood is elevated to 1000-fold or higher as part of the body's responses to various injuries including trauma, infection and inflammation.

SAA levels can be determined as known in the art, see for example Weinstein et al. (1984), Liuzzo et al. (1994), O'Hara et al. (2000), Kimura et al. (2001) and O'Hanlon et al. (2002).

C-reactive protein (CRP) is an important positive acute phase response protein, and its concentration in serum may increase as much as 1,000-fold during the acute phase response. CRP is a pentamer consisting of five identical subunits, each having a molecular weight of about 23,500.

C-reactive protein levels can be determined using techniques known in the art, these include, but are not limited to, those disclosed in Senju et al. (1983), Weinstein et al. (1984), Price et al. (1987), Liuzzo et al. (1994), Eda et al. (1998), Kimura et al. (2001) and ° Hanlon et al. (2002).

The complement proteins are a group of at least 20 immunologically distinct components. They normally circulate in the blood in an inactive form. They are able to interact sequentially with antigen-antibody complexes, with each other and with cell membranes in a complex but adaptable way to destroy viruses and bacteria and pathologically, even the hosts own cells. Abnormal serum levels of complement proteins may be due to either inherited or acquired diseases. At least circulating levels of C3 and C4 reflect a balance between complement consumption due to immune complex formation and increased synthesis due to acute phase response. Methods of measuring complement protein levels are well known in the art.

Levels of different interleukins can also be determined using procedures known in the art such as using the ProteoPlex™ cytokine assay kit (EMD Biosciences Inc., CA, USA).

Monitoring of Subjects

In most instances, the time point that the therapy is to be administered will need to be empirically determined in subjects at different stages of disease as their immune response kinetics may vary. Other factors such as the general health of the subject and/or the genetic makeup of the subject will also impact upon when is the appropriate time to administer the therapy.

Techniques known in the art can be used to monitor the growing population of effector and/or regulator T cells during the "cycle". Serial blood samples can be collected and quantitatively screened for T cell subsets (such as CD4+ and/or CD8+) by FACS analysis, or for acute phase marker levels as described above.

Optimally, the monitoring is continued to determine the effect of the therapy. Insufficient ablation, re-emergence of the effector T cells or regulator T cells (depending on the disease state being treated) will mean that the method of the present invention should be repeated. Such repeated cycles of treatment may generate immunological memory. It is therefore possible that the present invention, used in repetitive mode, may provide some prophylactic protective effect.

Monitoring can be performed at a central testing laboratory, or at least in some instances at some other location that is convenient for the patient such as using a point of care device. Examples of suitable point of care monitoring devices are produced by Universal Biosensors (Rowville, Australia) (see US 20060134713), Axis-Shield PoC AS (Oslo, Norway) and Clinical Lab Products (Los Angeles, USA).

EXAMPLES

Example 1

Clinical Trial and Analysis of Data

Methods and Methods
Patients, Treatment and Monitoring

A pilot clinical study was conducted on 12 patients with metastatic melanoma (median age 61; 4 female; 7 with M1c disease) at The Mayo Clinic, Rochester, Minn., USA headed by Dr Svetomir Markovic. Serial CRP measurements were taken every 2-3 days for 2 weeks. The CRP oscillation cycle was identified by analysis of the raw data without any computer aided modelling, and chemotherapy with temozolomide (200 mg/m2 for 5 days, every 28 days) was initiated. Patients were evaluated for clinical and immune response endpoints every 8 weeks until progression.

Analysis of Immune System Cycling

In the described embodiment the model form is:

$$\log(CRP_i) = \cos\left(2\pi \times \left(\frac{day_i - \text{offset}}{\text{period}}\right)\right) \times \text{amplitude} + \text{mean} + \epsilon_i$$

That is, the natural logarithm CRP of a patient on day i is considered a harmonic function where the parameters (period, offset, mean, and amplitude) of the curve are unknown, and are estimated from the data. The assumptions that are necessary for having reasonable faith in the model are that: the model form is correct; the residuals $\epsilon_i \sim N(0, \sigma^2)$; and the residuals are independent.

This embodiment uses the natural logarithm because extensive testing suggests that otherwise, the fitting algorithm is strongly affected by observations that are unusually high. Furthermore as the CRP measurement refers to a concentration, which is constrained to be greater than zero, the log transformation is a natural one to try.

The model form is non-linear. The consequence of the non-linearity is that in order to estimate the model parameters, it is necessary to nominate a starting point for each one. A consequence of this necessity is that the predicted values may depend on the initial values, especially in cases when data are sparse. In order to provide some objectivity, the present embodiment uses three start points for the period, for three separate fits of the model. This allows any disparity between the outcomes to be considered an indication of poor quality of the data.

Although this embodiment uses a model form defined by a sine curve to estimate the periodicity of the cycling of the biomarker, it will be appreciated that any other suitable periodic regression techniques may be used. One example is Fourier analysis, which is suitable for applications where the measurements do not follow a symmetrical relation as a sine curve. In this case, the measurements can be fitted into a finite Fourier series, which is a sum of finite sine and cosine curves and allows higher harmonics to be considered.

Additionally or alternatively, machine learning algorithms may be used to estimate the periodicity of the cycling of the biomarker, such as:

(a) Bayesian regression analysis, which involves determining a function for the relationship between the measurements (marker) and the periodicity (period), and calculating a conditional posterior probability distribution the periodicity conditional on the measurements, i.e. p(period|marker)

(b) Artificial neural network, where the measurements (marker) are defined as input nodes, and the periodicity of the cycling of the measurements (period) as output node. Each input node is multiplied by a random weight, and the relationship between the input nodes and the output node is a hidden at the hidden node. The weights are estimated until a best-fit curve of the periodicity is obtained as a function of the measurements. The operation of estimating the weights is known as training.

(c) Classification algorithms, where measurements (marker) are classified or placed into groups based on one or more inherent characteristics of the measurements. Classification is one form of supervised machine learning, where classifiers such as neural network, support vector machines and k-means clustering can be used. Random forest regression techniques can be used, where a random forest is a collection of tree predictors that are each built independently from the others using a random vector.

Fit

The model fit approach proceeds as follows. The following steps are repeated for three different starting estimates of period: 5 days, 7 days, and 9 days.

1) Use an optimization algorithm from Byrd et al. (1995) that allows box constraints on the parameter estimates to maximise the likelihood of the observations conditional on the model, the data, and the assumed underlying distribution. This is done for t with degrees of freedom among 3, 5, 10, 20, 40, 70, 100, and 1000, which differ in their tolerance to outliers. The box constraints help guide the optimization into biologically realistic regions.

2) If the model fits described in the previous step fail, the strategy is repeated using the same algorithm but without the box constraints.

3) The model that has the highest log-likelihood is chosen.

4) The parameter estimates are used to estimate the remaining time until the next peak from the assumed current day, which depends on the delay since the final measurement.

5) The parameter estimates, their asymptotic standard errors, and the estimated wait time are reported. These factors are integrated by the analyst to establish the best possible time for treatment, or the best possible time for further measurements, conditional on the model.

Assessment

An assessment of the quality of the fit and the relative reliability of the estimates, including the estimated time to wait until treatment, is provided by the construction of confidence intervals. The confidence intervals are based on the bootstrap technology (Davison and Hinkley, 1997), using the so-called parametric, normal bootstrap intervals.

These randomly-generated intervals are designed to cover the true value about 95% of the time, but their behaviour is guaranteed only in very large sample sizes. Normal intervals appear to have the best overall pattern of behaviour.

Interpretation

Each patient report comprises two panels; (1) a plot of patient data, and (2) a plot of patient data with models overlaid. We omit the first panel to save space. Each plot shows a vertical grey line; this line represents 'today' and allows for the fact that there will most often be a delay between the taking of the final measurement and the time of data analysis. For example, in FIG. 7, the analysis took place on August 14, and the last measurement was taken on August 9.

The second panel provides a prediction of when to treat the patient (currently aiming for the peak of the cycle), along with a considerable amount of diagnostic information. The estimated optimal wait time (in days) is the presented in the first column of the legend box.

The diagnostic information is used to assess the quality of the prediction.

the panel contains up to three model lines. The overlaying of the lines introduces some visual confusion. This is an asset, as it reflects the confusion of the algorithm about the true model.

These three lines represent three different starting points for the model. Ideally the three will be coincident, which implies that the model predictions are identical regardless of the starting point. If the three lines are not coincident, then more measurements are required, and should be taken at times when the projected lines are as far apart as possible, for best resolution.

If more data cannot be obtained then the line that corresponds to the highest value of 11 (log-likelihood, reported in box) should be used, subject to the following qualifiers.

The legend box also reports the estimated period, P. Previous examinations of these data suggest that a period of close to 7 is common. Periods far from 7 should be treated with suspicion.

A visual examination and comparison of the curves should be undertaken. It is sometimes possible to distinguish between competing curves by eye if the statistics are ambiguous.

When the curve is chosen, it must be interpreted. The legend box reports WL, which is the approximate length of the 95% confidence interval of the expected wait time, in days. This quantity reports the data-based uncertainty of the wait time. If this number is too high, then refer to WO. WO is the approximate length of the 95% confidence interval of the offset. If this number is low when WL is high, then the high variability in the wait time is an artifact of how close 'today' is to the best treatment time. In that case, we will worry less about the variability of WL. If both WL and OL are high, then more data are needed.

Results

The results of each of the patients is described below which includes a rating system used to try to identify those patients whose data could be reliably used by the model. The rating was from 1 (worst) to 5 (best). Rating 5 indicated that the inventors were satisfied that the data matched the model as well as could be expected. Rating 1 indicated that the inventors had little expectation that the model would be reliable.

Patient 1

Figure 7:
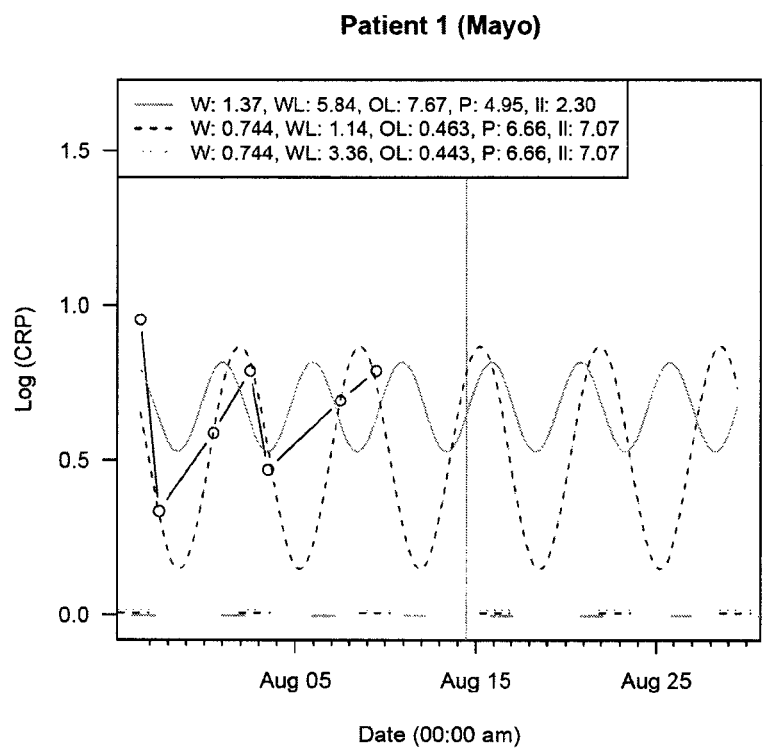
FIG. 7: CRP cycling in Patient 1 from the clinical study.

The treatment appears to have been applied just before the peak of immune system activity (FIG. 7). WL is very large but OL is much smaller; this suggests that the size of WL is an artifact of the model definition. However, there is more than one curve, so the rating was penalized—Rating: 4.

Patient 2

Figure 8:
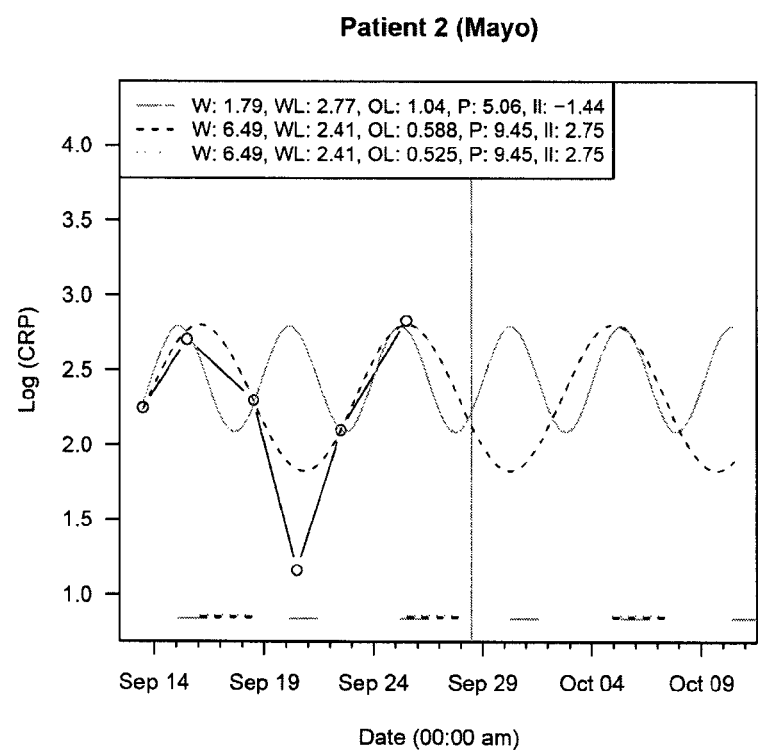
FIG. 8: CRP cycling in Patient 2 from the clinical study.

Analysis of the models suggests the drug was administered to patient 2 when the immune system peaked (FIG. 8). WL is very high but OL very low, this suggests that the size of WL is an artifact of the model definition. There is more than one curve, so the rating was penalized—Rating: 4.

Patient 3

Figure 9:
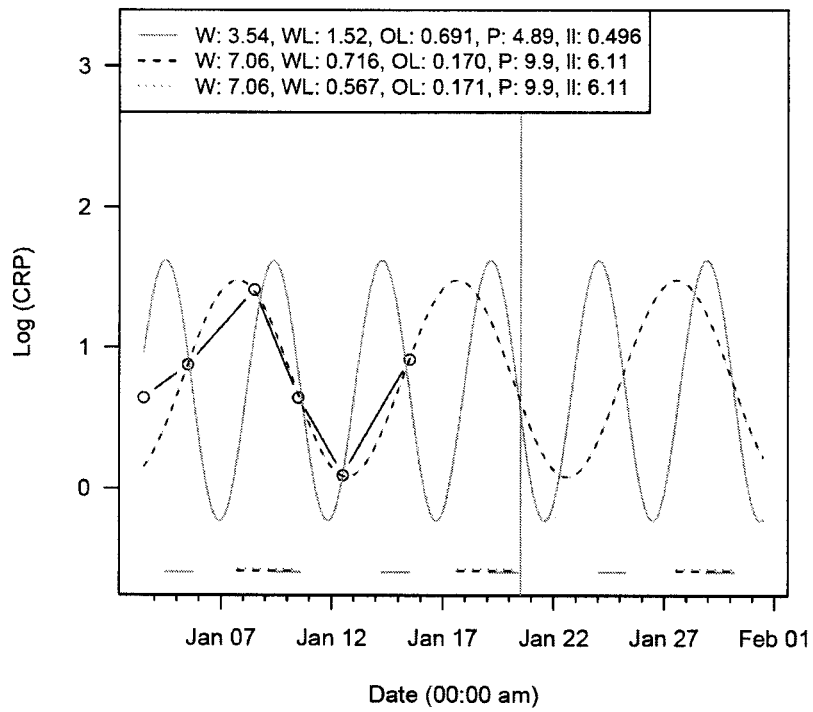
FIG. 9: CRP cycling in Patient 3 from the clinical study.

Analysis of the models suggests the drug was administered to patient 3 on the down-swing of the immune system (FIG. 9). WL is low for all three curves. There is more than one curve, so the rating was penalized—Rating: 4.

Patient 4

Figure 10:
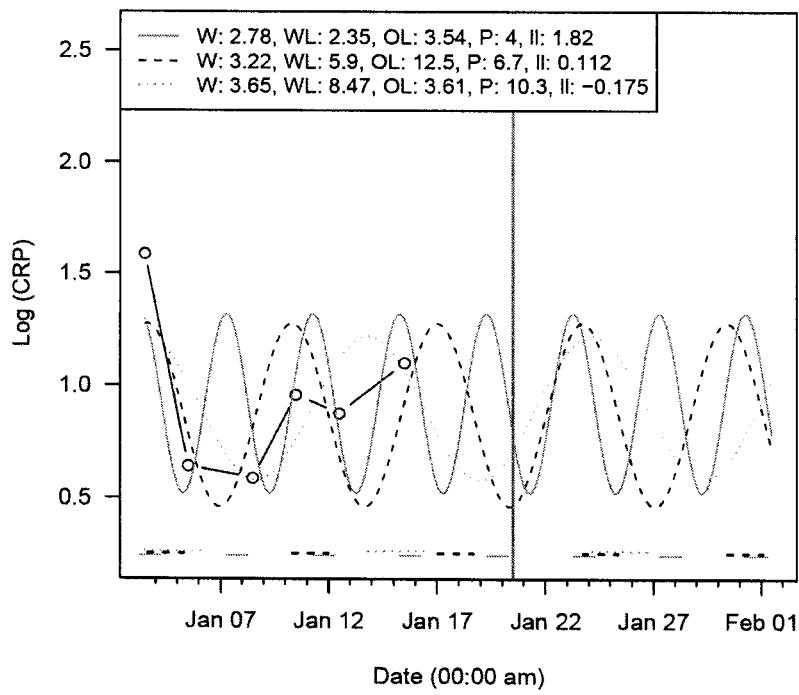
FIG. 10: CRP cycling in Patient 4 from the clinical study.

The analysis suggests the treatment was just past halfway up the slope (FIG. 10), however, more sampling would have provided a clearer determination—Rating: 1.

Patient 5

Figure 11:
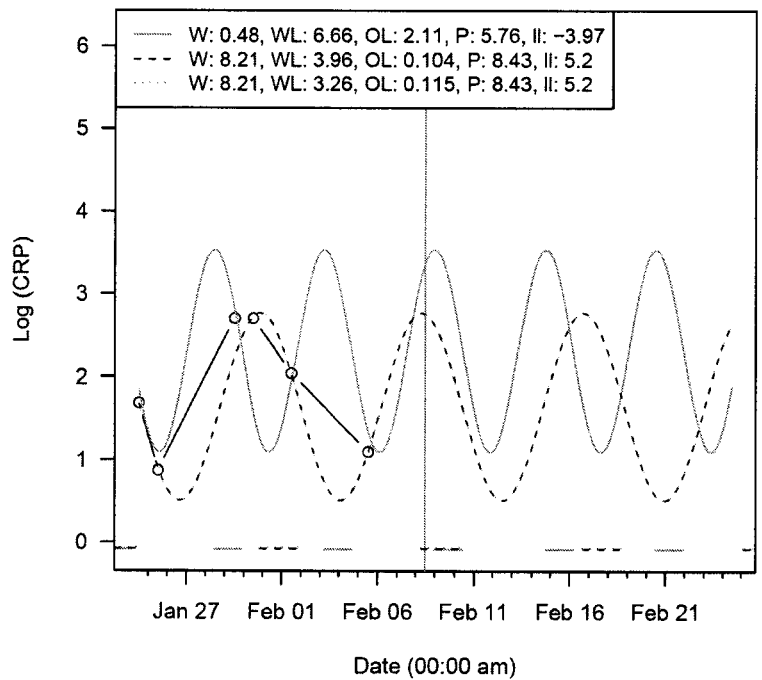
FIG. 11: CRP cycling in Patient 5 from the clinical study.

The treatment appears to have been applied just after the peak of immune system activity (FIG. 11). WL is low. There is more than one curve, so the rating was penalized—Rating: 4.

Patient 6

Figure 12:
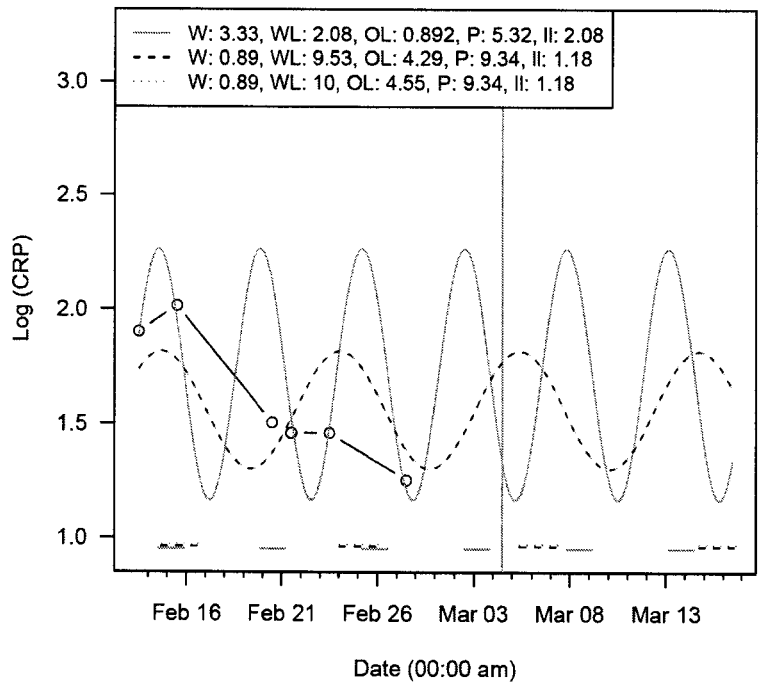
FIG. 12: CRP cycling in Patient 6 from the clinical study.

Unfortunately, the treatment was applied on the day of the third measurement, thus more data would have been preferable—Rating: 1 (FIG. 12). The available data suggests the treatment was applied on the beginning of the downswing of the immune cycle.

Patient 7

Figure 13:
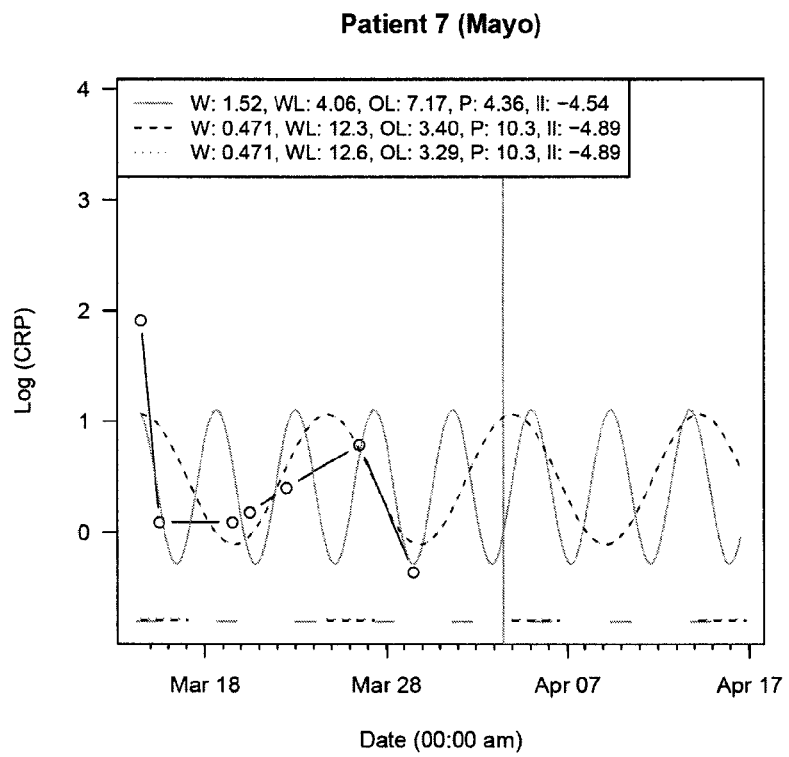
FIG. 13: CRP cycling in Patient 7 from the clinical study.

Analysis suggests treatment was applied some time after the immune system peak (FIG. 13), however, more sampling would have provided a clearer determination—Rating: 1.

Patient 8

Figure 14:
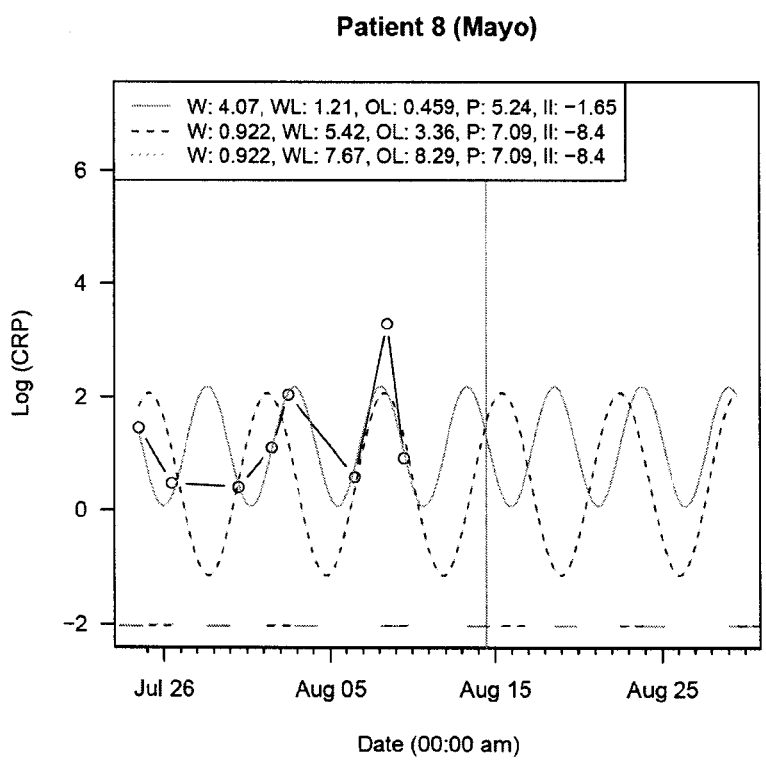
FIG. 14: CRP cycling in Patient 8 from the clinical study.

For patient 8 the curves agree on the relative location of the treatment: at the peak of immune system activity (FIG. 14). There is more than one curve, so the rating was penalized—Rating: 4.

Patient 9

Figure 15:
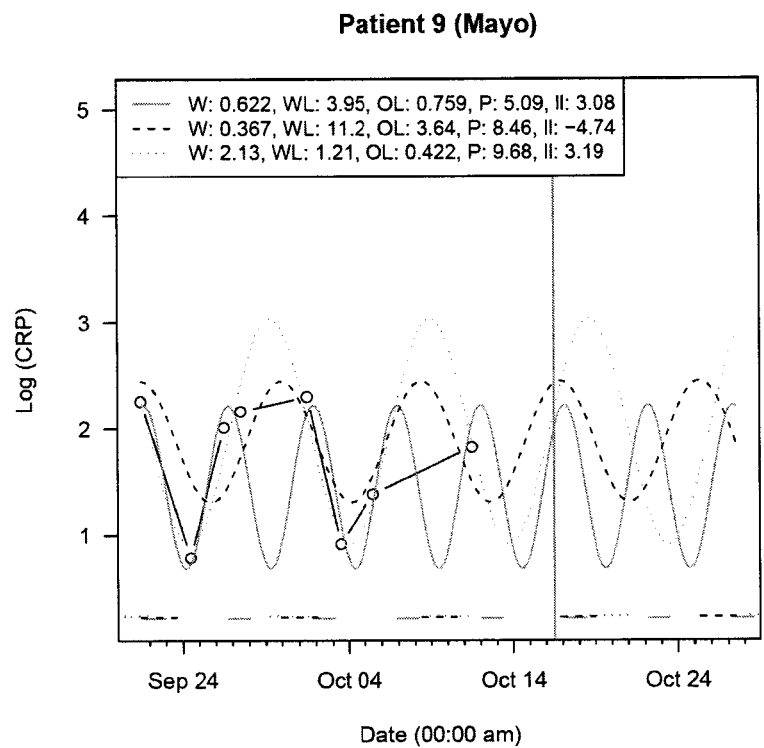
FIG. 15: CRP cycling in Patient 9 from the clinical study.

The relative location of the treatment is on the downswing of immune system activity (FIG. 15). The inventors have reasonable confidence on the location for the data for this patient—Rating: 4.

Patient 10

Figure 16:
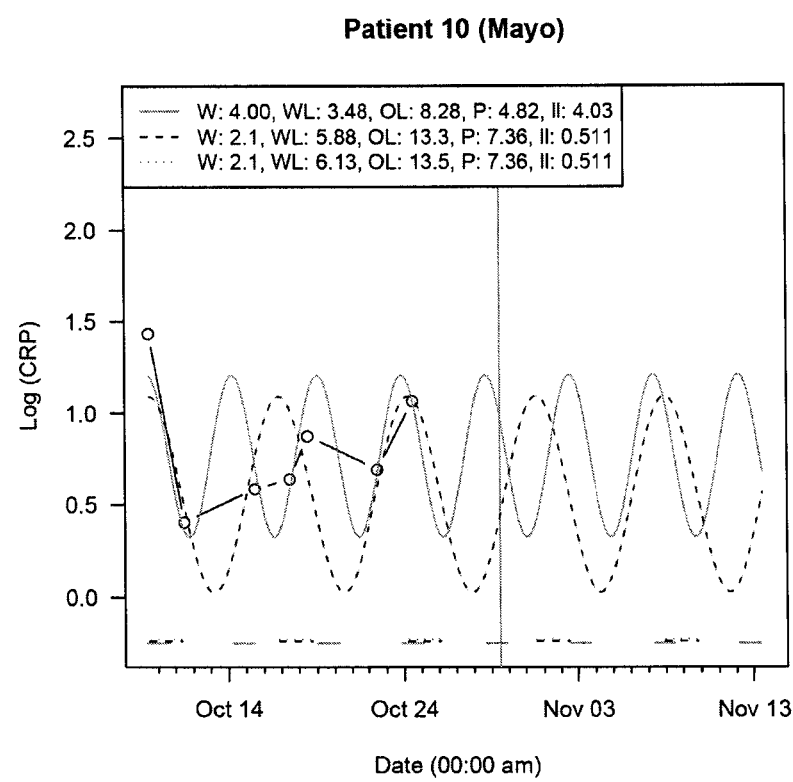
FIG. 16: CRP cycling in Patient 10 from the clinical study.

Fortunately the curves basically agree on the location of the treatment: just on or after the peak (FIG. 16). WL is high—Rating: 3.

Patient 11

Figure 17:
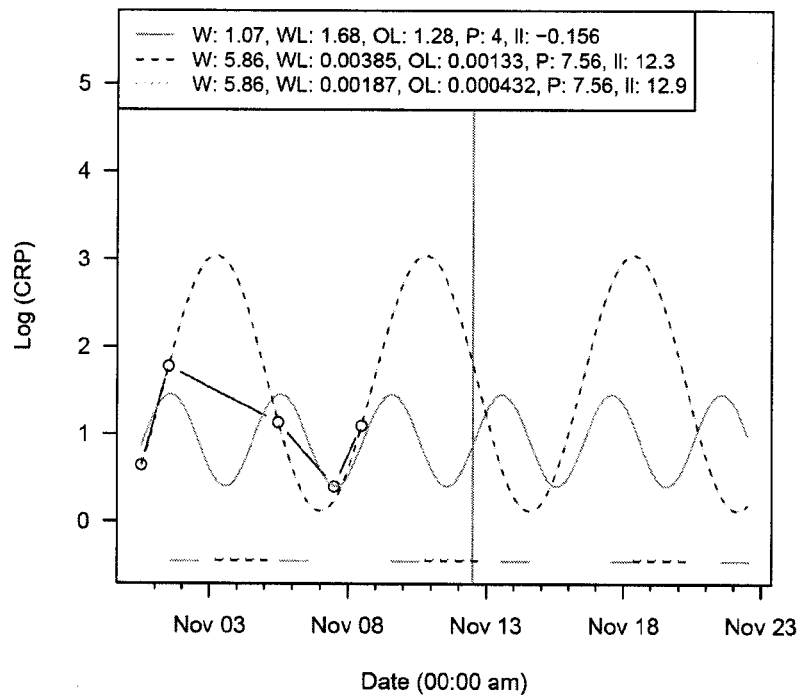
FIG. 17: CRP cycling in Patient 11 from the clinical study.

The data strongly suggests the treatment was applied just as the upswing began. WL is very small (FIG. 17). There is more than one curve, so the rating was penalized—Rating: 4.

Patient 12

Figure 18:
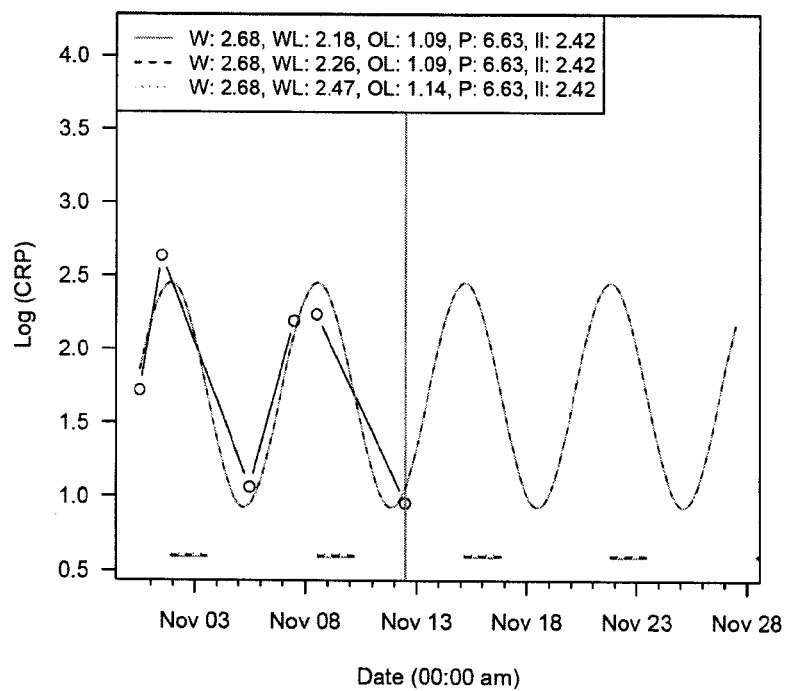
FIG. 18: CRP cycling in Patient 12 from the clinical study.

Treatment was applied just before the peak of immune system activity (FIG. 18). All curves agree, and OL is small—Rating: 5.

Summary

All 12 patients exhibited oscillating CRP levels with an average periodicity of 7.8 days. Only 11 patients were treated (1 patient had rapid tumor progression). The two patients who remain progression-free for >2 years (1 PR, 1 CR), were treated in the pre-peak section of the CRP cycle, distinctly separate from the other patients treated post CRP-peak (all progressed <5 months).

Figure 19:
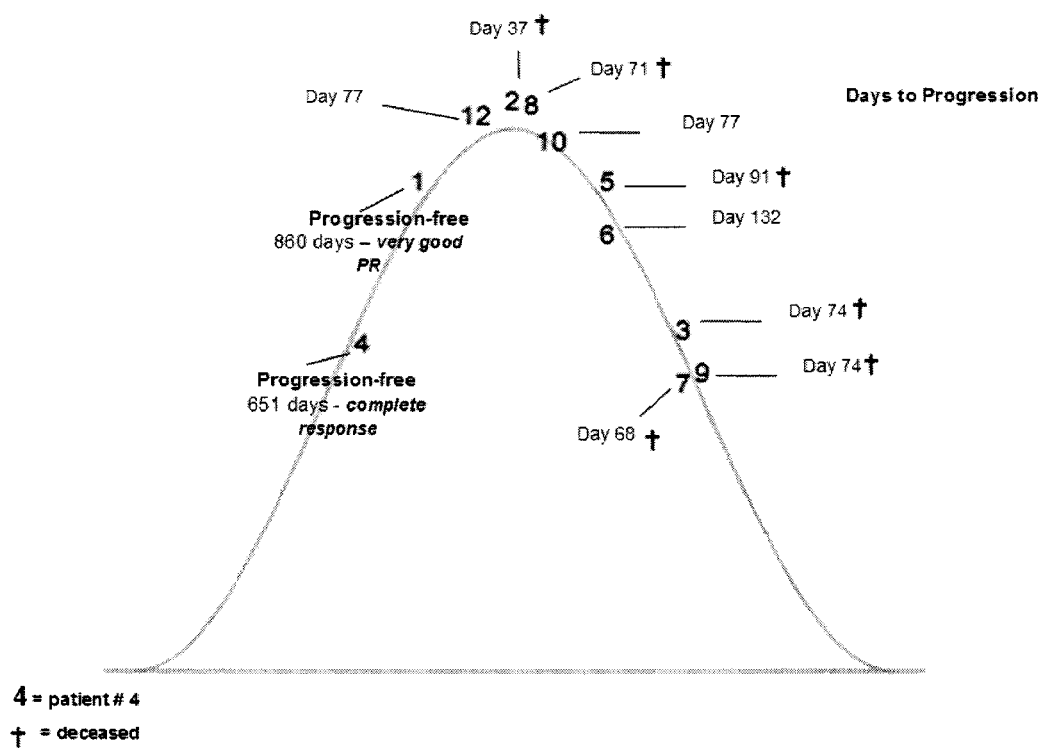
FIG. 19: Overview of predicted patient treatment times. The predicted optimal time of administration based on the pilot study is highlighted.

An overview of predicted patient treatment times is provided in FIG. 19. Patient numbers represented above the line are assigned with high rating (confidence) (4-5), numbers below the line are assigned with low confidence (1-2), numbers on the line have average rating (3).

This data suggests that patient clinical outcome is dependent on the timing of therapy relative to an individual patient's immune response cycle and outline the dynamic equilibrium of systemic immune homeostasis in patients with advanced melanoma. This data suggests that the optimal timing of administration of the therapy to treat cancer in relation to cycling CRP levels is at least about half-way up the rise of the CRP levels but before they have peaked.

Example 2

Modelling to Predict Preferred Timing of Administration—Protocol Assessment

Introduction

The test of the software comprised two main portions: the use of the software on data from real and simulated patients and a simulation study. The overarching goal of the algorithm is to make the prediction as accurate as possible. The inventors can assess its ability to do so in simple, easy-to-grasp cases, as a means of developing intuition about how it will perform in complex cases that are harder to understand.

Simulated Patients

This example provides a demonstration of the use of the fitting algorithm on simulated patients.

Random patient were generated as follows:
>p.random<-patient(id="15 Daily Measures", delay=5, random=TRUE, +cv=75, parameters=c(7, 2, 2, 1), rel-.days=0:14)

It will be appreciated that random patients can be generated using any suitable statistical computing environment, such as open-source programming language R and MATLAB.

The random patient is then processed and reported using the following code—>report(p.random). Note that each simulated patient has a light gray harmonic curve. This is the curve that was used to generate the patient's data, so can be thought of as the "truth" that our algorithm is trying to match. The inventors experimented with the underlying variability until we found level that seemed consonant with the variability observed in the data from the measured patients.

Low Variability

The inventors started with low-variability scenarios here to provide a sense of how the fitting algorithm works for "ideal" patients.

Figure 20:
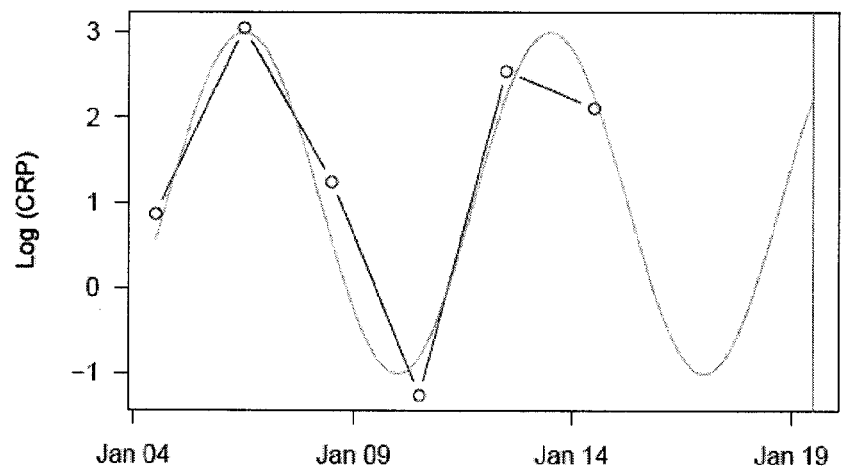
FIG. 20: Example report for a randomly-generated patient. This low-variability patient has six measures, each spaced two days apart.
Figure 20:
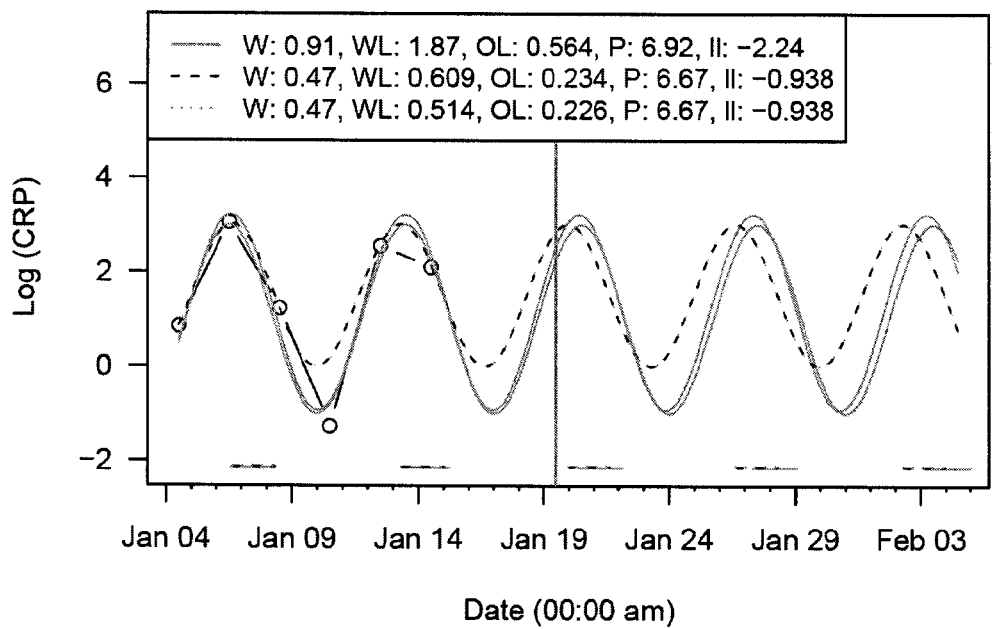

FIG. 20 shows a typical scenario of six measurements spaced two days apart. The variability and poor fit created by this design are reasonably well captured in the figure. The length of the 95% confidence intervals of the estimated wait time (WL) is low enough for satisfactory prediction, but the model choice is not unequivocal.

Figure 21:
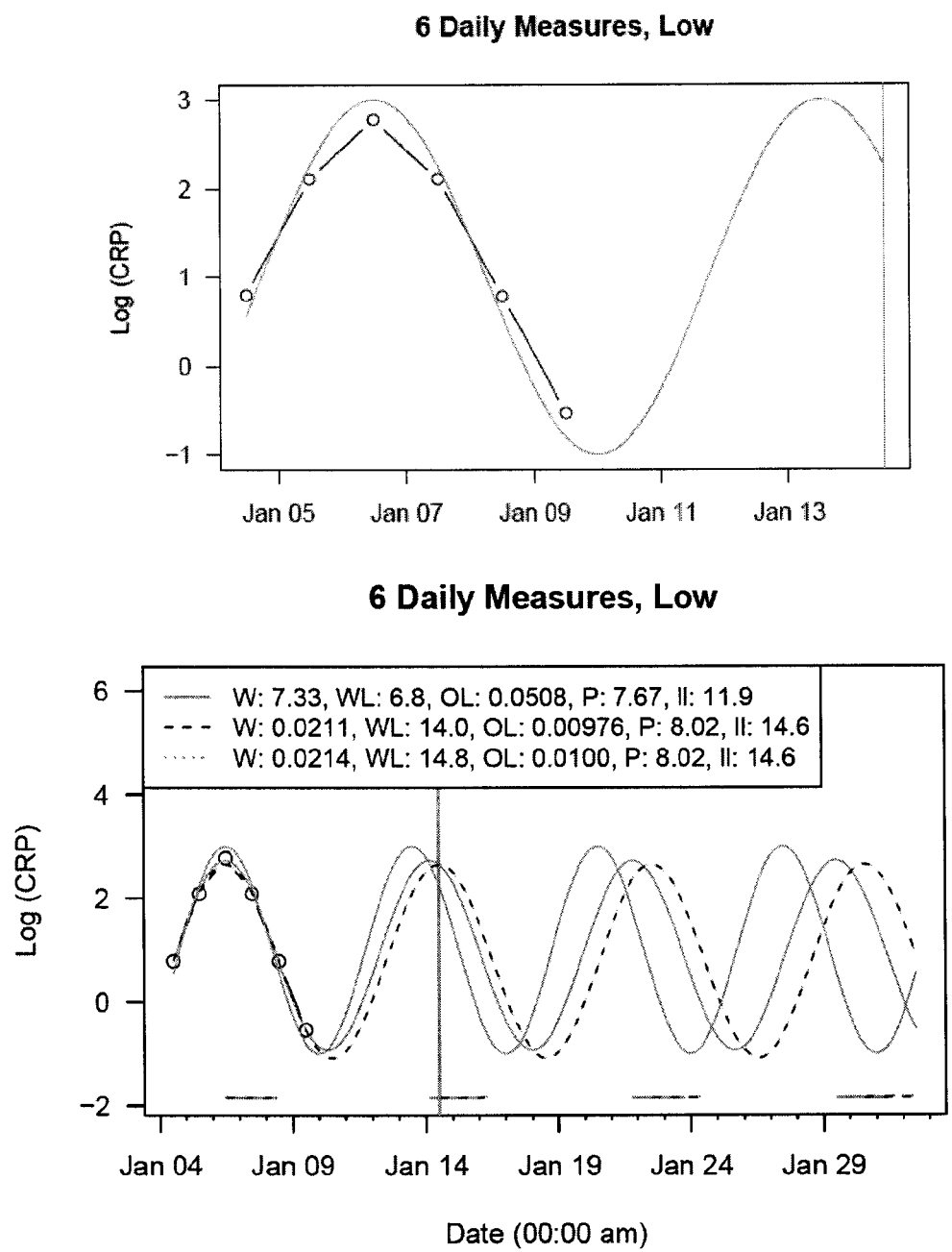
FIG. 21: Example report for a randomly-generated patient. This low-variability patient has six measures, each spaced one day apart.

FIG. 21 shows six measurements spaced one day apart. This scenario provides a timely warning: in a cycle of seven days, measuring at the wrong six days can be misleading. Here, the model is uncertain of the period because of the errors in the measurements and the small number of measurements. The length of the 95% confidence intervals of the estimated wait time (WL) is high in this case.

Figure 22:
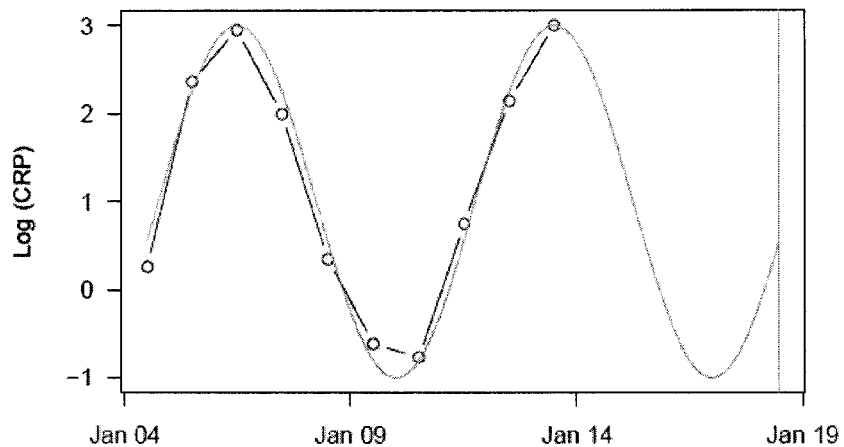
FIG. 22: Example report for a randomly-generated patient. This low-variability patient has ten measures, each spaced one day apart.
Figure 22:
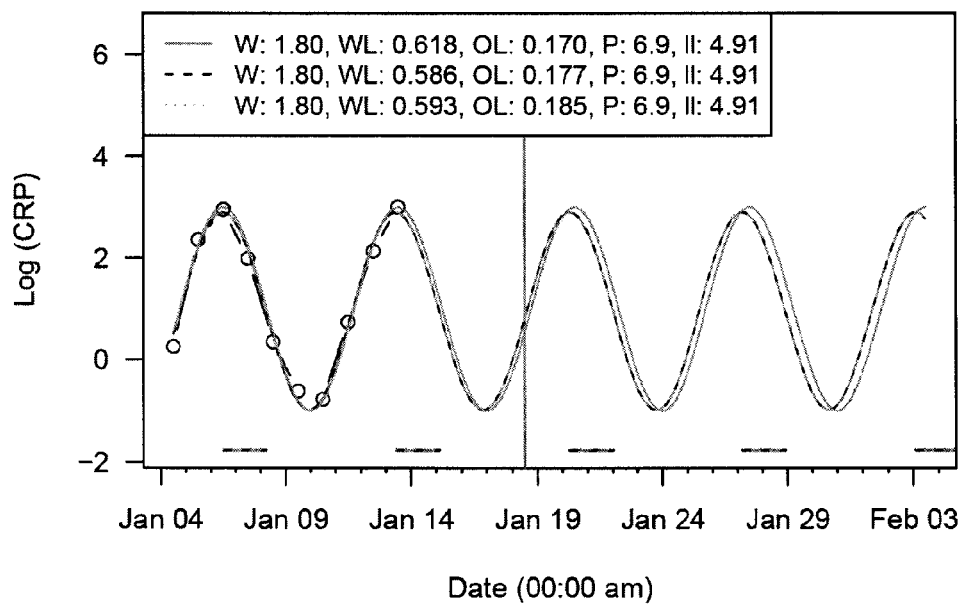

FIG. 22 shows ten daily measurements. The benefit of four extra measurements is clear. The predicted curve matches the actual curve quite well.

Figure 23:
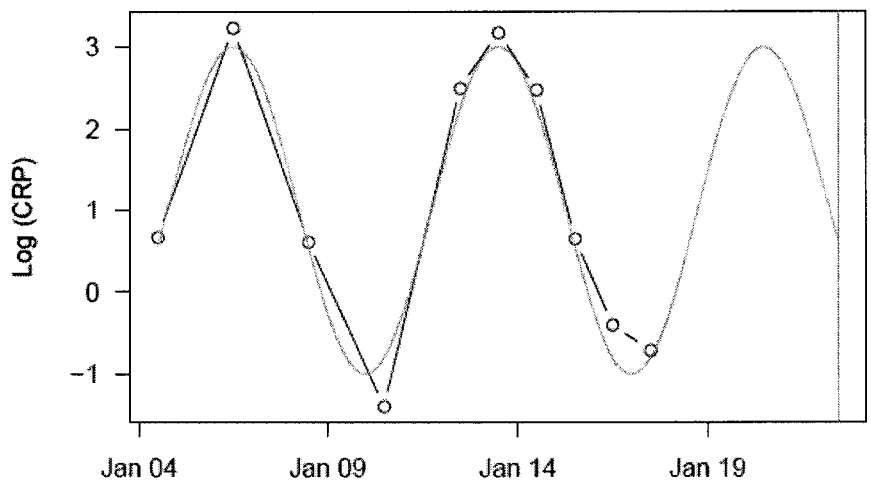
FIG. 23: Example report for a randomly-generated patient. This low-variability patient has ten measures across 14 days.
Figure 23:
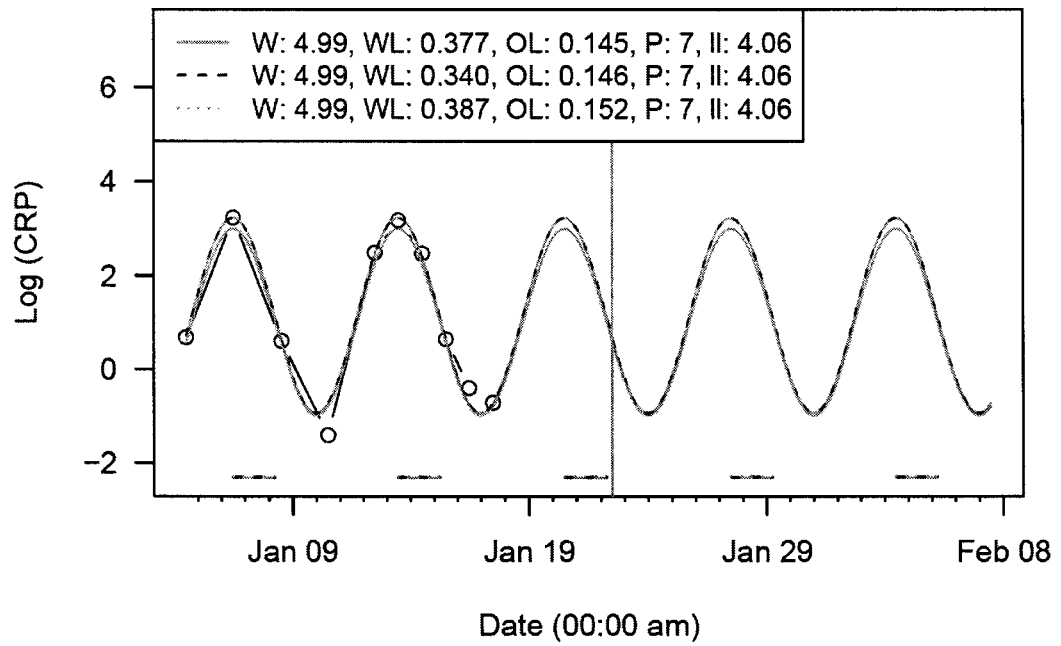

FIG. 23 shows ten measurements spaced across two weeks, with a greater focus on the second week. Again the predicted curve is a good match for the actual curve. The length of the 95% confidence interval of the estimated wait time (WL) is low enough for satisfactory prediction.

Figure 24:
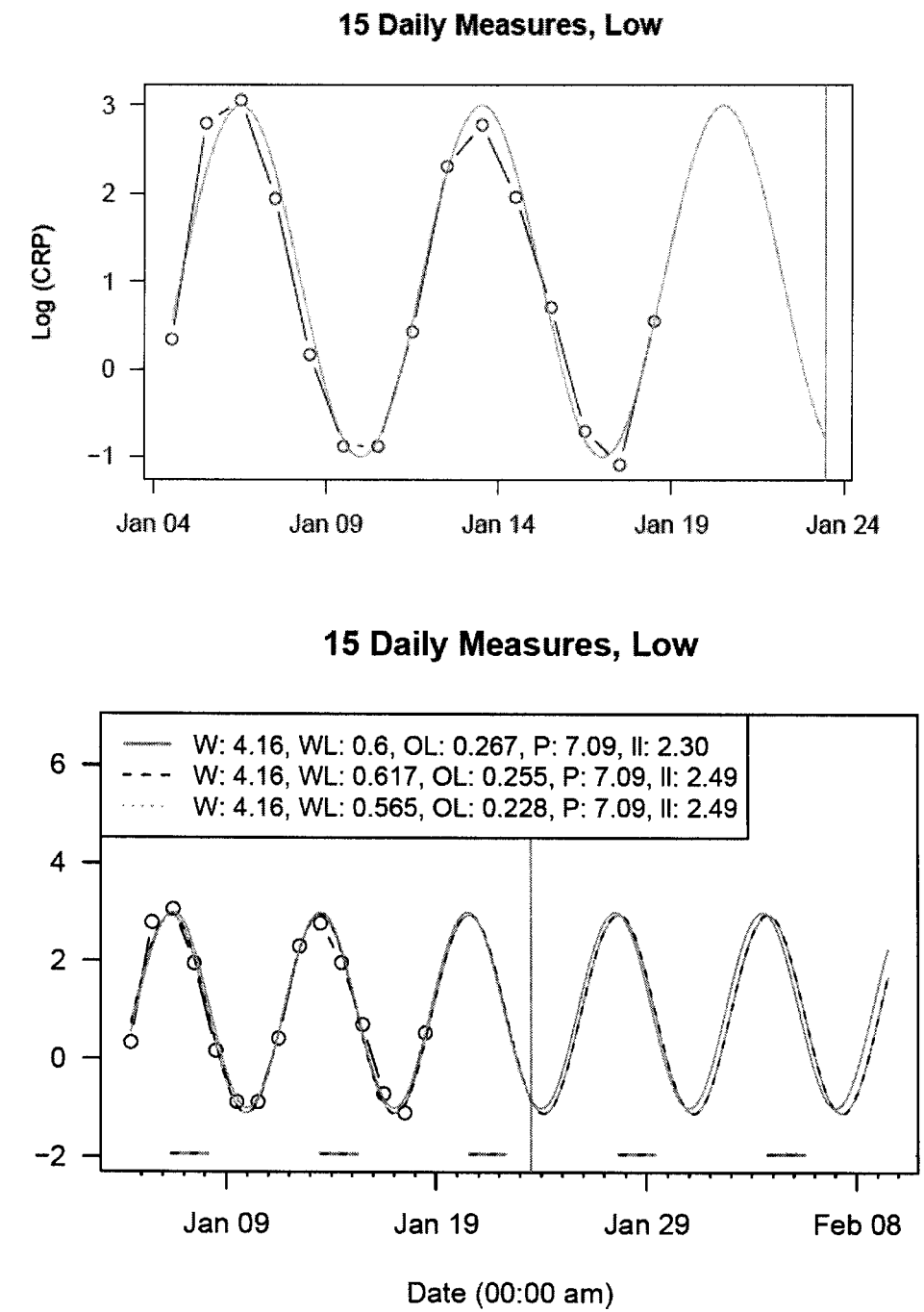
FIG. 24: Example report for a randomly-generated patient. This low-variability patient has fifteen measures, each spaced one day apart.

FIG. 24 shows fifteen daily measurements. Again the predicted curve is a good match for the actual curve. The length of the 95% confidence interval of the estimated wait time (WL) is low enough for satisfactory prediction.

The overview from these simulations is that the algorithm performs well for low variability patients.

High Variability

Five high-variability scenarios here are analysed to provide a sense of how the fitting algorithm works for "difficult" patients.

Figure 25:
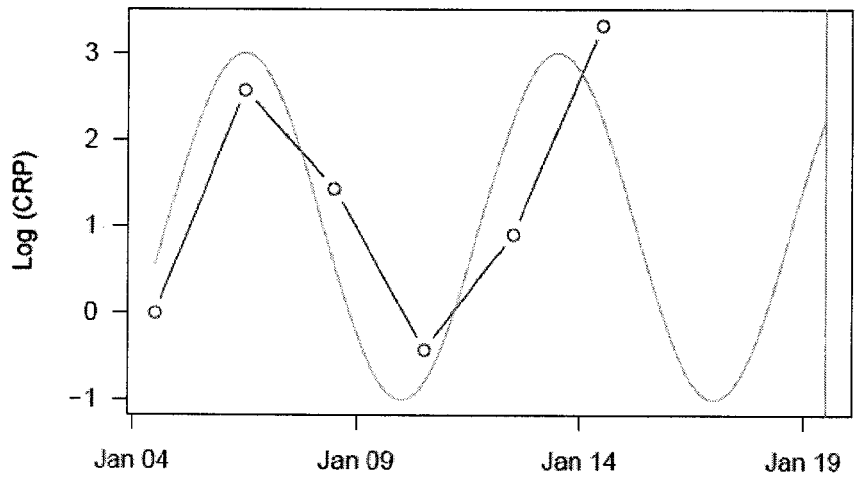
FIG. 25: Example report for a randomly-generated patient. This high-variability patient has six measures, each spaced two days apart.
Figure 25:
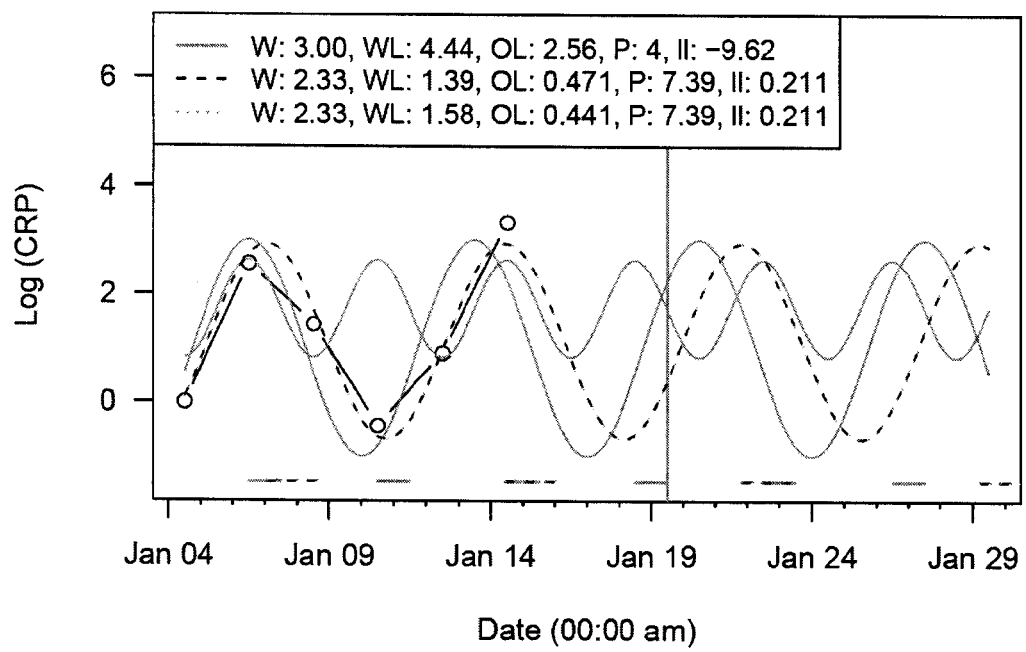

FIG. 25 shows a typical scenario of six measurements spaced two days apart. The variability and poor fit created by this design are reasonably well captured in the figure. The length of the 95% confidence intervals of the estimated wait time is low, but not low enough for satisfactory prediction.

Figure 26:
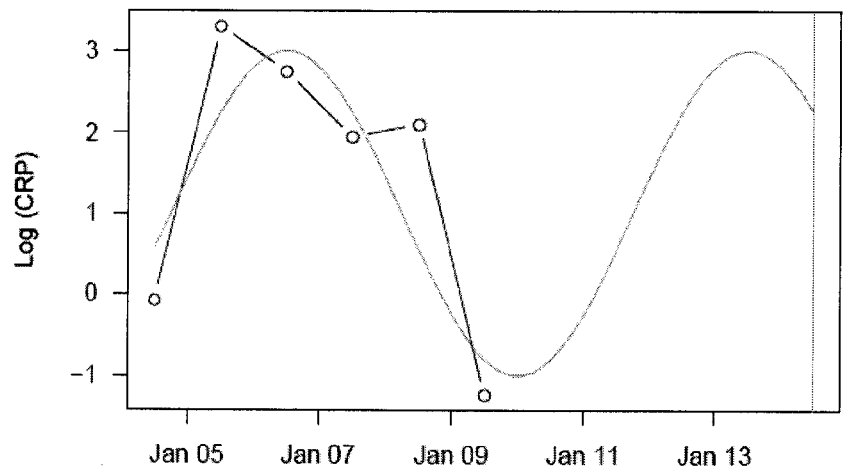
FIG. 26: Example report for a randomly-generated patient. This high-variability patient has six measures, each spaced one day apart.
Figure 26:
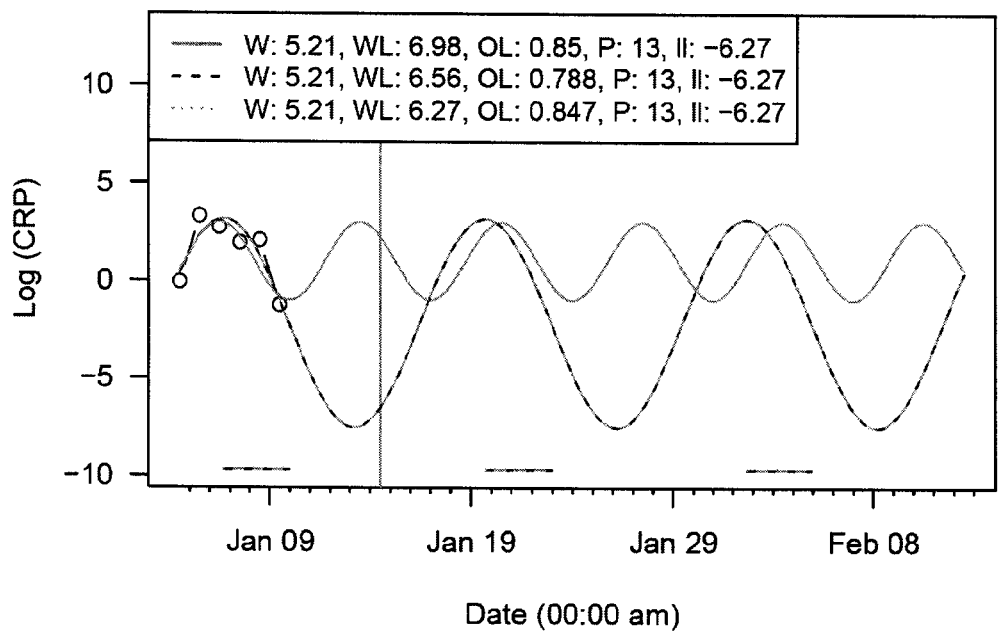

FIG. 26 shows six measurements spaced one day apart. This scenario provides a timely warning: in a cycle of seven days, measuring at the wrong six days can be extremely misleading. Here, the model fails to capture the periodicity because of the errors in the measurements and the small number of measurements. We see warning flags in the exceptionally large estimate of the period, but nowhere else in our diagnostics.

Figure 27:
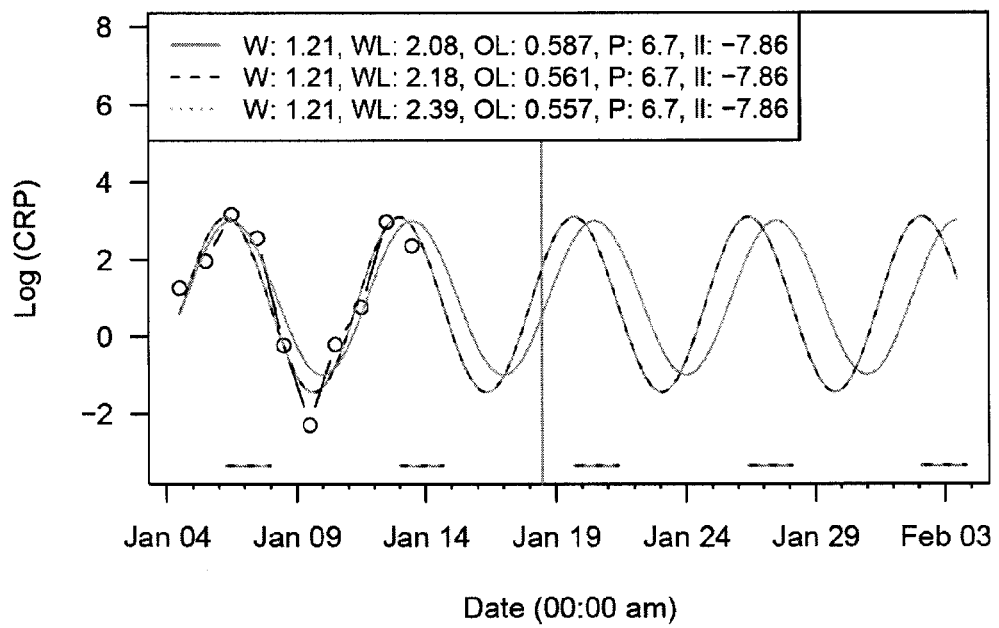
FIG. 27: Example report for a randomly-generated patient. This high-variability patient has ten measures, each spaced one day apart.
Figure 27:
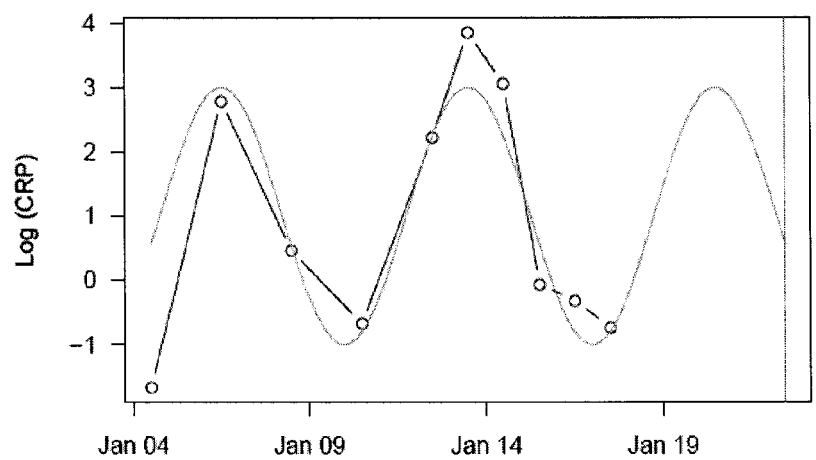

FIG. 27 shows ten daily measurements. The benefit of four extra measurements is clear. The predicted curve matches the actual curve quite well, although the importance of timeliness is also obvious. Within a few weeks of the last measurement, the estimated window of treatment probably no longer overlaps the actual window. This is of concern even ignoring the possibility that the patient's immune response could change timing of its own accord, or in response to stimuli.

Figure 28:
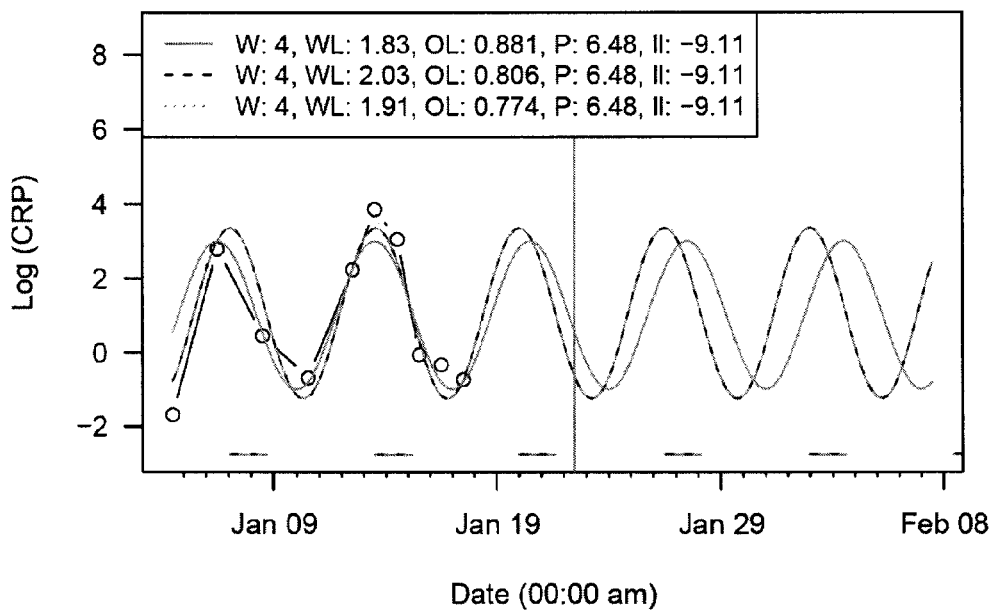
FIG. 28: Example report for a randomly-generated patient. This high-variability patient has ten measures across 14 days.
Figure 28:
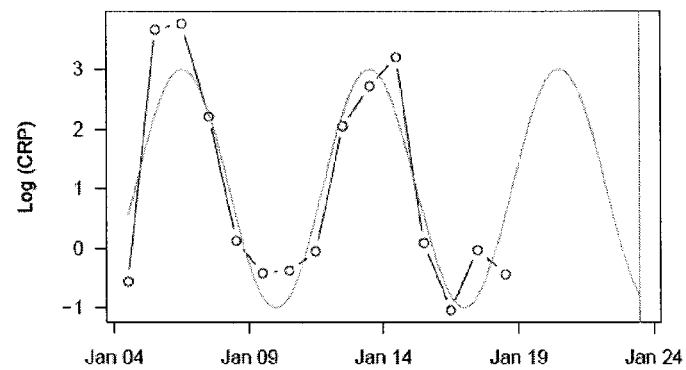

FIG. 28 shows ten measurements spaced across two weeks, with a greater focus on the second week. Again the predicted curve is a good match for the actual curve. The length of the 95% confidence interval of the estimated wait time is low, but not quite low enough for satisfactory prediction.

Figure 29:
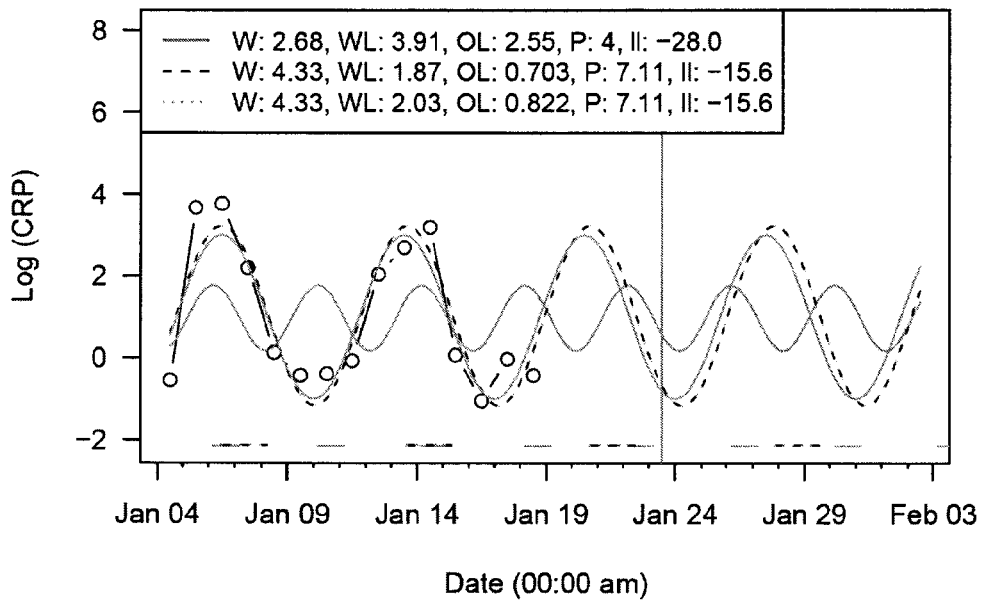
FIG. 29: Example report for a randomly-generated patient. This high-variability patient has fifteen measures, each spaced one day apart.

FIG. 29 shows fifteen daily measurements. One of the curves has missed the pattern altogether, but if we follow our algorithm then the prediction from this curve would not be used anyway. The overview from the high-variability random patients is less encouraging, which is an expected result. As the underlying variability of the signal increases, we are able to rely less on the data to inform us about the nature of the true signal.

Conclusions

The results suggest that the proposed strategy is defensibly robust and works under a wide range of different circumstances. However, care is required in its application, and datasets of reasonable size (e.g. at least 10) will yield better results. If the sample size is too small then the confidence with which the technique identifies the location of the treatment window will be overstated.

Example 3

Simulation Study

Materials and Methods

The present inventors used the model and fitting algorithm as laid out in Example 1. The goal was to assess the impact upon prediction performance of the number of measures taken, the timeframe over which they were taken, and the pattern of spacing. It is reasonable to expect that the underlying variability of the patients biological signal would also affect the quality of the model fit. Therefore the design for the simulation study comprised the following elements:

1. Variation in length, including one, one and a half, and two weeks;
2. Variation in number of measurements, including 8, 10, 15, and 21;
3. Variation in measurement pattern, including symmetric (S), concentration early and late (B), and concentration late (L); and
4. Variation in underlying patient variability, including very small (0.25%) and nominal CRP variation (4%) to large (30%).

The inventors simulated 500 random patients with each of the three underlying amounts of variability, crossed with each different measurement scenario. A full factorial experimental design was not used owing to time constraints. Each random patient was fitted using the suggested algorithm. For each patient we then assessed the length of their confidence interval and whether or not the interval contained the true value from which the patient had been simulated.

Results

Figure 30:
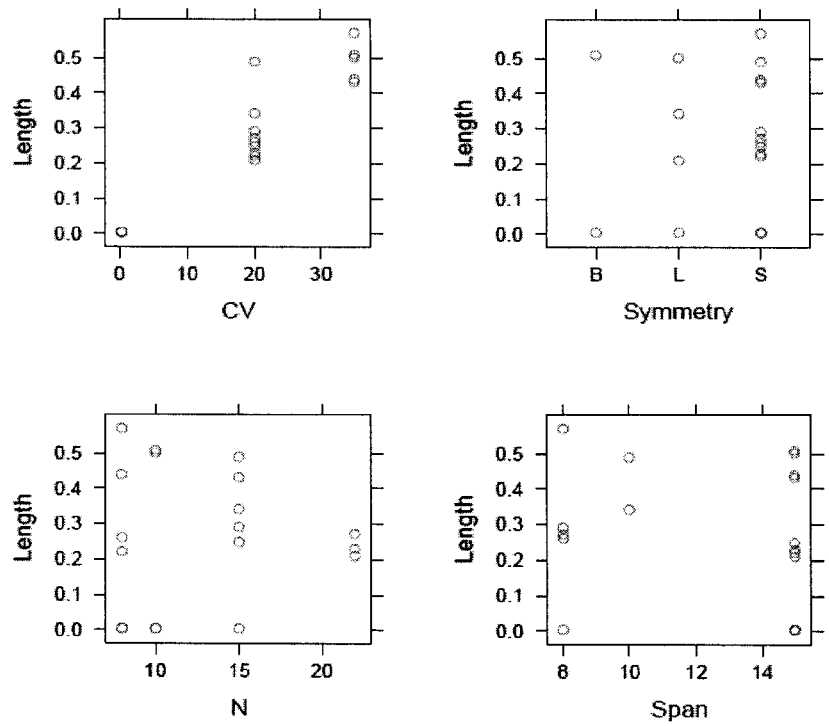
FIG. 30: Summary plot of the interval lengths of the simulations. The nominal rate is 0.95. CV refers to the patient's underlying variability; Symmetry differentiates between those designs that are (S)ymmetric, those that have a preponderance of measurement (L)ate, or with more points allocated to (B)oth tails; N is the number of measurements, and Span refers to the number of days for the full regime. The interval length increases with increasing underlying variability, and seems unaffected by measurement symmetry, span, and the number of measurements. However, these results should be interpreted in the light of those presented in FIG. 31.

The full results of the simulations are presented in Table 1, and the specific results for interval length are summarized in FIG. 30. The results for interval coverage rates are summarized in FIG. 31.

TABLE 1

Results from simulations.

| Variability | Count | Span | Symmetry | Coverage | Length |
|---|---|---|---|---|---|
| 0.25 | 8 | 8 | S | 0.714 | 0.0033 |
| 0.25 | 8 | 15 | S | 0.742 | 0.0027 |
| 0.25 | 15 | 15 | S | 0.844 | 0.0029 |
| 0.25 | 10 | 15 | L | 0.780 | 0.0026 |
| 0.25 | 10 | 15 | B | 0.810 | 0.0033 |
| 20.00 | 8 | 8 | S | 0.678 | 0.2600 |
| 20.00 | 8 | 15 | S | 0.676 | 0.2200 |
| 20.00 | 15 | 15 | S | 0.848 | 0.2500 |
| 20.00 | 15 | 10 | S | 0.848 | 0.4900 |
| 20.00 | 15 | 8 | S | 0.874 | 0.2900 |
| 20.00 | 22 | 8 | S | 0.888 | 0.2700 |
| 20.00 | 22 | 15 | S | 0.906 | 0.2300 |
| 20.00 | 15 | 10 | L | 0.860 | 0.3400 |
| 20.00 | 22 | 15 | L | 0.900 | 0.2100 |
| 35.00 | 8 | 8 | S | 0.720 | 0.5700 |
| 35.00 | 8 | 15 | S | 0.750 | 0.4400 |
| 35.00 | 15 | 15 | S | 0.870 | 0.4300 |
| 35.00 | 10 | 15 | L | 0.800 | 0.5000 |
| 35.00 | 10 | 15 | B | 0.790 | 0.5100 |

The Variability refers to the coefficient of variation of the data;
Count is the number of measurements;
Span is the number of days over which the measurements were made;
Symmetry refers to the distribution of the measurements across the days, including (S)ymmetric, (L)ate-focused, and (B)oth early and late;
Coverage is the simulated coverage probability (nominally 0.95); and
Length is the average length of the intervals, in days.

DISCUSSION AND CONCLUSION

Based upon the patient data that were available, the nominal figure of 4% variation in CRP measurements seems very low. It is also possible that the figure is correct but our model fails to capture some important source of variation. This study suggests that the proposed modeling technique works better with at least moderate numbers of data points, say at least 10. The arrangement of the measurement points and the span of time that they occupy does not seem to affect the outcome, at least across the range of scenarios compared here. The underlying variability of the measurements does affect the outcome, and efforts should be made to ensure that measurements are made in as uniform a collection of circumstances as is possible.

The goals of the simulation study were two-fold: firstly to provide guidance as to the most suitable measurement timing regime; and secondly, to provide feedback on the reliability of the fitting routine. The second goal is addressed here.

The measure of reliability that is focused on is the realized coverage rate of the random intervals. The nominal coverage rate is 0.95, and closeness to this coverage should be regarded as one measure of the quality of the fitting approach. However, with the small sample sizes that we are using, and the nature of the model being fitted, it would be very surprising to achieve coverage rates that high. Furthermore, it is not essential that the intervals achieve any particular coverage rate because they are being used an informal way, to provide feedback as to the reliability of the data and model, rather than as a formal inferential tool.

Figure 31:
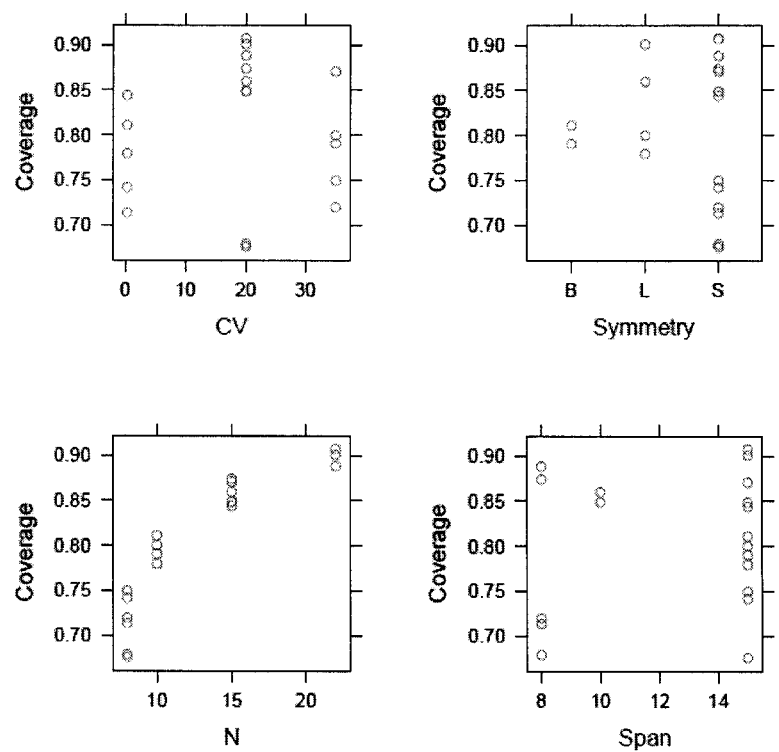
FIG. 31: Summary plot of the interval coverage rates of the simulations. The nominal rate is 0.95. CV refers to the patient's underlying variability; Symmetry differentiates between those designs that are (S)ymmetric, those that have a preponderance of measurement (L)ate, or with more points allocated to (B)oth tails; N is the number of measurements, and Span refers to the number of days for the full regime. Coverage increases with increasing sample size, seems largely unaffected by the span of the measurement period, symmetry and underlying variability.

The coverage rates and interval lengths from the simulation study are reported in Table 1. The simulation study suggests that the underlying variability of the signal does not greatly affect the quality of the intervals, as measured by the closeness of the coverage rate to 0.95. The coverage increases with increasing sample size, seems largely unaffected by the span of the measurement period, symmetry and underlying variability (FIG. 31).

The inventors conclude that for sufficiently large numbers of observations, say 10 or more, the coverage rate is reasonably good for the fitting technique. This provides reasonable confidence for the technique itself, as well as the use of the intervals as diagnostic tools for modeling with real patients.

Samples that are too small will have overstated coverage, which means that the intervals are shorter than imagined. This means that the result will overstate the confidence with which we can identify the location of the treatment window.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The present application claims priority from U.S. 61/181, 508 filed 27 May 2009, the entire contents of which are incorporated herein by reference.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Allan et al. (2008) Immunol. Rev. 223:391-421.
Annunziato et al. (2002) J. Exp. Med. 193:1285-1294.
Aziz et al. (1998) Cancer Detect. Prev. 22:87-99.
Babbe et al. (2000) J. Exp. Med. 192:393-404.
Belkaid and Rouse (2005) Nat. Immunol. 6:353-360.
Bottazzo et al. (1985) New Engl. J. Med. 313:353-360.
Brusko et al. (2008) Immunol. Rev. 223:371-390.
Byrd et al. (1995) SIAM J. Scientific Computing, 16:1190-1208.
Cao et al. (2009) AIDS Res. Hum. Retroviruses 25:183-191.
Davison and Hinkley (1997) Bootstrap methods and their application. Cambridge University Press.
Dittmer (2004) Immunity 20:293-303.
Eda et al. (1998) J. Clin. Lab. Analysis 12:137-144.
Estes et al. (2007) J. Infect. Dis. 195:551-61.
Gajewski et al. (2009) Clin. Adv. Hematol. Oncol. 7:1-10.
Goverman (1999) Immunol. Rev. 169:147-159.
Hill et al. (1997) Blood 90:3204-3213.
Horvath et al. (1982) Oncology 39:20-22.
Hryniewicz et al. (2006) Blood 108:3834-3842.
Iwashiro et al. (2001) Proc. Natal. Acad. Sci. US 98:9226-9230.
Jonuleit et al. (2001) J. Exp. Med. 193:1285-1294.
Kimura et al. (2001) Cancer 92:2072-2075.
Kinter et al (2007b) Proc. Natl. Acad. Sci. 104:3390-3395.
Kinter et al. (2004) J. Exp. Med. 200:6331-343.
Kinter et al. (2007a) AIDS Res. Hum. Retroviruses 23:438-450.
Kohm et al. (2002) J. Immunol. 169:4712-4716.
Lim et al. (2006) Immunol. Cell Biol. 84:530-536.
Lim et al. (2007) AIDS 21:1525-1534.
Liuzzo et al. (1994) New Engl. J. Med. 331:417-424.
Monsonego and Weiner (2003) Science 302:834-838.
Murphy and Blazar (1999) Curr Opin Immunol. (1999) 11:509-515.
Nilsson et al. (2006) Blood 108:3808-3817.
North and Awwad (1990) Immunology 71:90-95.
O'Hanlon et al. (2002) Anticancer Res. 22:1289-1294.
O'Hara et al. (2000) Arthritis Res. 2:142-144.
Onizuka et al. (1999) Cancer Res. 59:3128-3133.
Price et al. (1987) J. Immunol. Methods 99:205-211.
Read et al. (2000) J. Exp. Med. 192:295-302.
Rouse et al. (2006) Immunol. Rev. 212:272-286.
Salomon et al. (2000) Immunity 12:431-440.
Santamaria (2001) Curr. Opin. Immunol. 13:663-669.
Senju et al. (1983) Jap. J. Clin. Lab. Automation 8:161-165.
Shimizu et al. (1999) J. Immunol. 163:5211-5218.
Shimizu et al. (2002) Nature Immunol. 3:135-142.
Speiser et al. (1997) J. Immunol. 158:5185-5190.
Suri-Payer and Cantor (2001) J. Autoimmunity 16:115-123.
Sutmuller et al. (2001) J. Exp. Med. 194:823-832.
Takahashi et al. (2000) J. Exp. Med. 192:303-310.
Vahlenkamp et al. (2005) Vet. Immunol. Immunopathol. 108:219-225.
Vahlenkamp et al. (2004) J. Immunol. 172:4752-4761.
Vila et al. (2009) Curr. Opin. Hematol. May 2 [Epub ahead of print]
von Herrath and Harrison (2003) Nature Rev. 3:223-232.
Weinstein et al. (1984) Scand. J. Immunol. 19:193-198.
Weiss et al. (2004) Blood 104:3249-3256.
Wong et al. (1999) Nat. Med. 9:1026-1031.
Wu et al. (2002) Proc. Natl. Acad. Sci. USA 99:12287-12292.

The invention claimed is:

1. A non-transitory computer-readable information storage medium having stored thereon instructions, that if executed by one or more processors, perform a method comprising:
  i) obtaining from a first memory measurements of an acute phase inflammatory marker in samples from a subject having a disease characterized by production of regulator cells and cycling immune system markers;
  ii) obtaining from a second memory a model of cycling of the acute phase inflammatory marker;
  iii) fitting the measurements to the model;
  iv) obtaining a best-fit curve of the measurements to the model to estimate a periodicity of the cycling of the acute phase inflammatory marker;
  v) projecting the obtained best-fit curve into the future; and vi) outputting a preferred time in the future, based on the projected best-fit curve, to administer a therapy to treat the disease;
wherein the preferred time is a time period in the cycling of the acute phase inflammatory marker where the level of the acute phase inflammatory marker is increasing, between halfway between a minimum in the cycle and a maximum in the cycle, but before the level of the acute phase inflammatory marker has peaked; and
wherein the therapy is selected from the group consisting of an anti-proliferative drug and radiation.

2. The computer-readable information storage medium of claim 1, wherein the best-fit curve is a fit to a harmonic model of the cycling of the acute phase inflammatory marker, and obtaining the best-fit curve further comprises fitting the harmonic model to the measurements multiple times using different initial conditions for each fit.

3. The computer-readable information storage medium of claim 1, wherein the method further comprises generating a confidence measure by comparing a similarity in a fit result produced by each fitting.

4. The computer-readable information storage medium of claim 1, wherein obtaining the best-fit curve further comprises imposing a box constraint on at least some parameters of the model to guide optimization to biologically realistic regions.

5. The computer-readable information storage medium of claim 1, wherein the model has a heavy tail to allow for noisy nature of the measurements.

6. The computer-readable information storage medium of claim 1, wherein the method further comprises determining a variance-stabilizing transformation of the measurements prior to determining the periodicity based on the transformed measurements.

7. The computer-readable information storage medium of claim 6, wherein the variance-stabilizing transformation of measurements is logarithm of the measurements.

8. The computer-readable information storage medium of claim 1, wherein the measurements are for two or more different acute phase inflammatory markers which are cycling in the subject.

9. A computer system for determining a preferred time to administer a therapy to treat a disease characterized by cycling immune system markers, the computer system comprising:
a first memory for storing measurements of an acute phase inflammatory marker in samples from a subject having a disease characterized by production of regulator cells and cycling immune system markers;
a second memory for storing a model of cycling of the acute phase inflammatory marker; and
one or more processors to:
i) fit the measurements to the model;
ii) obtain a best-fit curve of the measurements to the model to estimate a periodicity of the cycling of the acute phase inflammatory marker;
iii) project the obtained best-fit curve into the future;
iv) output a preferred time in the future, based on the projected best-fit curve, to administer a therapy to treat the disease;
wherein the preferred time is a time period in the cycling of the acute phase inflammatory marker where the level of the acute phase inflammatory marker is increasing, between halfway between a minimum in the cycle and a maximum in the cycle, but before the level of the acute phase inflammatory marker has peaked; and
wherein the therapy is selected from the group consisting of an anti-proliferative drug and radiation.

\* \* \* \* \*